US010519448B2

(12) United States Patent
Collard et al.

(10) Patent No.: US 10,519,448 B2
(45) Date of Patent: Dec. 31, 2019

(54) TREATMENT OF BRAIN DERIVED NEUROTROPHIC FACTOR (BDNF) RELATED DISEASES BY INHIBITION OF NATURAL ANTISENSE TRANSCRIPT TO BDNF

(71) Applicant: CuRNA, Inc., Miami, FL (US)

(72) Inventors: Joseph Collard, Delray Beach, FL (US); Olga Khorkova Sherman, Tequesta, FL (US); Carlos Coito, West Palm Beach, FL (US)

(73) Assignee: CuRNA, Inc., Miami, FL (US)

( * ) Notice: Subject to any disclaimer, the term of this patent is extended or adjusted under 35 U.S.C. 154(b) by 0 days.

(21) Appl. No.: 14/723,740

(22) Filed: May 28, 2015

(65) Prior Publication Data

US 2016/0138023 A1 May 19, 2016

Related U.S. Application Data

(62) Division of application No. 13/201,254, filed as application No. PCT/US2010/024075 on Feb. 12, 2010, now Pat. No. 9,074,210.

(60) Provisional application No. 61/152,132, filed on Feb. 12, 2009.

(51) Int. Cl.

*C12N 15/11* (2006.01)
*C12N 15/113* (2010.01)
*A61K 31/7088* (2006.01)
*A61K 45/06* (2006.01)
*C12Q 1/6883* (2018.01)
*G01N 33/74* (2006.01)
*A61K 48/00* (2006.01)

(52) U.S. Cl.

CPC ...... *C12N 15/1136* (2013.01); *A61K 31/7088* (2013.01); *A61K 45/06* (2013.01); *C12Q 1/6883* (2013.01); *G01N 33/74* (2013.01); *A61K 48/00* (2013.01); *C12N 2310/11* (2013.01); *C12N 2310/113* (2013.01); *C12N 2310/315* (2013.01); *C12N 2320/30* (2013.01); *C12N 2330/10* (2013.01); *C12Q 2600/136* (2013.01); *C12Q 2600/158* (2013.01); *C12Q 2600/178* (2013.01); *G01N 2333/48* (2013.01); *G01N 2500/02* (2013.01)

(58) Field of Classification Search

None

See application file for complete search history.

(56) References Cited

U.S. PATENT DOCUMENTS 4,683,195 A 7/1987 Mullis et al.
4,683,202 A 7/1987 Mullis
4,754,065 A 6/1988 Levenson et al.
4,800,159 A 1/1989 Mullis et al.
5,034,506 A 7/1991 Summerton et al.
5,138,045 A 8/1992 Cook et al.
5,180,820 A 1/1993 Barde et al.
5,218,105 A 6/1993 Cook et al.
5,288,512 A 2/1994 Seiden
5,288,514 A 2/1994 Ellman
5,319,080 A 6/1994 Leumann
5,393,878 A 2/1995 Leumann
5,432,272 A 7/1995 Benner et al.
5,457,189 A 10/1995 Crooke et al.
5,459,255 A 10/1995 Cook et al.
5,474,796 A 12/1995 Brennan
5,491,084 A 2/1996 Chalfie et al.
5,506,337 A 4/1996 Summerton et al.
5,519,134 A 5/1996 Acevedo et al.
5,525,735 A 6/1996 Gallop et al.
5,539,083 A 7/1996 Cook et al.
5,549,974 A 8/1996 Holmes
5,569,588 A 10/1996 Ashby et al.
5,576,302 A 11/1996 Cook et al.
5,593,853 A 1/1997 Chen et al.
5,605,662 A 2/1997 Heller et al.
5,661,134 A 8/1997 Cook et al.
5,708,161 A 1/1998 Reese
5,739,119 A 4/1998 Galli et al.
5,739,311 A 4/1998 Lackey et al.
5,756,710 A 5/1998 Stein et al.
5,849,902 A 12/1998 Arrow et al.
5,891,725 A 4/1999 Soreq et al.
5,902,880 A 5/1999 Thompson (Continued)

FOREIGN PATENT DOCUMENTS

CA 2686933 4/2008
EP 335451 A3 3/1988

(Continued)

OTHER PUBLICATIONS

Nyce et al, WO 02/085308, Oct. 2002, partial document of pp. 1-198 and 819-862 (252 pages total).*

(Continued)

*Primary Examiner* — Ekaterina Poliakova-Georgantas

(74) *Attorney, Agent, or Firm* — CuRNA, Inc; Monte R. Browder

(57) ABSTRACT

The present invention relates to antisense oligonucleotides that modulate the expression of and/or function of Brain derived neurotrophic factor (BDNF), in particular, by targeting natural antisense polynucleotides of Brain derived neurotrophic factor (BDNF). The invention also relates to the identification of these antisense oligonecleotides and their use in treating diseases and disorders associated with the expression of BDNF.

15 Claims, 16 Drawing Sheets

Specification includes a Sequence Listing.

(56) References Cited

U.S. PATENT DOCUMENTS 5,908,779 A 6/1999 Carmichael et al.
5,965,721 A 10/1999 Cook et al.
5,985,663 A 11/1999 Bennett et al.
6,005,095 A 12/1999 Capaccioli et al.
6,013,639 A 1/2000 Peyman et al.
6,013,786 A 1/2000 Chen et al.
6,034,233 A 3/2000 Ecker et al.
6,100,090 A 8/2000 Monia et al.
6,140,492 A 10/2000 Morelli et al.
6,147,200 A 11/2000 Manoharan et al.
6,165,712 A 12/2000 Foulkes et al.
6,165,990 A 12/2000 Singh et al.
6,175,409 B1 1/2001 Nielsen et al.
6,221,587 B1 4/2001 Ecker et al.
6,239,265 B1 5/2001 Cook
6,242,589 B1 6/2001 Cook et al.
6,268,490 B1 7/2001 Imanishi et al.
6,303,374 B1 10/2001 Zhang et al.
6,307,040 B1 10/2001 Cook et al.
6,316,198 B1 11/2001 Skouv et al.
6,335,434 B1 1/2002 Guzaev et al.
6,376,541 B1 4/2002 Nixon et al.
6,403,566 B1 6/2002 Wang
6,444,464 B1 9/2002 Wyatt
6,451,991 B1 9/2002 Martin et al.
6,525,191 B1 2/2003 Ramassamy
6,528,262 B1 3/2003 Gilad et al.
6,528,631 B1 3/2003 Cook et al.
6,617,122 B1 9/2003 Hayden et al.
6,617,442 B1 9/2003 Crooke et al.
6,630,315 B1 10/2003 Miwa et al.
6,639,059 B1 10/2003 Kochkine et al.
6,656,730 B1 12/2003 Manoharan
6,667,337 B2 12/2003 Wilson
6,670,461 B1 12/2003 Wengel et al.
6,710,174 B2 3/2004 Bennett et al.
6,734,291 B2 5/2004 Kochkine et al.
6,762,169 B1 7/2004 Manoharan
6,794,499 B2 9/2004 Wengel et al.
6,833,361 B2 12/2004 Hong et al.
6,861,514 B2 3/2005 Cook et al.
6,867,294 B1 3/2005 Sanghvi et al.
6,936,467 B2 8/2005 Kmiec et al.
6,936,593 B1 8/2005 Agrawal et al.
6,977,295 B2 12/2005 Belotserkovskii et al.
6,986,988 B2 1/2006 Gilad et al.
7,034,133 B2 4/2006 Wengel et al.
7,034,145 B2 4/2006 Shen et al.
7,053,195 B1 5/2006 Goff
7,053,199 B2 5/2006 Imanishi et al.
7,053,207 B2 5/2006 Wengel
7,060,809 B2 6/2006 Wengel et al.
7,084,125 B2 8/2006 Wengel
7,087,589 B2 8/2006 Jacobson et al.
7,125,982 B1 10/2006 Frayne
7,144,995 B2 12/2006 Wise et al.
7,144,999 B2 12/2006 Ward et al.
7,148,204 B2 12/2006 Bennett et al.
7,153,954 B2 12/2006 Koch et al.
7,169,916 B2 1/2007 Krotz et al.
7,199,107 B2 4/2007 Dobie et al.
7,202,357 B2 4/2007 Crooke et al.
7,217,572 B2 5/2007 Ward et al.
7,220,549 B2 5/2007 Buzby
7,226,785 B2 6/2007 Kmiec et al.
7,229,974 B2 6/2007 Peyman et al.
7,229,976 B2 6/2007 Dobie et al.
7,235,534 B2 6/2007 Tauguay et al.
7,235,653 B2 6/2007 Bennett et al.
7,238,858 B2 7/2007 Marraccini et al.
7,276,599 B2 10/2007 Moore et al.
7,285,288 B1 10/2007 Tormo et al.
7,297,786 B2 11/2007 McCray et al.
7,314,923 B2 1/2008 Kaneko et al.
7,320,965 B2 1/2008 Sah et al.
7,321,828 B2 1/2008 Cowsert et al.
7,335,764 B2 2/2008 Crooke et al.
7,335,765 B2 2/2008 Kaneko et al.
7,339,051 B2 3/2008 Crooke et al.
7,371,833 B1 5/2008 Weiss
7,399,845 B2 7/2008 Seth et al.
7,402,434 B2 7/2008 Newman et al.
7,402,574 B2 7/2008 Iversen et al.
7,420,050 B2 9/2008 Park et al.
7,423,142 B2 9/2008 Vornlocher
7,425,545 B2 9/2008 Crooke et al.
7,427,675 B2 9/2008 Capaldi et al.
7,456,154 B2 11/2008 Soreq et al.
7,462,642 B2 12/2008 Wang et al.
7,468,431 B2 12/2008 Bhanot et al.
7,510,830 B2 3/2009 Baguley et al.
7,541,344 B2 6/2009 Bhat et al.
7,547,684 B2 6/2009 Seth et al.
7,569,575 B2 8/2009 Sorensen et al.
7,569,686 B1 8/2009 Bhat et al.
7,572,582 B2 8/2009 Wengel et al.
7,582,745 B2 9/2009 Sah et al.
7,585,893 B2 9/2009 Baguley et al.
7,589,190 B2 9/2009 Westergaard et al.
7,598,227 B2 10/2009 Crooke et al.
7,605,251 B2 10/2009 Tan et al.
7,622,453 B2 11/2009 Frieden et al.
7,662,948 B2 2/2010 Kurreck et al.
7,666,854 B2 2/2010 Seth et al.
7,674,895 B2 3/2010 Reich et al.
7,687,617 B2 3/2010 Thrue et al.
7,691,995 B2 4/2010 Zamore et al.
7,695,902 B2 4/2010 Crooke
7,696,345 B2 4/2010 Allerson et al.
7,709,456 B2 5/2010 Corey et al.
7,709,630 B2 5/2010 Gaarde et al.
7,713,738 B2 5/2010 Hansen et al.
7,718,629 B2 5/2010 Bamcrot et al.
7,723,508 B2 5/2010 Crooke et al.
7,732,422 B2 6/2010 Gleave et al.
7,732,590 B2 6/2010 Bhanot et al.
7,737,264 B2 6/2010 Thrue et al.
7,737,265 B2 6/2010 Akinc et al.
7,741,305 B2 6/2010 Crooke et al.
7,741,309 B2 6/2010 Hansen et al.
7,741,457 B2 6/2010 Seth et al.
7,745,609 B2 6/2010 Bennett et al.
7,749,978 B2 7/2010 Sah et al.
9,074,210 B2 7/2015 Collard et al.
2002/0193335 A1 12/2002 Hesson et al.
2003/0139359 A1 7/2003 Dobie
2003/0186920 A1 10/2003 Sirois
2003/0191075 A1 10/2003 Cook et al.
2003/0228618 A1 12/2003 Levanon et al.
2003/0233670 A1 12/2003 Edgerton et al.
2004/0006031 A1 1/2004 Dean et al.
2004/0033480 A1 2/2004 Wong
2004/0101858 A1 5/2004 Ward et al.
2004/0137423 A1 7/2004 Hayden et al.
2004/0138155 A1 7/2004 Baird et al.
2004/0175803 A1 9/2004 Meritet et al.
2004/0180336 A1 9/2004 Gilad et al.
2004/0254137 A1 12/2004 Ackermann et al.
2005/0009771 A1 1/2005 Levanon et al.
2005/0026160 A1 2/2005 Allerson et al.
2005/0113326 A1 5/2005 Siwkowski et al.
2005/0143357 A1 6/2005 Pousette et al.
2005/0153286 A1 7/2005 Clements
2005/0215504 A1 9/2005 Bennett et al.
2005/0222029 A1 10/2005 Bartel et al.
2005/0246794 A1* 11/2005 Khvorova ............ A61K 31/713 800/286
2005/0255487 A1* 11/2005 Khvorova ............ A61K 31/713 435/6.11
2006/0009410 A1 1/2006 Crooke et al.
2006/0142196 A1 6/2006 Klein et al.
2006/0178333 A1 8/2006 Soreq et al.
2007/0082848 A1 4/2007 Alitalo et al.
2007/0197459 A1 8/2007 Milner

(56) References Cited

U.S. PATENT DOCUMENTS

2007/0213274 A1 9/2007 Salonen
2007/0213292 A1 9/2007 Stoffel et al.
2007/0231816 A1 10/2007 Chaussabel et al.
2007/0243546 A1* 10/2007 Cao ...................... C12Q 1/6837 435/6.12
2007/0248590 A1 10/2007 Milne et al.
2008/0146788 A1 6/2008 Bhat et al.
2008/0221051 A1 9/2008 Becker et al.
2008/0293142 A1 11/2008 Liu et al.
2009/0191263 A1 7/2009 Reich et al.
2009/0192106 A1 7/2009 Dobie et al.
2009/0208479 A1 8/2009 Jaye et al.
2009/0258925 A1 10/2009 Wahlestedt
2009/0318536 A1 12/2009 Freier et al.
2009/0326041 A1 12/2009 Bhanot et al.
2010/0105760 A1 4/2010 Collard et al.

FOREIGN PATENT DOCUMENTS

EP 335451 A2 10/1989
WO WO-1984/03564 9/1984
WO WO-1991/19735 12/1991
WO WO-1992/00091 1/1992
WO WO-1992/08796 5/1992
WO WO-1993/20242 10/1993
WO WO-1994-026887 A1 11/1994
WO WO-1994/28143 12/1994
WO WO-1995-015373 A2 6/1995
WO WO-1995/22618 8/1995
WO WO-1995/25116 10/1995
WO WO-1995/35505 12/1995
WO WO-1996-027663 A2 9/1996
WO WO-1997-039120 A1 10/1997
WO 199801573 A1 1/1998
WO WO-1999-014226 A1 3/1999
WO WO-1999-039352 A1 8/1999
WO WO-2000-057837 A1 10/2000
WO WO-2000-061770 A2 10/2000
WO WO-0078341 A1 * 12/2000 ........... C12N 15/113
WO WO-2001-000669 A2 1/2001
WO WO-2001-21631 A2 3/2001
WO WO-2001-025488 A2 4/2001
WO WO-2001-051630 A1 7/2001
WO WO 0177384 A2 * 10/2001 ......... C07K 14/4703
WO WO-2002-062840 A1 8/2002
WO WO-2002-068688 A1 9/2002
WO 2002085309 A2 10/2002
WO WO-2004-016255 A1 2/2004
WO WO-2004-024079 A2 3/2004
WO WO-2004-030750 A1 4/2004
WO WO-2004-041838 A1 5/2004
WO WO-2004- 104161 A2 12/2004
WO WO-2005-045034 A2 5/2005
WO WO-2005-070136 A2 8/2005
WO WO-2005-079862 A1 9/2005
WO 2006042396 A1 4/2006
WO 2006072005 A2 7/2006
WO 2006072005 A3 7/2006
WO WO-2007-028065 A2 3/2007
WO WO-2007-071182 A1 6/2007
WO WO-2007-087113 A2 8/2007
WO WO-2007-138023 A1 12/2007
WO WO-2008-057556 A2 5/2008
WO WO-2008-066672 A2 6/2008
WO WO-2008-087561 A2 7/2008
WO WO-2010-002984 A1 1/2010
WO WO-2010-040571 A2 4/2010
WO WO-2010-054364 A1 5/2010
WO WO-2010-058227 A2 5/2010
WO 2010093904 A2 8/2010

OTHER PUBLICATIONS

Ausubel, Current Protocols in Molecular Biology vol. 1, 1994, 6.0.1-6.4.10.

Barak, et al., "A β-Arrestin/Green Fluorescent Protein Biosensor for Detecting G Protein-Coupled Receptor Activation," J. Biol. Chem. 272:27497-27500 (1997).

Barber, et al., "Delivery of membrane-impermeant fluorescent probes into living neural cell populations by lipotransfer," Neuroscience Letters 207:17-20 (1996).

Baum, "Solid-phase synthesis of benzodiazepines," C&EN News, Jan. 18, p. 33-34 (1993).

Bernstein, E., et al., "Role for a Bidentate Ribonuclease in the Initiation Step of RNA Interference," Nature 409:363-366 (2001).

Boutla, A., et al., "Short 5'-phosphorylated double-stranded RNAs induce RNA interference in *Drosophila*," Curr. Biol. 11:1776-1780 (2001).

Boyd-Kimball, et al., "Proteomic Identification of Proteins Specifically Oxidized by Intracerebral Injection of Amyloid β-Peptide (1-42) into Rat Brain: Implications for Alzheimer's Disease," Neuroscience 132, 313-324 (2005).

Brazma & Vilo, "Gene expression data analysis," FEBS Lett., 480:17-24 (2000).

Bright, et al., "Chapter 6. Fluorescence Ratio Imaging Microscopy," Methods in Cell Biology vol. 30, Taylor and Wang (eds) p. 157-192 (1989).

Bright, et al., "Delivery of Macromolecules Into Adherent Cells via Electroporation for Use in Fluorescence Spectroscopic Imaging and Metabolic Studies," Cytometry 24:226-233 (1996).

Bright, et al., "Fluorescence Ratio Imaging Microscopy: Temporal and Spatial Measurements of Cytoplasmic pH," J. Cell Biology 104:1019-1033 (1987).

Campbell, et al., "Phosphonmate Ester Synthesis Using a Modified Mitsunobu Condensation," J. Org. Chem. 59:658-660 (1994).

Caplen, N. J., et al., "Specific inhibition of gene expression by small double-stranded RNAs in invertebrate and vertebrate systems," PNAS Sci. USA 98:9742-9747 (2001).

Carninci, et al., "The transcriptional landscape of the mammalian genome," Science 309:1559-1563 (2005).

Carulli, et al., "High Throughput Analysis of Differential Gene Expression," J. Cell Biochem. Suppl., 3:286-296 (1998).

Celis, et al., "Gene expression profiling: monitoring transcription and translation products using DNA microarrays and proteomics," FEBS Lett., 480:2-16 (2000).

Chabala, J.C., "Solid-phase combinatorial chemistry and novel tagging methods for identifying leads," Curr Opin Biotechnol. 6:632-639 (1995).

Cech, J., "Ribozymes and Their Medical Implications," American. Med Assoc. 260:3030-3035 (1988).

Chen, et al., "Expression of ssDNA in Mammalian Cells," BioTechniques 34:167-171 (2003).

Chen, et al., "Analogous Organic Synthesis of Small-Compound Libraries: Validation of Combinatorial Chemistry in Small-Molecule Synthesis," J. Amer. Chem. Soc. 116:2661-2662 (1994).

Cheng, J. et al., "Transcriptional maps of 10 human chromosomes at 5-nucleotide resolution," Science 308:5725:1149-1154 (2005).

Cho, et al., "An Unnatural Biopolymer," Science 261:1303-1305 (1993).

Christiensen, N.K. et al., "A Novel Class of Oligonucleotide Analogues Containing 2'-O,3'-C-Linked [3.2.0]Bicycloarabinonucleoside Monomers: Synthesis, Thermal Affinity Studies, and Molecular Modeling," J. Am. Chem. Soc., 120:5458-5463 (1998).

Cubitt, et al. , "Understanding, improving and using green fluorescent proteins," Trends in Biochemical Science 20:448-455 (1995).

Curiel, D. T. et al., "Adenovirus enhancement of transferrin-polylysine-mediated gene delivery," PNAS 88:8850-8854 (1991).

Dai et al., "SIRT1 Interacts With p73 and Suppresses p73-Dependent Transcriptional Activity," J Cell Physiol 210(1):161-165 (2007).

(56) References Cited

OTHER PUBLICATIONS

Davidson, et al., "A model system for in vivo gene transfer into the central nervous system using an adenoviral vector," Nat. Genet 3:219-223 (1993).
Davis, et al., "Direct Gene Transfer into Skeletal Muscle in Vivo: Factors Affecting Efficiency of Transfer and Stability of Expression," Hum Gene Ther 4:151-159 (1993).
De Mesmaeker, et al., "Antisense Oligonucleotides," Acc. Chem. Res. 28:366-374 (1995).
Deng et al., "Small Interfering RNA Targeting the PINK1 Induces Apoptosis in Dopaminergic Cells SH-SYSY", Biochemical and Biophysical Research Communications, vol. 337, No. 4, pp. 1133-1138 (2005).
Dixon, et al., "Anthrax," New England J. Med. 341:815-826 (1999).
Dolle, "Discovery of Enzyme inhibitors through combinatorial chemistry," Mol Divers. 2:223-236 (1997).
Dykxhoorn, D., et al., "Determinants of Specific RNA Interference-Mediated Silencing of Human β-Globin Alleles Differing by a Single Nucleotide Polymorphism," PNAS, vol. 103, No. 15, pp. 5953-5958, (2006).
Eguchi, et al., "Antisense RNA," Annu Rev. Biochem 60:631-652 (1991).
Eichler, et al., "Generation and utilization of synthetic combinatorial libraries," Mol Med Today 1:174-180 (1995).
Eichler, et al., "Peptide Peptidomimetic and organic synthetic combinatorial libraries," Med Res Rev 15:481-496 (1995).
Espeseth, et al., "A genome wide analysis of ubiquitin ligases in APP processing identifies a novel regulator of BACE1 mRNA levels," Mol. Cell Neurosci. 33: 227-235 (2006).
Faghihi, M. & Wahlestedt, C., "RNA interference is not involved in natural antisense mediated regulation of gene expression in mammals," Genome Biol (2005), 7: R38.1-R38.9.
Fauchere, et al., "Peptide and nonpeptide lead discovery using robotically synthesized soluble libraries," Can J. Physiol Pharmacol 75:683-689 (1997).
Felgner and Holm, "Cationic Liposome-Mediated Transfection," Bethesda Res. Lab Focus, 11:2:21 (1989).
Fields, et al., "How many genes in the human genome?" Nature Genetics 7:345-346 (1994).
Freier & Altman, "The ups and downs of nucleic acid duplex stability: structure-stability studies on chemically-modified DNA:RNA duplexes," Nucl. Acid Res., 25:22:4429-4443 (1997).
Fuchs, et al., "Identification of Differentially Expressed Genes by Mutually Subtracted RNA Fingerprinting," Anal. Biochem., 286:91-98 (2000).
Gebeyehu, G., et al., "Novel biotinylated nucleotide-analogs for labeling and colorimetric detection of DNA," Nucl. Acids Res. 15:4513 (1987).
Geller, A.I. et al., "An HSV-1 Vector Expressing Tyrosine Hydroxylase Causes Production and Release of L-DOPA from Cultured Rat Striatal Cells," J. Neurochem 64:487-496 (1995).
Geller, A.I. et al., "Long-term increases in neurotransmitter release from neuronal cells expressing a constitutively active adenylate cyclase from a herpes simplex virus type 1 vector," PNAS U.S.A. :90:7603-7607 (1993).
Geller, A.I., et al., "Infection of cultured central nervous system neurons with a defective herpes simplex virus 1 vector results in stable expression of *Escherichia coli* β-galactosidase," PNAS USA 87:1149-1153 (1990).
GenBank Accession No. NM_000559, *Homo sapiens* Hemoglobin, Gamma A (HBG1), mRNA, (2008).
Giuliano, et al., "FLuorescent Protein Biosensors: Measurement of Molecular Dynamics in Living Cells," Ann. Rev. of Biophysics and Biomolecular Structure 24:405-434 (1995).
Giuliano, et al., "Light-Optical-Based Reagents for the Measurement and Manipulation of Ions, Metabolites, and Macromolecules in Living Cells," Methods in Neuroscience 27:1-16 (1995).
Giuliano, et al., "Determination of Intracellular pH of BALB/c-3T3 Cells Using the Fluorescence of Pyranine," Anal. Biochem 167:362-371 (1987).
Going & Gusterson, "Molecular Pathology and Future Developments," Eur. J. Cancer, 35:1895-1904 (1999).
Hagihara, et al., "Vinylogous Polypeptides: An Alternate Peptide Backbone," J. Amer. Chem. Soc. 114:6568-6571 (1992).
Haussecker, D., et al., "Dicer-Dependent Turnover of Intergenic from the Human β-Globin Gene Cluster," Molecular and Cellular Biology, vol. 25, No. 21, pp. 9724-9733, (2005).
Heller, et al., "Discovery and Analysis of Inflammatory Disease-Related Genes Using cDNA Microarrays," PNAS U.S.A. 94:2150-2155 (1997).
Herdewijn P., "Heterocyclic Modifications of Oligonucleotides and Antisense Technology," Antisense & Nucleic Acid Drug Dev., 10:297-310 (2000).
Hirschmann, et al., J. Amer. Chem. Soc., 114:9217-9218 (1992).
Hobbs-DeWitt, et al., "Diversomers: An approach to nonpeptide, nonoligomeric chemical diversity," Proc. Nat. Acad. Sci. USA 90;6909-6913 (1993).
Houghton AN, Gold JS, Blachere NE, Immunity against cancer: lessons learned from melanoma,. Curr Opin Immunol 13:134-140 (2001).
International Human Genome Sequencing Consortium "Finishing the euchromatic sequence of the human genome." Nature 431:7011:931-945 (2004).
Janda, K.D. "Tagged versus untagged libraries: Methods for the generation and screening of combinatorial chemical libraries," PNAS 91:10779-10785 (1994).
Janowski, et al., "Inhibiting gene expression at transcription start sites in chromosomal DNA with antigen RNAs," Nature Chemical Biology, 1(4):216-222 (2005).
Jungblut, et al., "Proteomics in human disease: Cancer, heart and infectious diseases," Electrophoresis 20:2100-2110 (1999).
Jurecic & Belmont, "Long-distance DD-PCR and cDNA microarrays," Curr. Opin. Microbiol., 3:316-321 (2000).
Kabanov, et al., "A new class of antivirals: antisense oligonucleotides combined with a hydrophobic substituent effectively inhibit influenza virus reproduction and synthesis of virus-specific proteins in MDCK cells," FEBS Lett. 259:327-330 (1990).
Kaplitt, M.G., et al., "Long-term gene expression and phenotypic correction using adeno-associated virus vectors in the mammalian brain," Nat. Genet. 8:148-154 (1994).
Kapranov, P. et al., "Examples of the complex architecture of the human transcriptome revealed by RACE and high-density tiling arrays," Genome Res 15:7:987-997 (2005).
Katayama, S. et al., "Antisense Transcription in the Mammalian Transcriptome," Science 309:1564-1566 (2005).
Kawahara & Nishikura, "Extensive adenosine-to-inosine editing detected in Alu repeats of antisense RNAs reveals scarcity of sense-antisense duplex formation," FEBS Lett 580:2301-2305 (2006).
Kay, et al., "Identification of enzyme inhibitors from phage-displayed combinatorial peptide libraries," Comb Chem High Throughput Screen 4:535-543 (2001).
Kenan, et al., "Exploring molecular diversity with combinatorial shape libraries," Trends Biochem Sci 19:57-64 (1994).
Kornberg, A., DNA Replication, W.H. Freeman & Co., San Francisco, pp. 75-77, (1980).
Larson, et al., "Rapid DNA Fingerprinting of Pathogens by Flow Cytometry," Cytometry, 2000, 41:203-208 (2000).
Larsson, et al., "High-Throughput Protein Expression of cDNA Products as a Tool in Functional Genomics," J. Biotechnology., 80:143-157 (2000).
Lebl, et al., "One-bead-one-structure combinatorial libraries," Biopolymers 37:177-198 (1995).
LeGal Lasalle et al., "An Adenovirus Vector for Gene Transfer into Neurons and Glia in teh Brain," Science 259:988-990 (1993).
Letsinger, et al., "Cholesteryl-conjugated oligonucleotides: Synthesis, Properties, and Activity as Inhibitors of Replication of Human Immunodeficiency Virus in Cell Culture," PNAS 86:6553-6556 (1989).
Li et al., "Control of APP processing and Aβ generation level by BACE1 enzymatic activity and transcription," Faseb J 20; 285-292 (2006).

(56) References Cited

OTHER PUBLICATIONS

Li, et al., J. Neurochem 89 1308-1312 (2004).
Liang, et al., "Parallel Synthesis and Screening of a Solid Phase Carbohydrate Library," Science 274:1520-1522 (1996).
Luther, "Role of endogenous antisense RNA in cardiac gene regulation," J. Mol. Med. 83:26-32 (2005).
Madden, et al., "Serial analysis of gene expression: from gene discovery to target identification," Drug Discov. Today 5:415-425 (2000).
Makalowska I, Lin CF, Makalowski W., "Overlapping genes in vertebrate genomes," Comput Biol. Chem 29:1:1-12 (2005).
Mannino and Gould-Fogerite, "Liposome Mediated Gene Transfer," BioTechniques 6:682-690 (1988).
Manoharan et al., "Lipidic Nucleic Acids," Tetrahedron Lett 36:3651-3654 (1995).
Manoharan, et al., "Chemical Modifications to Improve Uptake and Bioavailability of Antisense Oligonucleotides," Ann. N.Y. Acad. Scie 660:306-309 (1992).
Manoharan, et al., "Introduction of a Lipophilic Thioether in teh Minor Groove of Nucleic Acids for Antisense Applications," Bioorg. Med. Chem. Let 3:2765-2770 (1993).
Manoharan, et al., "Cholic Acid-Oligonucleotide Conjugates for Antisense Applications," Bioorg. Med. Chem. Let 4;1053 (1994).
Manoharan, et al., "Oligonucleotide Conjugates: Alteration of the Pharmacokinetic Properties of Antisense Agents," Nucleosides & Nucleotides 14:969-973 (1995).
Manoharan, M., "2'-Carbohydrate modifications in antisense oligonucleotide therapy: importance of conformation, configurationj and conjugation," Biochemica et Biophysica Acta 1489:117-139 (1999).
Mattick, J. S. "RNA regulation: a new genetics?" Nat. Rev. Genet 5:4:316-323 (2004).
Maurer, R.A., "Cationic Liposome-Mediated Transfection of Primary Cultures of Rat Pituitary Cells," Bethesda Res. Lab. Focus 11:2:25 (1989).
McNeil in Methods in Cell Biology vol. 29, Taylor and Wang (eds.) p. 153-173 (1989).
Morelli et al., "The antisense bcl-2-IgH transcript is an optimal target for synthetic oligonucleotides," PNAS USA 94:8150-8155 (1997).
Nielsen, et al., "Sequence-Selective Recognition of DNA by Strand Displacement with a Thymine-Substituted Polyamide," Science 254:1497-1500 (1991).
Oberhauser, et al., "Effective incorporation of 2'-O-methyl-oligoribonucleotides into liposomes and enhanced cell association through modification with thiocholesterol," Nucl. Acids Res. 20:533-538 (1992).
Petit et al., "Wild-type PINK1 Prevents Basal and Induced Neuronal Apoptosis, a Protective Effect Abrogated by Parkinson Disease-Related Mutations", Journ. Biol. Chem., vol. 280, No. 40, pp. 34025-334032 (2005).
Prasanth, et al., "Regulating Gene Expression through RNA Nuclear Retention," Cell 123, 249-263 (2005).
Prashar & Weissman, "READS: A Method for Display of 3'-End Fragments of Restriction Enzyme-Digested cDNAs for Analysis of Differential Gene Expression," Methods Enzymol., 303:258-272 (1999).
Quantin, et al., "Adenovirus as an expression vector in muscle cells in vivo," PNAS 89:2581-2584 (1992).
Rosenfeld, et al., "In Vivo Transfer of the Human Cystic Fibrosis Transmembrane Conductance Regulator Gene to the Airway Epithelium," Cell, 68:143-155 (1992).
Rosok and Sioud, "Systematic identification of sense-antisense transcripts in mammalian cells," Nature Biotech. 22(1):104-108 (2004).
Saison-Behmoaras, et al., "Short modified antisense oligonucleotides directed against Ha-ras point mutation induce selective cleavage of the mRNA and inhibit T24 cells proliferation," EMBO J. 10:1111-1118 (1991).
Sanghvi, Y.S., in Crooke, S.T. and Lebleu, B., eds., Antisense Research and Applications, CRC Press, Boca Raton, 1993, p. 276-278.
Scheele et al., "The Human PINK1 Locus is Regulated and Vivo by a Non-Coding Natural Antisense RNA During Modulation of Mitochondrial Function", BMC Genomics, vol. 8, No. 1, p. 74 (2007).
Schena, et al., "Parallel human genome analysis: Microarray-based expression monitoring of 1000 genes," PNAS 93:10614-10619(1996).
Shea, et al., "Synthesis, hybridization properties and antiviral activity of lipid-oligodeoxynucleotide conjugates," Nucl. Acids Res 18:3777-3783 (1990).
Shen, T., et al., "Modification of Globin Gene Expression by RNA Targeting Strategies," Experimental Hematology, vol. 35, No. 8, pp. 1209-1218, (2007).
Shimomura, et al., "Semi-synthetic aequorin," J. of Biochemistry (Tokyo) 251:405-410 (1988).
Singer, et al., "Targeting BACE1 with siRNAs ameliorates Alzheimer disease neuropathology in a transgenic model," Nat Neurosci 8:1343-1349 (2005).
Southwick, et al., "Cyanine Dye Labeling Reagents-Carboxymethylindocyanine Succinimidyl Esters," Cytometry 11:418-430 (1990).
Stratford-Perricadet, et al., "Widespread Long-term Gene Transfer to Mouse Skeletal Muscles and Heart," J. Clin. Invest., 90:626-630 (1992).
Sullenger, et al., "Overexpression of TAR sequences Renders Cells Resistant to Human Immunodeficiency Virus Replication," Cell63:601-608 (1990).
Sun, et al., "Downregulation of Sirt1 by antisense oligonucleotides induces apoptosis and enhances radiations sensitization in A549 lung cancer cells," Lung Cancer 58(1):21-29 (2007).
Sutcliffe, et al., "TOGA: An automated parsing technology for analyzing expression of nearly all genes," PNAS, 97:1976-1981 (2000).
Sutton, et al., "TIGR Assembler: A New Tool for Assembling Large Shotgun Sequencing Projects," Genome Science & Tech., 1:9-19 (1995).
Svinarchuk, et al., "Inhibition of HIV proliferation in MT-4 cells by antisense oligonucleotide conjugated to lipophilic groups," Biochimie 75:49-54 (1993).
Tamagno, et al., "The various aggregation states of β-amyloid 1-42 mediate different effects on oxidative stress, neurodegeneration, and BACE-1 expression," Free Radic Biol Med 41:202-212 (2006).
Thakker, D.R., et al., "siRNA-mediated knockdown of the serotonin transporter in the adult mouse brain," Mol Psychiatry 10:782-789 (2005).
Thakker, et al., "Neurochemical and behavioral consequences of widespread gene knockdown in the adult mouse brain by using nonviral RNA interference," PNAS 101:17270-17275 (2004).
Thomas et al., "Intracellular pH Measurements in Ehrlich Ascites Tumor Cells Utilizing Spectroscopic Probes Generated in Situ," Biochemistry 18:2210-2218 (1979).
Thompson, et al., "Synthesis and Applications of Small Molecule Libraries" Chem Rev 96:555-600 (1996).
To, Ky, "Identification of Differential Gene Expressionm by High Throughput Analysis," Comb. Chem. High Throughput Screen 3:235-241 (2000).
Tong, et al., "Oxidative stress potentiates BACE1 gene expression," Neural Transm 112, 455-469 (2005).
Toulme, J.J., "New candidates for true antisense," Nature Biotechnology 19:17-18 (2001).
Tsien in Methods in Cell Biology vol. 30 Taylor and Wang (eds) p. 127-156 (1989).
Ulhman, E., "Recent advances in the medical chemistry of antisense oligonucleotide," Current Opinions in Drug Discovery & Development 3:203-213 (2000).
Van Den Eynde BJ, "T cell defined tumor antigens," Curr Opin Immunol 9:684-693 (1997).
Van Der Bruggen, et al., "Tumor-specific shared antigenic peptides recognized by human T cells," Immunol Rev188:51-64 (2002).

(56) References Cited

OTHER PUBLICATIONS

Vanhee-Brossolet and Vaquero, "Do natural antisense transcripts make sense in eukaryotes?" Gene 211:1-9 (1998).
Vaughn, et al., "Human Antibodies with Sub-nanomolar Affinities Isolated from a Large Non-immunized Phage Display Library," Nature Biotechnology, 14:3:309-314 (1996).
Velculescu, et al., "Serial Analysis of Gene Expression," Science 270:484-487 (1995).
Wahlestedt, "Natural antisense and noncoding RNA transcripts as potential drug targets," Drug Discovery Today 11 (11/12):503-508 (2006).
Wahlestedt, C., "Antisense oligonucleotide strategies in neuropharmacology," Trends Pharmacol Sci 15:2:42-46 (1994).
Walsh, et al., "The role of cell-derived oligomers of Aβ in Alzheimer's disease and avenues for therapeutic intervention," Biochem Soc Trans 33: 1087-1090 (2005).
Wang, B.B. et al., "Identification of a nuclear-specific cyclophilin which interacts with the proteinase inhibitor eglin c," Biochem J. 314 (Pt 1) 313-319 (1996).
Wiesenhofer, et al., "Glial cell line-derived neurotrophic factor (GDNP) is a proliferation factor for rat C6 glioma cells: evidence from antisense experiments," Antisense & Nucleic Acid Drug Development 10(5):311-321 (2000).
Xue, et al., "Hypoxia and reoxygenation increased BACE1 mRNA and protein levels in human neuroblastoma SH-SY5Y cells," Neurosci Lett 405,231-235 (2006).
Yamada, et al., "Endothelial Nitric-Oxide Synthase Antisense (NOS3AS) Gene Encodes an Autophagy-Related Protein (APG9-like2) Highly Expressed in Trophoblast" (2005).
Yang, et al., "Cellular and Humoral Immune Responses to Viral Antigens Create Barriers to Lung-Directed Gene Therapy with Recombinant Adenoviruses," J. Virol 69:2004-2015 (1995).
Yoshigai, et al., "Characterization of Natural Antisense Transcripts Expressed from Interleukin 1β-inducible Genes in Rat Hepatocytes," HOAJ Biology; 1-10 (2012).
EP Application No. 06850393.7 Examination Report dated Oct. 18, 2011.
International Search Report and Written Opinion for PCT Application No. PCT/US2010/033078 dated Jun. 29, 2011.
PCT/US2010/026119 Search Report and Written Opinion dated Feb. 7, 2011.
PCT/US2010/024079 Search Report and Written Opinion dated Jan. 31, 2011.
PCT/US2010/027394 Search Report and Written Opinion dated Nov. 5, 2010.
PCT/US96/10287 (WO97/000271) The Regents of the University of California Jan. 3, 1997.
Beiter, T., et al., "Antisense Transcription: A Critical Look in Both Directions" Cellular and Molecular Life Sciences, vol. 66, No. 1, pp. 94-112, (2009).
Cairns, M., et al., "Advances in non-coding RNA Profiling for Neurological", Frontiers in Genetics, vol. 4, No. 5, pp. 1-2, (2013).
Chan. J., et al., "Antisense Oligonucleotides: From Design to Therapeutic Application", Clinical and Experimental Pharmacology and Physiology, vol. 33, pp. 533-540, (2006).
Chang, Q., et al., "The Disease Progression of Mecp2 Mutant Mice Is Affected by the Level of BDNF Expression", Neuron, vol. 49, pp. 341-348, (2006).
Chikar, J. et al, "Over-Expression of BDNF by Adenovirus with Concurrent Electrical Stimulation Improves Cochlear Implant Thresholds and Survival of Auditory Neurons", Hearing Research, vol. 245, No, 1-2, pp. 24-34, (2008).
Gharami, K., et al., "Brain-Derived Neurotrophic Factor Over-Expression in the Forebrain Ameliorate Huntington's Disease Phenotypes in Mice", Journal of Neurochemistry, vol. 105, No. 2, pp. 369-379, (2008).
Guiard, B., et al., "Brian-Derived Neurotrophic Factor-Deficient Mice Exhibit a Hippocampal Hyperserotonergic Phenotype", International Journal of Neuropsychopharmacology, vol. 11, No. 1, pp. 79-92, (2008).
Han, J., et al., "Brain-Derived Neurotrophic Factor and Obesity in the WAGR Syndrome", The New England Journal of Medicine, vol. 359, No. 9, pp. 918-927, (2008).
Kandimalla, E., et al., "Design, Biochemical, Biophysical and Biological Properties of Cooperative Antisense Oligonucleotides", Nucleic Acids Research, vol. 23, No. 17, pp. 3578-3584, (1995).
Kesser, B., et al., "Gene Transfer in Human Vestibular Epithelia and the Prospects for Inner Ear Gene Therapy", Laryngoscope, vol. 118, No. 5, pp. 821-831, (2008).
Kiprianova, I., et al., "Brain-Derived Neurotrophic Factor Improves Long-Term Potentiation and Cognitive Functions after Transient Forebrain Ischemia in the Rat", Exprimental Neurology, No. 159, No. 2, pp. 511-519, (1999).
Liu, Q., et al., "Rodent BDNF Genes, Novel, Promoters, Novel Splice, Variants, and Regulation by Cocaine", Brain Research, vol. 1067, No. 1, pp. 1-12, (2006).
Liu, Q., et al., "Human Brain Derived Neurotrophic Factor (BDNF) Genes, Splicing Patterns, and Assessments of Associations with Substance Abuse and Parkinson's Disease", American Journal of Medical Genetics Part B: Neuropsychiatric Genetics, vol. 134B, No. 1, pp. 93-103, (2005).
Liu, Q., et al., "Differential Regulation of Sense and Antisense Human BDNF/BDNFOS Genes and Rodent BDNF Gene: Possible Roles in Alzheimer's Disease and Addictions", International Journal of Developmental Neuroscience, vol. 24, No. 8, pp. 559, (2006). Abstract.
Mellios, N., et al., "A Set of Differentially Expressed MiRNAs, Including miR-30a-5p, Act as Post-Transcriptional Inhibitors of BDNF in Prefrontal Cortex", Human Molecular Genetics, vol. 17, No. 19, pp. 3030-3042, (2008).
Murphy, D., et al., "Brain-Derived Neurotrophic Factor Mediates Estradiol—Induced Dendritic Spine Formation Hippocampal Neurons", Proceedings of the National Academy of Sciences of the United States of America, vol. 95, pp. 11412-11417, (1998).
Novikova, L., et al., "Effects of Neurotransplants and BDNF on the Survival and Regeneration of Injured Adult Spinal Motoneurons", European Journal of Neuroscience, vol. 9, No. 12, pp. 2774-2777, (1997).
Ploughman, M., et al., "Brain-Derived Neurotrophic Factor Contributes to Recovery of Skilled Reaching After Focal Ischemia in Rats", Stroke, vol. 40, pp. 1490-1495, (2009).
Pruunsild, P., et al., "Dissecting the Human BDNF Locus: Bidirectional Transcription, Complex Splicing, and Multiple Promoters", Genomics, vol. 90, No. 3, pp. 397-406, (2007).
Takebayashi, M., et al., "Decreased evels of Whole Blood Glial Cell Line-Derived Neurotrophic Factor (GDNF) in Remitted Patients with Mood Disorders", International Journal of Neuropsychopharmacology, vol. 9, No. 5, pp. 607-612, (2006).
Tamura, M., et al., "Influence of Brain-Derived Neurotrophic Factor on Pathfinding of Dentate Franule Cell Axons, The Hippocampal Mossy Fibers", Molecular Brain, vol. 2, No. 1, pp. 1-9, (2009).
Tsai, S., et al., "Brain-Derived Neurotrophic Factor: A Bridge Between Major Depression and Alzheimer's Disease?", vol. 61, No. 1, pp. 110-113, (2003).
Varela, M., et al., "Natural Antisense Makes Sense for Gene-Specific Activation in Brain", Molecular Therapy Nucleic Acids, vol. 1, pp. 1-3, (2012).
Wahlestedt, C., "Targeting Long Non-Coding RNA to Therapeutically Upregulate Gene Expression", Drug Discovery, vol. 12, pp. 433-446, (2013).
Zhang, Y., et al., "NATsDB: Natural Antisense Transcripts DataBase", Nucleic Acids Research, vol. 35, pp. D157-D161, (2007).

* cited by examiner

FIG.2

(SEQ ID NO.1)

>gi | 219842286 | ref | NM_170735| Homo sapiens brain-derived neurotrophic factor (BDNF), transcript variant 1, mRNA.

CACACACACACACACACACACAGAGAGAACATCTCTAGTAAAAAGAAAAGTTGAGCTTTCTTAGCTAGATGTGTGTATTAGC
CAGAAAAAGCCAAGGAGTGAAGGGTTTTAGAGAACTGGAGGAGATAAAGTGGAGTCTGCATATGGGAGGCATTTGAAAT
GGACTTAAATGTCTTTTTAATGCTGACTTTTTCAGTTTTCTCCTTACCAGACACATTGTTTTCATGACATTAGCCCCAGGCA
TAGACACATCATTAAAATGAACATGTCAAAAAATGATTTCTGTTTAGAAATAAGCAAAACATTTTCAGTTGTGACCACCC
AGGTGTAGAATAAAGAACAGTGGAATTGGGAGCCCTGAGTTCTAACATAAACTTTCTTCATGACATAAGGCAAGTCTTCT
ATGGCCTTTGGTTTCCTTACCTGTAAAACAGGATGGCTCAATGAAATTATCTTTCTTCTTTGCTATAATAGAGTATCTCTGT
GGGAAGAGGAAAAAAAAAGTCAATTTAAAGGCTCCTTATAGTTCCCCAACTGCTGTTTTATTGTGCTATTCATGCCTAGAC
ATCACATAGCTAGAAAGGCCCATCAGACCCCTCAGGCCACTGCTGTTCCTGTCACACATTCCTGCAAAGGACCATGTTGCT
AACTTGAAAAAAATTACTATTAATTACACTTGCAGTTGTTGCTTAGTAACATTTATGATTTTGTGTTTCTCGTGACAGCATG
AGCAGAGATCATTAAAAATTAAACTTACAAAGCTGCTAAAGTGGGAAGAAGGAGAACTTGAAGCCACAATTTTTGCACTT
GCTTAGAAGCCATCTAATCTCAGGTTATATGCTAGATCTTGGGGGCAAACACTGCATGTCTCTGGTTTATATTAAACCACA
TACAGCACACTACTGACACTGATTTGTGTCTGGTGCAGCTGGAGTTTATCACCAAGACATAAAAAAACCTTGACCCTGCA
GAATGGCCTGGAATTACAATCAGATGGGCCACATGGCATCCCGGTGAAAGAAAGCCCTAACCAGTTTTCTGTCTTGTTTCT
GCTTTCTCCCTACAGTTCCACCAGGTGAGAAGAGTGATGACCATCCTTTTCCTTACTATGGTTATTTCATACTTTGGTTGCA
TGAAGGCTGCCCCCATGAAAGAAGCAAACATCCGAGGACAAGGTGGCTTGGCCTACCCAGGTGTGCGGACCCATGGGAC
TCTGGAGAGCGTGAATGGGCCCAAGGCAGGTTCAAGAGGCTTGACATCATTGGCTGACACTTTCGAACACGTGATAGAAG
AGCTGTTGGATGAGGACCAGAAAGTTCGGCCCAATGAAGAAAACAATAAGGACGCAGACTTGTACACGTCCAGGGTGAT
GCTCAGTAGTCAAGTGCCTTTGGAGCCTCCTCTTCTCTTTCTGCTGGAGGAATACAAAAATTACCTAGATGCTGCAAACAT
GTCCATGAGGGTCCGGCGCCACTCTGACCCTGCCCGCCGAGGGGAGCTGAGCGTGTGTGACAGTATTAGTGAGTGGGTAA
CGGCGGCAGACAAAAAGACTGCAGTGGACATGTCGGGCGGGACGGTCACAGTCCTTGAAAAGGTCCCTGTATCAAAAGG
CCAACTGAAGCAATACTTCTACGAGACCAAGTGCAATCCCATGGGTTACACAAAAGAAGGCTGCAGGGGCATAGACAAA
AGGCATTGGAACTCCCAGTGCCGAACTACCCAGTCGTACGTGCGGGCCCTTACCATGGATAGCAAAAAGAGAATTGGCTG
GCGATTCATAAGGATAGACACTTCTTGTGTATGTACATTGACCATTAAAAGGGGAAGATAGTGGATTTATGTTGTATAGAT
TAGATTATATTGAGACAAAAATTATCTATTTGTATATATACATAACAGGGTAAATTATTCAGTTAAGAAAAAAAATAATTTT
ATGAACTGCATGTATAAATGAAGTTTATACAGTACAGTGGTTCTACAATCTATTTATTGGACATGTCCATGACCAGAAGGG
AAACAGTCATTTGCGCACAACTTAAAAAGTCTGCATTACATTCCTTGATAATGTTGTGGTTTGTTGCCGTTGCCAAGAACT
GAAAACATAAAAAGTTAAAAAAAATAATAAATTGCATGCTGCTTTAATTGTGAATTGATAATAAACTGTCCTCTTTCAGA
AAACAGAAAAAAACACACACACACACAACAAAAATTTGAACCAAAACATTCCGTTTACATTTTAGACAGTAAGTATCTTC
GTTCTTGTTAGTACTATATCTGTTTTACTGCTTTTAACTTCTGATAGCGTTGGAATTAAAACAATGTCAAGGTGCTGTTGTC
ATTGCTTTACTGGCTTAGGGGATGGGGGATGGGGGGTATATTTTTGTTTGTTTTGTGTTTTTTTTTCGTTTGTTTGTTTTGTT
TTTTAGTTCCCACAGGGAGTAGAGATGGGGAAAGAATTCCTACAATATATATTCTGGCTGATAAAAGATACATTTGTATGT
TGTGAAGATGTTTGCAATATCGATCAGATGACTAGAAAGTGAATAAAAATTAAGGCAACTGAACAAAAAAATGCTCACA
CTCCACATCCCGTGATGCACCTCCCAGGCCCCGCTCATTCTTTGGGCGTTGGTCAGAGTAAGCTGCTTTTGACGGAAGGAC
CTATGTTTGCTCAGAACACATTCTTTCCCCCCCTCCCCCTCTGGTCTCCTCTTTGTTTTGTTTTAAGGAAGAAAAATCAGTT
GCGCGTTCTGAAATATTTTACCACTGCTGTGAACAAGTGAACACATTGTGTCACATCATGACACTCGTATAAGCATGGAG
AACAGTGATTTTTTTTTAGAACAGAAAACAACAAAAAATAACCCCAAAATGAAGATTATTTTTTATGAGGAGTGAACATT
TGGGTAAATCATGGCTAAGCTTAAAAAAAACTCATGGTGAGGCTTAACAATGTCTTGTAAGCAAAAGGTAGAGCCCTGTA
TCAACCCAGAAACACCTAGATCAGAACAGGAATCCACATTGCCAGTGACATGAGACTGAACAGCCAAATGGAGGCTATG
TGGAGTTGGCATTGCATTTACCGGCAGTGCGGGAGGAATTTCTGAGTGGCCATCCCAAGGTCTAGGTGGAGGTGGGGCAT
GGTATTTGAGACATTCCAAAACGAAGGCCTCTGAAGGACCCTTCAGAGGTGGCTCTGGAATGACATGTGTCAAGCTGCTT
GGACCTCGTGCTTTAAGTGCCTACATTATCTAACTGTGCTCAAGAGGTTCTCGACTGGAGGACCACACTCAAGCCGACTTA
TGCCCACCATCCCACCTCTGGATAATTTTGCATAAAATTGGATTAGCCTGGAGCAGGTTGGGAGCCAAATGTGGCATTTGT
GATCATGAGATTGATGCAATGAGATAGAAGATGTTTGCTACCTGAACACTTATTGCTTTGAAACTAGACTTGAGGAAACC
AGGGTTTATCTTTTGAGAACTTTTGGTAAGGGAAAAGGGAACAGGAAAAGAAACCCCAAACTCAGGCCGAATGATCAAG
GGGACCCATAGGAAATCTTGTCCAGAGACAAGACTTCGGGAAGGTGTCTGGACATTCAGAACACCAAGACTTGAAGGTG

FIG.2 (Continued)

CCTTGCTCAATGGAAGAGGCCAGGACAGAGCTGACAAAATTTTGCTCCCCAGTGAAGGCCACAGCAACCTTCTGCCCATC
CTGTCTGTTCATGGAGAGGGTCCCTGCCTCACCTCTGCCATTTTGGGTTAGGAGAAGTCAAGTTGGGAGCCTGAAATAGTG
GTTCTTGGAAAAATGGATCCCCAGTGAAAACTAGAGCTCTAAGCCCATTCAGCCCATTTCACACCTGAAAATGTTAGTGA
TCACCACTTGGACCAGCATCCTTAAGTATCAGAAAGCCCCAAGCAATTGCTGCATCTTAGTAGGGTGAGGGATAAGCAAA
AGAGGATGTTCACCATAACCCAGGAATGAAGATACCATCAGCAAAGAATTTCAATTTGTTCAGTCTTTCATTTAGAGCTA
GTCTTTCACAGTACCATCTGAATACCTCTTTGAAAGAAGGAAGACTTTACGTAGTGTAGATTTGTTTTGTGTTGTTTGAAA
ATATTATCTTTGTAATTATTTTTAATATGTAAGGAATGCTTGGAATATCTGCTATATGTCAACTTTATGCAGCTTCCTTTTG
AGGGACAAATTTAAAACAAACAACCCCCCATCACAAACTTAAAGGATTGCAAGGGCCAGATCTGTTAAGTGGTTTCATAG
GAGACACATCCAGCAATTGTGTGGTCAGTGGCTCTTTTACCCAATAAGATACATCACAGTCACATGCTTGATGGTTTATGT
TGACCTAAGATTTATTTTGTTAAAATCTCTCTCTGTTGTGTTCGTTCTTGTTCTGTTTTGTTTTGTTTTTTAAAGTCTTGCTGT
GGTCTCTTTGTGGCAGAAGTGTTTCATGCATGGCAGCAGGCCTGTTGCTTTTTTATGGCGATTCCCATTGAAAATGTAAGT
AAATGTCTGTGGCCTTGTTCTCTCTATGGTAAAGATATTATTCACCATGTAAAACAAAAAACAATATTTATTGTATTTTAGT
ATATTTATATAATTATGTTATTGAAAAAAATTGGCATTAAAACTTAACCGCATCAGAACCTATTGTAAATACAAGTTCTAT
TTAAGTGTACTAATTAACATATAATATATGTTTTAAATATAGAATTTTTAATGTTTTTAAATATATTTTCAAAGTACATAAA
A

(SEQ ID NO.11)

>hg 18_knownGene_uc009yjg. 1 range=chr11: 27633018-27679176 5' pad=0 3' pad=0 strand=
- repeatMasking =none GTAAACCAATAGCCCCCATGCTCTGTGCGATTTCATTGTGTGCTCGCGTTCGCAAGCTCCGTAGTGCAGGAAGGTGCGGG
AAGGTGTGTCTGTGGCCCGGGAAACGCACGCCCTCTCCCAGAGAACTTGGGTGCTGGGATGGGGAGGAAGGGGAGAGTT
GAAAGCTAGGGGAGCGAGACCTCGGGGCGTGCGATTCTCACTCGCTCCCTCCCGCCCCAGCGCCCACAGCCGGGGTTTCT
GCAGAGGGCGCGGGACGCGGGGTTCCCCGGGGCTGAGGCTGGGGCTGGAACACCCCTCGAAGCCGCGGGCGTCCTGTCC
AAGGCGCCCCAGGAGGGCGCAGGACTCGCAGGGCGATGTCGCGGGGCCCTAGGGGAGGAGGTGAGGACAGGCCCCGGG
GGAGCGGGGAGTTCCGGGCGCCCCTCGGTTCCCCGCGCGAGGAAAAGACGCGGCGTTCCCTTTAAGCGGCCGCCTCGAAC
GGGTATCGGTAGCGCGGGCGAGCGGGGAGCGGGGGGCGGGGGGCGGGGGGGGGGGGCGGCGCCGTTTGACCAATCGA
AGCTCAACCGAAGAGCTAAATAATGTCTGACCCGGGCGCAAGGCGCAGCCTGGAGCTCCGGGTCCCCGACGCTGCCGCC
GCCGCGCCCGGGCGCACCCGCCCGCTCGCTGTCCCGCGCACCCCGTAGCGCCTCGGGCTCCCGGGCCGGACAGAGGAGCC
AGCCCGGTGCGCCCCTCCACCTCCTGCTCGGGGGGCTTTAATGAGACACCCACCGCTGCTGTGGGGCCGGCGGGGAGCAG
CACCGCGACGGGGACCGGGGCTGGGCGCTGGAGCCAGAATCGGAACCACGATGTGACTCCGCCGCCGGGGACCCGTGAG
GTTTGTGTGGACCCCGAGGTAGGCAAGCGCTGGGAATGGGGCTTGGTGCAGGAGCTGCCCGTCCGCGGGAGAGAGTTGA
CTGGGGGATCCCCCACCCCAAAGTTGTGGGACGAGGCCAGTCTCCTTCTTTCCTCCCCTCCGGTAGAAGGGACGATTTGGA
GTTACTCTTGGGGAGTTTTCTCCCCCATCCCACAACCCAGAAGGTCAGCCGGCACCACCAGGGAAAAAGGGACCCGGGGA
AGTCACGAAGTAGAGGAGGGAAGGCCTGGAGGAGACCCAGAGCTGCGTGATGGGAGCAAAGACGGCGACCCGGGGATC
CCTCGCAGCCCTCCCCCAGCCCAGGAGTAGTCGAGAGAGACTTAGGGGGCCAGAGCTGTCGAGGGTCCTGACTGAGGGG
AGGGTGCTGGGGCTAGGCTAGGAATCCTTCCAGGGGGTGGGTGGTCCCCGCGCCGACTTGCGGGGGGAGTGGGAGGGAA
GCTTGCGCCTTCAGCCCGCATCCCTTCCCCGGAGCTGCACACGGCTACCTGCTCCCCAGGAATTGAGACTGAAGTGGACTT
ACAAGTCCGAAGCCAATGTAGCTTGGAAAACTTGGGAGGCGGAATTCCTACCGCTGGGAACTGAAAGGGTCTGCGACAC
TCTCGGGCAGGCCGAACCCACATCTCTACCCATCCTGCGCCCCTCTTCTGAAGCGCCCTCCAGGGAAGTTAAGAGTTTTGA
CTTTCGGGGAGTGGTTGGGATGTACGTGGGGGATTCTTGACTCGGGTTAGTCTCTGGGGATGCAGAGCCGGGAAGAGGAA
TGGGTGAGTGAGTTACTCCTGGAAAGAAATAGCTGAGGATTGGGGGCTCTGTGCCTGACGGGCAAGAAGAAGGGGAGAT
TACAGACTAGGGGCATCCCTAAGGAAGAAGCCTCGGGGCTGCGAGGGTGAACTGGAGGATGCAGTGTTTGTGTGTTGGG
GGTAGAGCGGGGATGAGGGACCGGGGTGGAGGGGAGGCGAGGAGGAGGAGGGGACCCAGAGAACGAAGCTAGGGAAG
GTAGAGGGTGCCCTCTGCCGGCCATGCTGCCAAGAGCAGCTACTGGGGGCGGGAGGCTGGGGGTGGGGAAGTGGTAAAG
GAAGGTTTTGCGGGATCCCTTAGAGAGCTGGTAGGAGGGACTTGTTGAATGGTGCTGCTGACTCCAGCTCGGTGGGGCGT
GCGACTCGTCGTCGGTGGATTTTGACTCCTCGTTCTTGTTTGGCTTCTATGCAAGTTTTCCTCGCGCTGGGGGAGCTTTGAT
AAGCCTCGATTGGCGGTGTGTTAGGGCTTCTTGGATCTTATTTTAGGGTCCTCTAGTTATCCTGCACTTACTCCTTAATGTC
AGTAGCAACCAAAGAACATTTTCCGACAAGCACGCAGGAATGTTCTTGGCCAGAAGCAAAGAAAGGCATATTTCTGAGT
GTTTATTAATCCTCCTAGTAATCTTTTAAAGCAAAGTAATATGTAATTGGGAACGTTGATTTTCTAACTGCATATAAAAGG
CGACATGATATTAAATGAGACCCCTCCCTACTGACTCAATATCCTGCAAAATCTCTCTCTCCCCTTTATTATTATGGAAAA
ATCTATTTTTATATGAGTTTGTTGTAAGGTCAAAAGCCATTTTGGTCTTACAATTTGATATGTCTTTACATTTTAACTTATTG
AGGCATAATTACAGATTTAATTTGTATGAACGTGTGTGCCTTCAATGCTTATCTCATGCAACATAATTTTTAGGTTGGAGA
TTTCTGATGTTATGGCATGTAGCGTTTCAAGGCATTACACATAATAGGTAACATAGCATGTTGAAATTACACCACAAAGTT

FIG.2 (Continued)

TTGACCCTGGGAACAGCACCTTTTAAAAACAATCACTAAACTCCTGTTCCTGTTTTCTGATTTTGCAAATGCCTTGCTTAAG
ACTTTTTTTTTTTTTTTTTTTTTTTTTTTTTTGGGAAATTTACCTCTGGGTTAGCAGGAGAGGTAAAAAAAAGGAAAGAGAC
ACTTGTTGAAATGTAACCATAACCTTTACTGGAATTTAAAACATGTTGGTCACCATTACTGGAATTCCAGGGCCATAAAGT
CGTTGTCTTTTTTTTCTCTACTTCATTTTGTAAAATGTGATAAATGTTGGTAAATATAGACCAGTAGTAAGTATTATGACA
CTAAAAGCATTATGTATGTGGAACTATTTTAAGTTATTACAGAACATTTTCTATTTATAAATGATATAAGCAGAAAGAAAT
GATTTCCAGATAAACAAGGCTTACGTACATGTTTTGAAGCATTAGAACATTGCAGACACTCTTAGACATCACATTTTTTAA
AGCAAAATAACAGTAATTTTTCACATACCTTTGGAGCCTTTCATAGCCCATTCAGAGCTGAGTTAGTAGCTGGAAGTTTCC
TTTATTTTAAGGTGATATTTTAAAACCATTTAACATGTATAGTAGGTCAACATTGGTGCATCCAGAAAATGAAGCATTTAG
GAAATCTGTTTCAGTGTCTTTTCAATGTGTGTAACTTTTACTTGCAAACCAATGGAACCAAGAAAGTCATCATTTGCCTAA
AATGCAGTCATCACCTCAAATGATTCATTTATACTATGTGAGTTAATTGCCTTCATCTCATTAATGGCCAAGGAGGGAAGG
GAGGTCCTGGGGTATTTCTTGTTCATTTTGACTCACCAGGAGGGAAAATCCTGTAAAAAAAGAAATGCAAATTTCTAAAA
TCCTGGCTCAAAGTCCGTGGGTTTCCTGTTTAAAAGGGGCGCCATGAAAATGTAAGCTATTCCCTTTTTCCTGGAATCTTT
AAGAGTCCCAGCTTTTCAATAGTCAAAATGTAGATGATTGATATCATTTCTTATATGAATAGCACTGGTTTGTAGTTCAGC
ACGCACAGTGAGCTGGGCACGCCCACCTGATAGTATAGCAGAGAACTTGTTTACATTCTTTTTACATTCATCTTCTAAAAC
CTGGGGTGCTCTCTCTCTCTCTCTCTCTCTCTCTCTCTCTGTGTGTGTGTGTGTGTGTGTGTGCGTGCACGTGCGCGTGTGTGTA
GAGGGGGAGAGAGAGAGAGAGAGAGAACTGTGAACTGTGAAATATAACACAGCCAGCAGCTTTGGGTCTCAATCGTAGACT
TACTCTTAAGGAAATTTACAGAATGGAAAGGTCATGTTCAAGTAGTTTATTAACATTTTGAGATGTAGGAAATTAATCCCG
GAGTACAGAAGAACAATTTCAGACTTCCTGAATAAAAACAGACAGCATAGAGAGTGGATGATAGCTAAACTCTGAATAT
CTTTTGAGAAGAAAGGCACTCCCATTTCAGGTGCCCATAATATGGATTTGATTTTAGTGATTAAAACATTAATTTTCAACT
TGCATCTCCCTGTGTGGAAGAGTTCAATTTGTGTGAGGGGTCTCGCCTATCCAACAAAAGTGAATATGTCCCTTTTATAGG
GTAATTGCTAACTTGTCTCAACTTGTTTTCAAACAATTGTTATAGAGCACTCAGTTTCCACTAATTGCAAAATTGTTGCTTA
ATTGAAGGACTCTCAGCCATCTAGTGCAGCCATTCAGCCACTGGCAGGCTCTGTGATCTCAAACTGTGAATTGCATTTTAA
AGAGGAATCGAGGAGAGAATTCTGTGGAATTCTAGGTTTTAAGTGCTGGCTGTTGTTCAATGGAAGAGGAAATCATTTGA
ACAAGAATCGCATCAAGTTGTGTTGTGATAAATTTTTCTTTATTAGGATGAATAACATGCACAGATGAGCTTCAAAAGTGA
ATGAGCAAACTTACTGGTTACACTCTGCATCCATTTACTCTGTTTAGTATGGAGTAATGTTAGGCAATAAATGATGCTGGC
AAATGAAATCCGTATGTTATTTGCATGTGGTATTTAAACCTAGGAAACATAGAGTGGCTTTGGTATTTGTAGGCTTAGTCA
TGTGTGTCCTAAACGTCCTCTTAAACTTCTACTTAAGGCATAGAATTATTTAATCCTAAATAATTTTATACTTAAGTGCCTC
ACTGGATTTCCAGAATATTTACACTGTAAAGATTTAGAAAGGTCATGAACCCAATTATTGACTATATGGAATCATTATTGA
TGGCAGATGCAAAATGGAGCTCACTAATGTACTGACATTGAAAACCTTTTGCAGGGGAGAGGAGGGGGAGTGGTAAATG
TGTGTGTTCTTTAAGTGGAACAGGAAGGTATTCTCTTTTCTGTAGAAAAATTTGAGTATCTGGTCAGATAAGTGTGGAAGC
TTTCATTTAAATTAAGTATTTAAGTTCAAGTAGAAGCTCTAGGGCACTTATCCTCTTGATGAGACAAATCTTATCAAATAT
ACTAGATGCTAAGAAGTGGCTCATTGCCCTGATGTCTCATTTATAGATTGATGTTTGAGGATGGGTTGCATTAAGTGAGTT
AGGGGGCTGAGTGTGGGACAGGAGAACGATTGGAAGGAAGCAAAGTAAATTTACAAGCTTTAGTGACAGCCATAATAAA
GTAAAAGTTTATTTCCAGAGAGCCTAGAGAGTAAGGAACGTTATATAGTTTTCCCCAAAGGTTCACTTGAAAGAACTTTTC
ATTGGTTGTCATGGTAGTAATGTCCTGATTTTGAAATCTCCCAGAACCTAGTAGCTCTTAAACATGCTTTCATCTTGGTTCC
TTTGGTCTGACGGAAACTTTATGACGACCCTCTGTGTTTTTGACATGCCTCTGCATTTTTGGAGAGAGGAGGTCAGGCAAG
GGAGGATTTCTTAAAACTAAGACAGTATAGTAAGGAAACATAAAATTATATGATAAAAAATCACTGAACTTCAAATTGAC
TTACTGAAATAAAACCTAGAAGGCAACCTGTCGTTTAATTACAACTAGCTTGTATAAAATTAAAATTTATAAAATGGGAA
TTCAAAGAAAATAAACGGGCAGTTCCAAGTAATTTAAGCAACTCACCAAAAATTGAAGTAATAGTGCCACCTAGAGAAC
AAAATCACCAGCTTTACTAGCCAAATGGCTTATTTCCATATGAACCATTTTTCCAACGCTACAGTTACTAGGATTTCCTTGT
TACCATATTCAGATCTTGTGAGTGTGTATGGGGGTGGGGGTTGCATGTGGAATTACAGATGAAATTTTAAAACAAGCAGA
TCCACAATTTGATATATGCACTAAATCCTTTTAACGTTGTAATGTAGCCAAATGTAGAATAGCATGCCAGGAATCAACGGC
TAGCATCCTTTTTAACATTTATTATTTTCATGGATATGTACCAAACCGAACCATTGAGTATAAAGGTTCTGATTTTATTTAT
TTGCTACAGGCAATTCATTATACTTTCTGAGATACAATAACACCAAATAATTTGAGTAGAGAGACCTTTAAGAATGTTTTC
GATTTATGATCTACCTTTAACTTTAATGTACTCAGAAGATGTGAGAATAAAATAAAGTCAAATATAAGCAAGATTTTAAA
CACACACACAAAAAACAAACAAACAAGAAAAAGGAAGAAAATTATAAGGATTGCCTTAACCTTAGAATAGATGAAGGTA
TACATCTGAGCCAGCACCAAAAAAAAAAAAAAAAAAAAAGTTATGGAACCAGGAACCAATAATTACAAATTGACTTAAAAT
TCTTGGATGACAAAAATCTATATTTAGTTCATTTTTGCATGCGCCCACAACAGCATCCAAAACAGTTCTGGGGAGGCACTT
TGATAAATGTTGCTGAATGCACTAATAGATTGATTAATGGCTGCTTCAGATTATCACTAGTGATGTAGACAGAAACTTCAT
GAAAATGGTTTGTCTTGCTGGAAGAAAGGCAGAAATTGGAGGAAAAGGTTTAATAATATTTTTCCCCAGTACCTATTATA
AAAGTCATTTAGTTGGCTTAGTTCTATAATTTCTTATGTGTAATTTGATTCACTTATGAAATTGTGAATATATGAAATGTTA
AAGTTGATTTAGACAGCAACTATAAGCTTGTGGATTTTCTTTTAAATGTCTTCAAATTTTTAAATGCCAGTGGAGATGCCA
GCGACTGTGCTTCAGGGAGTAGAATATAGTATATCTTAAATTTGTGCCAATTTCTGGTAAGCAGAGAAAAAATTGCATGA
TAACCAAAGAAAGTCATATTGTTTGTGCTTTGTGTTATTCATGGAAGCAATCAGGTGCAGAAAACTTTCTTTTTCAGAAAA
AAAAAATTACTAAAATAAAGGTGCGTGTGTGTGTATGCACATATATCTAAAGGGAGAGAGGGAGAAGGAAACTTACTAA
ATAAAATTTTTGCCACATGGGATTTAGTCTAATCAGTCTTGGTTTTGGAGTTGCTATCATCAGTAGTTCCATTTTGTGATTC
TTTCTTTCTGCCTTCATGTGCCTTTGAAAACTGAAACTATGCCCAAATTAAAACAAGTTTTTCTGTCTTTTCACATGTTCAC
TTATTTCTTGAATGTGTTTTTAAACACAGACAAACTTCTTTTACATCATGTAGAATCTGAAGGTCGAGAAATTTGCAGTCA

FIG.2 (Continued)

TTTTGCTGGAGAGAGATGCTTGGCGGAGTCCCAGGCCACATTCCTAGGCCAAACTCTCGAAGGTATTCCTCTTATGCAACA
TTGGGAAAATACATCCAGCACCGACATGTTGGCTGATAATGTGTCTGAAGGCACAGACGATATGCTTATCATATGAAACA
TAAAGCCAGCAGATATTGCAGACATTCTGTTGAATGATAGAATCTGGATCATTTACATTTACTTAAATGTAAAATACTATG
ATTAAGTACAAAAAAATCAATTTAGGAGAGAATAGAGAGTTGCGGGCACGGTTTTAGGGGATGACTTATCAGCAGATTGT
AGAAAGGAAGCTTGAATGTTTTAAATTAACTGCAAGTTCAGTATAAGCCAGTGGTGTGACAAGAGGCTGTTATCATAGCT
ACTGAAATTTTGGGCTGCACTGCTAGAAATATAATACTGAAATGGAGAAGCTAATAATTCTTCACTTTTTAAATAGACTGT
ATCTAGAATATTATCATCAGTTCAAGGAAATGAAATAAGTTGTTTTAGGTACATCATCGATAAATTAGTGTACATTCAAAT
CACTGTGACCAGGATGCATAGGGAATTTGAAAGCATTGCATGTGAGCAATGGTTGAGGGGACTTGGAATGCATGACTTAG
GGACAAGAAAACTTAGGCTGGAATGGCAAGTGGTTTTTGAATGTTGGGTTGAGAAGAATTCTAAAACTGTGAAGGATTAG
TAAAAATAACATTCAGATTGCTAATGCCTACTGTGGCTGGGAGATTAGAGTGTCAACATGTGTGATGTATTTTTGACATCC
TTATTTTGAGGATGGGCTTCAAAGATTTGACGAACTGTCATAAGTGTAATTTGTGTTGCTTCAGACAGCAGTTCTAGAACC
AATGATGTAAATTTAGATACTCTACATGGTAGTTAGAAAACTTTCCATTAATTTAATTTAGCAAATATTGAATGCTCACTG
CATACAGAGCACTTTATTAGAGGAATATATAATAAAGAAAAAAGAGGTCTGGTGTGGTGGCTCATGCCTGTAATCCCAGC
ACTCTGGGAGGCTGAGGTGGGAGGATCACTTGAGCCCAGGAGATCATTACGAGTCTGGACAACATAGCAAGACCCCATCT
TTACAAAAGACAAAAAAAATTATCCAAGCCTGGTGACAGGCACTTGTAGTCCCAGCTACTTGGGAGGCTGAGGCAGTAG
GATCGTTTGAGCCCAGGAGGTTGGGGCTGCAGTGAGCCGTGATTGTCCCACTGCTCTTCAGCCTGGGTGACAGAGTGAGA
CCCCGTTGGAGGGAAGGAAGGGAAGGAAGGAAGAAAGGTAGGAAGGCTGAAATGAAACCCTTTTAGAAATGACACTAA
AATGGGAGGTTGGAGTAAGGTATTTTCTGAAGTGCCTTTGTACTTGTTTTTTTCTAATGCATTGGCCATAAGTCTGCTCCTT
ATTTATAGTCCATAAACAATCCTAATGAGAACAGTTATATATTTCTGCCTTTGAATCATCTACTTGAAGTGTTTAGCATCAT
GAATTGAGTATCAGAAATCCCTCCCATTTCTTTGCAAAGCGCTGTATTTTACTTTTCCTTATTTGTATACAGATTCTCAAAA
TTGGCTATTTTTCCTTTGGGTTAGACAGAACAGAATGTCTGGAAAAAAAAGTTCTTATCAAATTCAGGTGCCCAAATTGCT
TAAGAAATTAACTTTTGAGGTTATATTTTTTTAGGGTTCAGTAGCTAAACTAAGAAAACTTCTCACCGTTCACCTTCACTTT
TGGAAACCACAAAATCTTCAGATATTACAGTTTTCCAAAGAGTTTCTCTTTTTAAATATAAACTAAAAGGAATTGACTCCT
CCCCCAACTCCCTCAGGCCTCAGCATGGATAGAGTTACTTTTTTTCTTTAATAATTTATTTATAACTTATTTTGCTCTTCTGT
AGAACAGCTGGAGATTAAGCAACATGGCCATGACATAAAATGCAAGTTAGACCATAAGATGAGCAGCCCACTCCAAGTA
TGAATGAGTACTTATTCTTTGTGATCTCTCATACTGCTTTTAGGTATTAATAGTGTCAGTCAGCAAAGCAAACAGTTTAAT
ATTTACATCTCCTTTAGGATATCATATAGTTTATAGTTTGTATGTGTTCTTGCGTGTATGTTTTCTTCTGTTTCAAATTCTTTT
TTCTTAAAGTAAGAATGTTATATGTAGCAAATGGTTCTTTCATTAATTCATTTGTTAATTCACCGTGCATTAATTGAGTGCC
CAGTGAGTGTCAGGCACTGGGCTACTTGGATTTCTTTTCCCTGTATTGATCCATATATCTTCAGGTGCTCCTTGATATGGCT
CTCCATTGACTCTCTCATATAAGGCTTTCATTACCTATTCACATACTCCCTCCCAAAGAGGACTGGTCCAAAAGTAAAATC
TTGAGCAAGTTCTCTGAGTTATTTCAGAACTTCTTGCCCCCAAACTGTATTTTTAATTATTGACTGGTAGCATTTTGGAATA
ACTTACCTCTCTTTTTTAAAGATTGAAGTTCTTTATCCTCTCTGATTTTCAGGTGTCAGTTTGTGTACAAATTGAGACAATA
AAAATGTTTGTTAGACATTTTCTTAAAGCATTTTGCTATGTGAGAATCTTTCATGAAGAACTCTTTTTAACAATGACTCTAT
AGCAGAAGCCACAGTAGAGGGAGAACTACTGAATCAAAGATGGTGTTTGAGTCTATGATTTTATGATGGATTTTTTTTTTT
TTTACATACAAGGATATGCATGGGTCTTTTAGTATTCAGGAATCTGTTCTTCACTTGACAGTATTTATAAATTGTGTGTTTC
CCCCTAAAAAAACTTAAATTGTGAGAATGCTTCCATTTACTAGAAGTTGGTTAATGATTATGCCAAATAAGGAAAATAAG
ACAGAAAAATCAGTTTAGTGAATACTATTTTGCCTTTAAATTTAGTAATTTAGTAACAGTATCTCTTTGGGGTTTACTAGA
AACCACTTTTTAATCCAATAGGTCTCTTTCATTGTGAAGTCAGGAGGTGATTTTGCTTAAATGTGTAGTATAGGAATCTAT
ATGTGGTGTTCAAGGATCATGTAAATATGCTGATATAATCGGAGCACAGTTTGGCATCATTAACTCAGAAATATTTAAACT
CTTGCTATACAACATGGAAGCAAACTTGTGCATAGTTTGTGTGTGTGTGTGTGTGTGAATCTCAAAAAAAGAAAAAAAATC
ACAGGATCAGGAAGTCGGAATAGGTCCCACTTTTCTTCTAGTACCAAACCTACAGCCATGTTCCTAGCCTTCTCTTTTACT
CCCAAGCAAGACAGACAGGCAAATGACCATCCTGCTGCCCATTTCTGTGTATATTCACTTGCATTGAGAGTTGTATTCACC
TGCTTGTTGAGAGTATTCACAAATGGTACCTGATAAAGTAGATACTTCTTTAAACATGTGAATTTTTTTGCATTGTATAATG
TTTAGAAATAATCATGTATAAATGGTTGAATATTAATACAGGATTGCCTTATCAAGTATTTTATTAATCATTAAAATGTGG
TGTCATTAATACAATTTATTTTAAGTGCTTTTCCTAAAATACCAGATTATTTTTCTGATTTTCACATCCCTGACAATGACTTT
CTTAAACTTGGTAGCCAGGAACAGAAAACCTAACACTGCATGTTCTCACTCATAAGTGGGAGCTGAACAGAGAGAACAC
ATGGACTCAGGGAGGGGAACCACACACACTGGGGCCTGGAGCAGGGGGCAGGGGAAGGGAGAGAGTGCGTCAGGACAA
ACAGACAAATAGCTAATGCATGCGAGCCTTAATACCTAGGTGATGGGTTGATAGGTGCAGCAAACCACCATGACACATAT
TTACCTATGTAACAAACCTGCACATTCTGCACATGTATCCCGGAACTTAAAGTAAAATAAAAAATAATAATAAAATAAAA
TAAACTTAGTAGCATCTATTGTTCCAGAGCCTGTAATTGCTCTTCAGGCAGTCTCACATAAAAACCTAGGAGAACCTTCAC
TGTCACTGTTCCATGAGGTGTTAGGAAAACTTGCTCTACTGCAGTGCCCCAGTAGGCATTGGTACTGAGACCAAAATTCAG
CTGGTTTGTTGTTACTACGATTCCTACGTGATTTCACTTGTCATGTAGACAAGATTGCACACTTCAATAATAATCTTGTCCA
AATGTGTGGTATTCCATACATTTTTAAAATGCATTCACATATCTCATTCCATTTGATCCTACAAATAACTCTATAAAAAAG
ATTGGCAGACATTATTTCTATATAACAGAGGAGGAAACTGGAGCTTAGAGAAGCTAAATAGCAATCCAAAATGCACAGCT
GTAGAACCAGAGCAAGGATGATAGCCCAGTGACTTCACCTAACCTAGTCCCCTTACCACCACTCCAGCTGTCTATAACCA
AAACCTGCAGTATTCAAGTAAGAAACCATATCTTGCCCTTGATGCATTAATGTGAGACCTGGAGCAGGAACAGGCTGATA
TTGTCACCCTGGCCTACTGTCCACCTTTGTCTCCAGCAGAGACTGGTACCCTTCTGTGTGCCAAGGAATAAAGTGGTAATG
GGAAGATTAAAAATGTTTTTTCCAAGGAGTTTTTTAATTTAATTTTTTTAAAAAAGAAAAAACTCTTAGAGGGAAAAATGA
ATATATGACTTTTGATGTATTGTTCCTTAGTAACTTAGTTATAATTTTACTTAAACCTGAGACTCTTGCTAAGTGAATGATT

FIG.2 (Continued)

AGAAATATTAGGTGGCTGGCCAGATGGCAAATAGGAACAGCTGCAGTCTGCAGCTCCCAGAGAGATCAATGCAGAAGGT
GGGTGATTTCTGCATTTCCAACTGAGGTACCGGGCTCATCTCATTGGGACTGGTTAGACAGTGGGTGCAGCCCATGGAGG
GTGAGCCAAAGCAGGGTGGAGCATTGCCTCACTCAGGAAGCGCAAGGGGTCAGGGGAACTCCCTCCCCTAGCCAAGGGA
AGCCCTGAGGGACTGTGCCATGAGGGACAGTGCTATCTGGCCCAGATACTACACATTTCCTACAGTCTTTGCAGCCGGCA
GACCAGGAGATTCCCTTGGGTGCCTACACCACCAGGGCCCTGGGTTTCAAGTACAAAACTGGGTGGCCATTTGGGCAGAC
ACCCAGTTAGCTGCAGGAGTTTTTTCTCATACCCCAGTGGCACCTGAAATTCCAGTGAGACAGAACCATTCACTCCCCCGG
AAAGGGGCTGAAGGCCAGGCAGCCAAGTGATCTAGCTCAGCAGATCCCACCCCCATGGAGCACGGCAAGGTAAGATCTG
CTGGTTTGAAATTCTCACTGCCAGCACAGCTGCCTGAAGTCAACCTGGGATGCTCCAGCTTGGTCGGGGGAGGGGCATCC
GCCATTACTGAGGCTTGAGTAGGCTGTTTTCCTCTCACAATGTAAACAAAGCCACTGGGAAGTTTGAACTGGGTGGAGCC
TACCACAGCTCAGCAAAGCCCCTGTAGCCAGATTGCCTCTCTAGATTCTCCCTCTCTGGGCAGGGCATCTGGGAAAGAAA
GGCAGCAGCCCCAGTCAGGGGCTTATAGATAAAACTCCCATCTCATGGGACAGAGCACCTGGGAGAGGGGGTGGCTGTG
GGCCCAGCTTCAGCAGACTTAAATGTTCTTTGCCTGTTGGCTGTGAAGAGAGCAGTGGATCTCCCAGCACAGCACTTGAG
CTCTGCTAAGGGACAGACTGCCTTCTTAAGCAGGTCCCTGACCCTCGTGATTCCTGAGTGGGAGACACCTCCCAGCAGGG
GTCGACAGACACTTCATACAGGAGAGCTCTGGCTGGCATCTGGTGGGTGCCCCTCTGGGACAAACCTTCCAGAGGAAGGA
ACAGGCAGCAGTCTTTGCTGTTCTGCAGCTTCTGCTGGTGATACCCAGGCAAACAGGGTCTGGAGTGGACCTCCACCAAA
TTCCAGCAGACCTGCAGCAGAGGGGCCTGACTGTTAGAAGGAAAACTAACAAACAGGAATAGCATCAACATCAACAAAA
AGGATGTCCACACGAAAACCCCGTACAAAGGTCGCCAACATCAAAGATCAAACATAGATAAATCCACAAGGATGAGGAA
AATCCAGCACAAAAAGGCTGAAAATTCCAAAAACCAGAATGCCTCTTCTCCTCCAAGGGAGCACAACTCTTTGCCAGCAA
GGGAACAAAACTGGATGGAGAATGAGTTTGATGAATTGACAGAAGTATGCTTCAGAAAGTGGGTAAAAACAGACTCCTC
CAAGCTAAAGGAGCATGCTCTAACCCAATGCAAAGAAGCTAAGAACCTTGAAAAAAGGTTGGAGGAATTGCTAACTAGA
ATAACTAGTTTAGAGAAGAACATAAATGACCTAATGGAGCTGAAAAACACAGCACGAGAACTCTGTGAAGCATACACAA
GCTTCAATAACTGAATCGATAAAGCAGAGGAAAGGATATCAGAGATTGAAGATCAATTTAATGAAATAAAGCATGAAGA
CAAGATTAGAGAAAAAAAGAATGAAAAGGAAGGAACAAAGCCTCCAAGAAATGTGGGACTATGTGAAAAGACCAAACC
TACATTTCATTGGTGTACCTGAAAGTGGCGGGGACAATGGAACCAAGTTGGAAAACACTCCTTAGGATATTATCCAGGAG
AACTTCCCCAAACTAGCAAGACAAGCCAACATTCAAATTCAGGAAATACAGAGAACACCACAAAGATACCCCTCAAGAA
GAGCAAACCCAAGACATGTAATTGTCAGATTCACCAAGGTTGAAATGCAGGAAAAAAAGTTAAGGGCAGCGAGAGAGAA
AGGTCGGGTTACCCAAAAAGGGAAGCCCATCAGACTAACAGTGGATCTCTCAGCAGAAACCCTACAAGCCTACAAGCCA
GAAGAGAGTGGGGGCCAATATTCAACATTCTTAAAGAAAAGAATTTTCAACCCAGAATTTCATATCCAGCCAACTAAGCT
TCAGAAGTGAAGTAGAAATAAAATCCTTTACAGACGAGCAAATGCTGAGAGATTTTGTCACCACCAGGCATGCCTTACAA
GAGCTCCTGAAGGAAGTACTAAATAAGGAAAGGAAAAACCGGTACCAGCCACTGCAGAAACATACCAAATTGTAAAGAC
CATTGAAACTATGAAGAAACTGCATCAACTAATGGGCAAAATAACCAGCTAACATCATAATGACAGGATCAAATTCACAC
ATAACAATATTAACCTTAAATATAAATGGGCTAAATGCCCCAATTAAAAGACCACAGACTGGCAAATTGGATAAAGAGTC
AAGACCCATCAGTGTGCTGTGTTCTGGAGACCCATCTCACATGCAAAGACACACATAGGCTGAAAATAAAGGGATGGAG
GAAGATCTACCAAGCAAATGGAAAGCAAAAAAAAAGCAGGGGTTGCAATCCTAGTCTCTGATAAAACAGACTTTAAACC
AACAAAGATCAAAAGAGACAAAGAAGGCCATTACATAATGATAAAGGGATCAATTCAACAAGAAGAGCTAACTATCCTA
AACATATATGCACCCAATACAGGAGCACCCAGATTCATAAAGCAAGTTCTTAGAGACCCACAAAGAGACCAAGACTCCC
ACACAATAATAGTGTGAGACTTTAACACCCCAATGTCAATATTAGGTCAACGAGACAGAAAATTAACAAGCATATTCAGG
ATTTGAACTCAGCTCTGGACCCAGTGGAACTAATAGACATCTACAGAACTCTCCACCCCATATCAACAGAATATACATTCT
TCTCAGCACCACATCACACTTATTCTAAAATTGACCACATAATTGGAAGTAAAACACTCCTCAGCAAATGCAAAAGAATG
GAAATCATAACAAACAGTCTCTCAGACCAAAGTGCAATTAAATTAGAACTCAGGATTAAGAAACTAACTCAAAACCATAC
AACTACAGTGGAAACTGAACAACCTGCTCCTGAATGACTACTGAGTAAATAACAAAAAGAAGGCAGAAATAAATACATT
ATTTGAGACCAATGAGAATAAAGATACAACATACCAGAATCTCTGGGACACAGCTAAAACAGTGTTTAGGGGAAATTCAT
AGCAATAAATGCCCACAGGAGAAAGCAGGAAAGAGCTAAAATCAACACTCTAACATCACAATTAAAGGAACTAGAGAA
GCAAGAGCAAACACATTCAAAAGCTAGCAGAAGACAAGAAATAACTAAGATCAGAGCAGAACTGAAGGAGATTAGAGA
CACAAAAAACCCTTCAAAAAAATCAGTGAATCCAGAAGCTGGTTTTTTGAAAAGATTAACAAAATAGATAGAATGCTAGC
CAGATTGATAAAGAAGAAAAGAGAGAAGAATCAAATAGACGCAATAAAAGATGATAAAGAGGATATCACCACTGATCC
CACAAAAATACAATCTACCATCAGAGAACACTATAAACACCTCTATGCAAATAAACTAGAAAATCTAGAAGAAATGAAT
AAATTCCTGGACACATACACCCTCCTAAGACTAAAGGAAGAAGTCAAATTCCTGAATAGACCAATAATAAGTTCTGAAAT
CGAGGCAGTAATTAACAGCCTACCAACCAAAAAAAGCCCAGGACCAGACGGATTCACAGCTGAATTCTACCAGAAGTAC
AAAGAAGAGCTGGTACCATTCCTTCTGAAACTATTCCAATCAATAGAAAAGGAGGGAATCCTCCCTAACTCATTTTATGA
GTCCGGCATCATCCTGATACAAAAACCTGGCAGAGACACAGCAAAAAAATAAAATTGTAGGCCAATATCCCTGATGAAC
ATTGATGCAAAAATCTTCAATAAAAAACTGGTAAACTGAATCCAGCAGCACATCAAAAAGCTTATCTACCATGATAATTT
GGCTTCATCCCTGGGATGCAAGGCTGGTTCAACATATGCAAATCAATAAAGATAATCCATCACATAAAGAGAACCAATGA
CAAAAACCACATGATTATTTCAATAGATGCAGAAAAGGCCTTTCATAAAATTCAACAGCCCTTCATGCTAAAAACTCTCA
ATAAACTAGGTATTGATGGAACATATCTCAAAATAATAAGAGCTATTTATGAGAAACCCACAGCCAATATCATACTGAAT
GGGCAAAAGCTGGAAGCATTCATTTGAAAACCGGCACAAAACAAGGATGCCCTCTGTCACCACTCCTATTCAACATAGTA
TTGGACGTTCTAGCCAGGGCAATCAGGCAATAGAAAGAAATAAAGCATATTCAAATAGGAAGAGAGGAAGTCAAATTGT
CTCTGTTTGCAGATGACATGATTGTATATTTAGAAAACCCCATCATCTCAGCCCAAAATCTCCTTAAGCTGATAAGCAACT
TCAGCAAAGTCTCAGGATACAAAATCAATGTGCAAAAATCACGAGCATTCCTATACACCAATAATGACAAACAGCCAAGT

FIG.2 (Continued)

CATGAGTGAACTCCCATTCACAATTGCTACAAAGAGAATAAAATGCCTAGGAATACAACTTACAAGGGATGTGAAGGAC
CTCTTTAAAGAGAACTACAAACCACTGCTCAATGAAATAAGAGAGGACACAAACAAATGGAAGAACATTCCATTCTCATG
GATAGGAAGAATCAATATCGTGAAAATGGCCATACTGCCCAAAGTAATTTATAGATCCAATGCTATCCCCATCAAGCTAC
CATTGACTTTCTTCATAGAATTAGAAAAAACTACTTTAAATTTCATATGGAACCAAAAAACAGCCCGTATAGCCAAGACA
ATCCTAAGCAAAATGAACAAGCTGGAGGCATCATGCTACCTGACTTCAAACTATACTACAAGGCTACAGTAACCAAAACA
TCATGGTACTGGTACATAAACAGATAGATAGACCAATGGAACAGAACAGAGCCTCAGAAATAACGCCACACATCTACAA
CCATCTGATCTTTGACAAACATGACAAAAACAAGCAATGCAGAAAGGATTCCCTATTTAATAAATGGTGTCGGGAAAACT
GGCTAGCCATTTGCAGAAAACTGAAACTGGACCCCTTCCTTACACGTTATACAAAAATTAACTCAAGATGGATTAAAGAC
TTAAACATAAAACATAAAACCATAAAAACCCTAGAAGAAAACCTAGGCAATACCATTCAGGACATAGGCATGGCAAAGA
CTTCATGACTAAAATACCAAAAGCAATGGCAACAAAAGCCAAAATTGACAAATGGGATCTAATTAAACTAAAGAGCTTCT
GCACAGCAAAAGAAACTAACATCAGAGTGAACAGGCAACCGACAGAATGGGTGAAATTTTTTGCAACGTATCCATCTGA
CAAAAGGCTAATATCCAGAATCTACAAGGAACCTAAACAAGTTTACAAGAAAAAAAACAACCCCATCAAAAAGTGGGCG
AAGGGTATGAACAGATGCTTCTCAAAAGAAGAAATTTATGCTGCCAACAAACATACGAAGAAAAGCTCATCATCACTGGT
CATTAGAGAAATGCAAATCAAAACCACAGTGAGATACCATCTTATGCCAGTTAGAATGGCGATCATTAAAAAGTCAGGA
AACAACAGATGCAGGAGAGGATGTAGAGAAATAGGAACACTTTTACACTGTTGGTGGGAGTGTAAATTAGTTCAACCATT
GTGGAAGACAGTGTGGTGATTCCTCAAGGATCTAGAACCAGAAATATCTTTTGACCCAGCCATCCCATTACTGGGTATAT
ACTCAAAGGATTATAAATCATGCTACTATAAAGACACATGCACATGTATGTTTATTGTGGCACTATTCACAATAGCAAAG
ACTTGGAACCAATCCGAATGCCCATCAATGATAGACTGGATAAAGAAAATGTGACACACATACACCATGGAATACTATGC
AGCCATAAAAAAGGATGAGTTCATGTCCTTTGCAGGGACATGGATGAAGCTGGAAACCATCATTCTTGGCAAGGTAACAC
AGGAACAGAAAACCAAACACCACATGTTCTCACTCATAAGTGGGAGTTGAACAGTGAGAACACATGGACACTGGGAGGA
GAACATCACACACTGGGGCCTGTCAGGGTGTAGGAGGCTAGGGGAGGGATAGCATTAGGAGAAATACCTAATGTAGATG
ACAAGTTGATGAGTGCAGCAAACCACCATGGCATCTGTATACCTAGGTAACAAACCTGCACGTTCTGCACATGTACCCCA
GAACTTAAAAGTATTATTATTATTATTATAATAATAATAATAAAAGAAATACAATAAAATAGAATGCAGCATACAGCAGT
GATTCTCAAACACATTCAGCATCAGAATTACCCTTGAATCTTTAAAATATATATACATATGAGATCTTAGTCTCCAAGATT
TGTAAGTTTGGTATTGGGTCCCTGGGCCTATGTTGGGTTTAGAAACTTCTACAGATGGTTTGGATGTATGGGACAGTTTAA
GAATCGCTGAACTAAAATCAAATAAACTGAATATCCTGTGATTTAGAGAGACTTATCGTTTATTTCACTATCCAAGTACTT
GCATTAGAGCGTGGCTAGAAGGGATTTGCAGCCTTGTAAATAATCAGAAATTCAGACATTTTGAGATGAGAGAACTGCTG
AAGATTTTATTCTGACTTGAAATAAATTTTCTAATTAGAAACTTCCAGGTGAGAGCAAAGGCCTGGAACAATATTCCTGAG
CCAGAGGAGGATCGAGTTTGACTCCAGGCCTAACACTTACTAGGTCTATGACCTTGGGTCAGTAATTTAAATTCTCTGTAT
CTCAACCTCTCAACAGGGTATTGGTAGGGATTAAATGTGTTAGTGTCTGTGAAGTGCTTAGAGCAGTGCTTGGCATAGTAA
ATGCTTAATGAATTTCAGCCACTGTTTTTATTTTTAGTACTTTCCAGCTCCCCCAAAAAGATACTTTTTTTAGACTTGTATTA
AGACAATAAAAAGTTTAATCAGCATGCTTCATACCTAAATATGCTTCACTTTATAGCAAAGTTTACAAGACTAAAACTGTT
TTGTTGTAATTCTCTGAGTCTCATGTGTTTATTAATGATTTTTTCTGCTGTTTATTCATCTGAATTCTACTCATTCTTCAAGA
CCTAGCTGGAATCCTGTTTCTAGAAAGACTCTTGCCCATAATAATAAACCTGCCCTATCTGAGTTCCTAGGTGGTCTGTAC
CTCATAATTTGGTAATTAATTGTATATGCACTTATATAACAAAACATTATTGTGTGTCTTTGCTGTATCAGATTCTAGGCTG
GAAGTTGTAGATATGATGTTTTTGTCTAGAAAAATGTTCTAGAATGTCCTACTCAGGACAGTCTGTTGACTTTAAAGACAC
ATTTCCTAAACAGACACTTCATGAGGCAGCCCCAGCCTGTACCTGTGTTCCTGGACCTGATGATCAAGTTTGATTTAAGCC
TCACCACTTACTAGCTCTGTGATTTTGGGCAAGTTACTTGAATTCTCTGTGTGTAGATAGAACAATGTTGAGGGAAATCCC
TTTCCCCCATCCTTGTGTTTCCACAAGGGAACTTGCTTCCTAATAAGTAACACTTTCAGGGGAATATTCTAGGCCCTTCTCT
TATCCCCATTACTTGTTCTTTCTGTGAAAAGAGGAGAGGTTAATCTGATGGATGAAATCCTTAATCTTTCATCTTCTGGACT
GTAGAGCCTGTGAACCAAAGCAATGGACCACTTGCACTGAAATTGAGGCTGACCCTGTATTTTGATTCTTATTTGGCAACT
TATTTCTATTCTGTTCCCAATTCAAAATCCCAAGGGGAGAAGGAAGATAATTGATTACCAGAAGTATGTAATGGTGGTAG
GAAGTTGAATAAATGGTAACTTTTTAAAAGTTGCATGAGATATAGTCCTTATCCCAGAGAAGCTAAGTTTGCTTTTCTTTC
CTCTCATGTATTTTAGTATTATTTCTACAATTAGATTGTAAACCCTTTAAAAGCAAGAATATTTCTACATTTTCTTACTCCT
GATAGCACACAGTAGACTGCTGGGCACATACATAGTAGGTGGCTCTGTAGGTACTTGCTAAATGATTCAACATGTTTTTCC
CTCATGGAAAAGAAAGATTTCAGTATTGTTCTTATCAGCTAGGAAGGCACTCTGAATAGGAAATCAGTTCTAGGCAGGTA
TCCATAAATGGGTTATGATTTCCAACTTACTTGCCCCAGAGGCTCGCTAATGTTGAACTCTTCATGGGTACTTTGTCTTGCT
TCATGAGCTATACATGCTAAGGGGTTAGCAGATCATATAATCTTTTGATCTACAAAATATGATCTTTATTGAACAAAAACT
TGGGCCAAAGGCCTTTCTCCTTTGCCACCTTCCTCCCTCTTTTCATTCTCTTTTTTGGGAATGCCCTTTGTGCATGTTAGTTA
CAGCATGTACCACATTGCACTGTATTGTTGGTTTTTGGGTCTAACCCACCCTTAACACTGCAGTCCCCAAGGGCAGAAATT
CAGTCTCATTCATTTTGATGTCCTCAGTGCCTGTGCTCAGAGAATATCTATTATTTGAAAAAATAGTGCAAAAGTAAATTT
TAGGAGACTACATCACACTCATCTAAACTGCAAGTTTGACAAGTTGACATCCAAAAGAAAGGCTCTCCTAAATAACCTCG
CCACAGAAATTTGGGTGACCTTTGTAGCTCTGGAGAAAGCAGAGGCAAAAATGAAACCTAAAAATTATTTGTGGGTTTTT
AAAAAATGTTTTCTCATGGAGTAAAGGTCTACAGCTGAGTTCTTTTCATATGAGGGAATGACAGAAACACAGCTGGTTCT
GACTTTCAGCTTCAACTGAGCGACCAGAGCTCTGCTGGTGAAACAGGAACTTGTATTGTGCCCCTGACGTGCACCTTGAA
GGTGTCAGCTCATTGTCCCTTTGTTCACATAAATAGTTTTTTAAGAATTGTTTTTGATCTTGTGAGCCTCTAACTAAATGAT
TAACCATGCAAAGTTGGCCATTTGGGGTAATACTGAAGCACTTCTCTTGAGGGCTATTGACAGGTGGGAATGTGCCCACC
TCCTTGGGTCTCTGGTTTTCATGTCATACTTGCAAATCAGTGACAGTTTAAACTTGGGGCAATCACTTAGCAAGTCTATTG

FIG.2 (Continued)

AGTTACCAAGTTAATTATTCCCACTTTGCATGAAGCAACCTTGAAAATGATTTTCCTAAAGCAAAGTACATCCAAACTCAG
TACCTTCTTAATAACCTTTGCTGAATGAATAAATGACTAATTCATAAAAAATGTAACATATCTTTAATTCTTACTTACGGG
CAGTTTAAGCCTCTTGTGTAAGAGGAGGCCTCGGCTTGAGATAACATAGGATAGTAAGCCTCCTAGAGAAATTTCTATAT
GGAAACATGGTCTGCTATGAAGCTAGAAGTGAGAGGACATTATATTTGACCATTATATTTGGCTTCAGAGCTTCTCAACAT
GGGGCCCAAAGTCAAGGTCCCTTGTTTCATTAAGAGGAGGTCCAGGAGTGCATGACACCCATCAGACTACTGAGACCCAG
CTGGAACTAGGCACCTTGCACAGGGGCCTTGCCTAATCAAAATAGTTCTTATTTTTTCTGAGTTCCAAGTAACTAGTTTCCT
AACCCAGTGTCTGGATAGTAGTGCCAAGTGGGAGTACCTTCAATGAACTTCCTCATGAGGTTATTTCTAGCCTATTGGAAT
GTTTCGTTTTAGGAGGGTGAGGAAGGGAAGTCTTGAATTTTTGTGCTTAGTTTAATGTTGTGATACAGCTTTGACCATCCG
TTTAATGGGAGATCTGTTTTCCAGATGACTATACATGTGGAAAGGAGAAGTTTTTTGAGTGTTTTTTTTAACCCCTTTTAAA
GAATGGTTTTTCATTTAGTCTCTACATTTGGGGGTAAAAGGTCCTCTAGGGAGACTTTTCAAAAGTATTTGAAGTTTGCAT
CTGATTTCAGAGGTGAGTTGGAGGCCTATCTGTGTATGACAGACACATGTCTCCAACAACTATATGTTCACAAGGACTAA
GAGCCATCCTTTTGGGTCCATCATTCAACATTGATCTCACATTCGTGTTCGTATCAGTATCTTTACAGTGCGCTCCCAGTTA
CATCTCCCTAATTTCCCTTAGTAGGCTTCACAGAATTTGCAGTGTATGCAATGGCAGATGACCACATGTGGAGTCATTTAA
CCACATCTTCCACTGCAAGTCAGCCCGCTCTTGATGTCTGTTTATGTTTAGATTCCATCTTTTGGAAGATTTCATTCCTCTG
CACTATCTCAGTATCTCAGATGCTTTTGAGACTGGGTCCTTTTCCCCTCCTATGTTTGGCCATGGCCACCCCCTCAGGGTTG
TGTTGTGTTTCACAGCTGCTGTTTGTAGGGTTGACCTTTACAATGTACAAAGCTCTTTCCCATATGTTGACAATCCCTGGTG
TGATGCTGTGAGTTAGGCAGGGTGTGTATACGTGTCCTCATCATATTACAGTGGTAAGGCAACAGGGTTTTTGAATTTGAT
CACCCATGAATTTGTCTAATTTGTTGGTAAAAAATGGTCATGTATCAGCCGTTTCACAGGGTCAGCTTAATAGAAAGTGGG
AGTTAGGCAGGACCAGAATTCAGGACTTCAGCCCCCGGTCCCAGGGACTATTCTCTATACCCAATTGTCCCACCTTGAATC
AGTTTCTTCTAGGGAAATATCTCCAAAACTGAGATGGCACCCACAGGACTTCTTAATTGTAGTCATTACCAGGAAAAACA
AGCAAAGGAACTGGTGTAAATCTCTGTTTTTGGTGATTGGTGGAGATTTGGAGATTGTCTTGTGTCAAAAGTAAAGCCACT
AGATTAAATGTTTTGTTAATAAATTGGTTATTTTTAATTTAATTATTTGACAGTTAATTTACATTATTCAAAAATCAAAATA
AAATTTAAAAGAAGTTTACACTGAAAAGTCTTGCCCCACTTATACCCTGCTCACCTCAGTATCCCCCAATACATACCATCT
ATAAGGTGATCATTTGTATTAGTTTCTTGTGAATCCTTGATAGTGTGTTTTATATAGATACAGGTAAATATGAGTATGTACT
ATTATTTCCCCCCCACCCCACCCTGTTTTTTTTTTGAGACGGAGTCTCGCTCTGTCGCCCAGGCTGGAGTGCAGTGGCACGA
TCTCGGCTCACCGCAAGCTCCACCATTTTCCCCCATTTTTAAAACAAAAGGTAGTAGCCATATATACACTATTTTACACCTT
GTTTTATCACTTACTAATATATACCAGAGAGCTTTCCATCATTTTGTACATATGCACCTATATCTGTCAATTATTCCCAGAA
GTGGAATTGCTGGGTCAGCAGGAAAAATCATGTATAATTTTGATAGGTATTGCCTAATTGTCCTGCACAGGGCTTGAATTG
TTTGTACTCCCACCTTTAGTGTATGAGAAGACCTGTTTCTCCATAGCCTCATCAAACAGAGTGTGTGAGATTAGATGAGAA
ATAGGAGGTGAGCAGTCTTTTACCCCATCCGTAGTTTGCAGTGGGAACACTGCACAGTTGCAAGAGCTGGTGCAGGTATC
AGATTAGTTCCAGTGGAAACGCTGCCTCACCATGGCCATGGGCTTGCGCCAGCTCTAGTGACACACACGGAATGGACCCA
CGTTGCCACTTGCAGAATTTCCTGTAGCAGAAAGTTGAACATGCATTCATTATTCATCTAACTAGCCATGCTGGATCTAAA
GAGCACAACAGTGTTTTTTAGAACCAAAAAGAAAATTGTTTCACTACAACACACTGTGTATAAGGCTTTCAATGCTCTTTT
CTCAGCTATTAACATTATTTTCAGGACTGAGTTCAAGAGATGTATCCCAAATCACAGGGATGTCTTGCTAAGCTTGGAACT
TTCATACTCAAGGGATGCTTTTTTGAGGAATGATTTTACACTTACTCAACATTTGTAATTAAATAATTAGTACTTTATAAGA
TAAATTTAAACTGTCCAAGTACAATATAAACATTGAACTATGATGCATTATTGCTAGACTTTTTCCTTAAAGTTGCCAAGT
GGTTTCCTGCATTAGGCAAATAGGGGATCATATAAAAATGCCATGATTTACGGCCTAGATAACATCTCCACCATTTGAGC
AGCATATATTCCAGGTCATCCCCACATAACTCCTTACCATTCTCATTAGAAAGGTTGATTCTTAGTCTTATTTTTCTCTGAG
GACAGCAAAAAAAAAAATCCCCTTCAGTTCCACTGCATAGAAAAGTGTGGTAAATGGAGCCGGGCACAGTGGTTATTTAA
TTTAAATGGACAATATTTTTTATAGAATTTTGACAGGGCCACTGTATAGGGGAAAGTCACTCCTCTTCCCCTTTATAGAAG
AGTTGCACCTGGACAGTTGCATTGATGACTGTATCCAGTCTACACAAGAGGTCATTCCTGGGCATAAGAATGGACTGCCA
AAATCTAGCTGAAACACCATTGACAAATAGACATTTTCTTTTGTTAATAATACCTGTGAAGGCTTTCATAACAGACATTTC
CAGTTTTGTTCTCAGGCTCCTTGCAGCTGCTCCTCTAAAAGTGTGCTCTCTTCCAAGAGCTGACAATGGCCAGAAGCAAGG
TGTTCTGTCTTTTGTGCCATCATCATCTAACTTGCCACACACATTTGGGATGTCAGCCTAGGTATAGGTTTTGTATCCACTC
AGTATGGCTTGTGGGTCTGGTTGCCTTTGTTATTCATGCTGAGGGCCTCTGGGCATCAGTTTGGTGTGAGAGAACCCATTC
CATGACCCTCCTTCCTTTGGCTGTTTTGACTCGATGGCTCTTGTTGGCACAGTCTGTGAGTGTCTGATGCTCTATCCATGCC
GGACCATCTGTTCTGCTGTCTCTGTGGTCTGAAGTCGTTTTCTGAACTATTCCTTGATAATAAATTTGAGATGATCTTGTTC
TACCTTTCTTTTCAAGTCACATCTTAGCCCCTTAGCCACATTCCCGAAGAACATGACAAATGGATGGGTCACAAGTCACGT
AGCATAGGGTGTCAGACCACGAGGCTTTGAAGGGATTCTGTTGGGTGCTAAAAAGAAAGATTTTGTGTCACCACGATTTT
TTTTAAAGGCATGTTGACACTTAGGCCTTAATTGAAAGCGTTCTTACTCAAGTAGAGTTGACAGAGGAGTATTTGGTAGTC
GCGGTTGCTGGTCTGAAGAGCATGTGGTTCTGTTTCAATGCCCAATGAGATCTTCTCACGGGAAAATGTTCTGACATCTCA
AACAAATGACCTTCATGCATAGTTTTGACAAAATACCCTATTAAGTATGCATATATGGTTGGTACCTTGTGGTAATAATTC
AATACTGGAAACAGAGTAGCAACAAAGAAACATTAGGGTTATATTTAACCTCTGTGGAATTAGTGTGTAAACAAACTGCT
TATCAGAAATGCTCATATGGGGCTTTGTTTAAATAAATAAGAAACTGGCATATAGGGTCTGCAGGATATTTCTGCCAAGT
AGACCTCCCTCACATTATAAGACACCACATCTATGTCTGACCCCATATGGAAAGAGGCATAGCAAGCCAGCACTGGTTCA
TATTCCCTCTCCACCACATAATGGGTATGTGATCTTAGGGAATCCACCGAAACTCTCTGGGCCTCAGTTTCCTCAGCTATA
AATGGTGGATAATCAAATTATTTACCTCACCATTAATAAATGTTAGCTATTATTTTTTATCAAGTTTAATACAAAGAGAAA

FIG.2 (Continued)

CATTTTACTTATTTTTCCAGCTATCCAGAGCATCTTCCAAAATCCTATCACCAACAAATACTGTATTGTATTTATTATAGCA
ACTATGTAAAAATGGAGTCCCTGTCCTATGCTTAGATGAAATATGTTGGTATTTGAGTTTGCATGTCTTCTATAGGAATCA
GTGTTTAGTGAAAACGGGTGGAGATAAACAGATGTTTTCACAGTCCTGTTGTTCACAGTACCGCCAAATTGAATGTTTCCA
TATAGGTGCATTCTAATGGCTTAAATGATGCAGATATTTTCTGGCCAGCCATATGGATCTTTTGTCATCTAAGATGTTAAT
ATTTTCCTTATATTTTATAGTAGTTCTGGAGTACAGCCAGTTTCTTGAATAGGGTCCACATGGCTCATTATGCACAGGGCCT
GGAAACTGCCTTACTCGTGCTGTTGAAATGAACCGTGACACTTCAGAAGAGCTGGGAGCTGGGGTAGAGCAGTGGCTAGG
AGAACATATTCAATTATATTTCCTCCTGCATTAAGCTACAAGTAATGAGCACTTTCCTGTGCTTTACAGTTAAGTAATTAA
AAGAAATTATAGAGTGGGATGCAAAAATAACCCGAAGGACAACTGGATGTGTGGAGCCACCAGTTTTCTCCATGAGTGC
ACAAGGTTAATCCTTGTTACTACTCAGAATGCTGAGTTTCTACAGAAAGGGTTGCAGGTCCACACATGTTTTGGCGTCTAC
CCACACGCTTCTGTATGGCATGACTGTGCATCCCAGAAGAAGGGCTGTGCTGTGTACCTCCACGTTTCAGTGGAATTTAAC
AAACTGATCCCTGAAAATGGTTTCATAAAGGTGAGTAACAGAGAGCTAATAGCCTTCTCTTGCTAATTTTATCTTTCCCCC
AAGATTTCTTGATAATAGTTTGAAAAGGAGTGTTATTCTTTGGTCTCTAGAGGCAACTTACCTTTCCAGTTTCTTCCATCAC
CTGTTTTCATCTCTCTTGTTTTTTTAAATTTAATGCTGTATGTATTTCAGAGGATAGGATCTAATCTAGTGCGGTCCCTTCAT
CAGGTGAGAATTATTCATCTCATTTTCATTTTAGCCCTTCTGAATTAATGACATTGAAGCCCGGCAGTTTGGTCCTAAGAT
GGGTTTAATTATGTACAGATACTCTTTCTATAATGGAAATTGCTCAGATAACTAATTAACCACAAGAATACACTGTCTATG
GAAAATTTCAGGAGCACCGTCTGTGGAAAAACTGGGAAGGGCATGCTGTCACCACAGCTCTGGGGTCTATTAAAAGTGTG
GTTATGCAGCACTGGTGTCTAGTGGGGTGTTGGCTCTCAACTGCCAGAATTCCCATAGCATTTCATGGCAGAAAGTCAAG
GTGTCCAGCAATACTCTGAAAGTGACCTGTTGATTAAAGTCGTCAATTCTGAAGAAAGAGACTGAAATAAGACAAATGGG
TCTTAACTTTTTTTCTCTTTCTCTCTCTTGTAAAAATGTGTGATTGTTCTGGCATGTTCCCAATCCCCACATAATGCCAACAT
CTTTTCTTAAAGGGGGATTCCCTTTATCCTTGGATCTGAGAATTATTGCATGTTCTCCCTTTAGGGACAATGAATGCAGTTG
CATCACCCTTGCTTTTTTTTTTTTTTTTGTACACAGCATGCTTATTCTTGGATGCAGGGACTTGAAAGACAAAGCCCCACCT
GGCTTTCACAACATCTCCTATTAGTAGGTGTGCCTTGTGTGTAATTTGAAGGAGGCGGTCCCTTAGCTGTGTTTACACTGT
ACTTTTAAATGTGGGGCTGAAGGTAGAATCAACCATACTTAAGATGCCACCTGGGAAAATAGGGTTCTGTGTCATCTCAG
CCCCACCCATTTGCAAATGACTTAACAGCAGCACTATTAGGGTTCCTAGTGTGAGTCATTTGCATTTGGACTGGTGAACTT
GGTGACTTCTTGGTGTTTGGAAACAAACAACCTTTGCAGTCTTTCGTAAAAAGCCTGAACAGTGGACCAGTCTCCAGTTCT
ACTTGCAAAGCTGCCCCCATCAAATCCCTCATAATGTTCAACTTAAAAAATGTTACACTTTTCTCTGGAAATCTAACCTTTT
TTCCTTTTTTAAAAGCCATTTTAAGTACTTCAGTCTTGAATCAAATGATCCCAAATATTGGACACCAACCTAGAAATTGGG
TTACCTCCTGGGAACTTTATCGAAGAAGAGAGATTTTGGTTGGAGAGGGGGTTTTGATGTTTGATACTTATATTTACTATT
TTAATATTTCATTGTTGTTGTTGCTGCTGCTGCTGTATTATTTTGCGAGTTTCGTTTGTTTAAATTTCATGGTATTTGGTAGG
AGAGAGCTGGATCTGTTGGTTTCAGGACAAGTCTAGAAATAAGAAATCTGCCTTGAGTGAGTGAGTTGGTTCCCTCTGTTG
CTATTTCACCATTAAGGACGAAAGGAACTCACAAGGACCAGAGACATCTGGCTGAAAGCAATACTAGTGTGACTGGACAT
CTACTACCTGCCATAGTTGGTCATATCGTTTCCAGTATGATTCTGATTGAGTGAGTGATATTAGGCTATGTTCAGGGATCA
GGGAGGCTAATTATGCTTATATTGCCTTGTAGCATTTTGGTAAGAATTAATGATTGTGTAGATGTCCAGATTTAGGTCAGC
AATATTCTAAAAGTTCTCATTGAACTAATCATGTTTATAAGTAGCCTGTACTTTCTATCATAATAACAATAGTGGAAAAGC
TAGTTGACATAAAAGGAGCCCAGATTTTACTTAAGTAAAAACACAAAAGCAAAGATATTTTCCCACATAAATTACAAAAG
CAAAGATATTTTCCCACATAAATGTCCCCATAAAACAAGTTGAACCAAAGAGGAAAGATGACAGGTAACCGTATGACAC
GCTAAGAAAGTATCATAATACTTAAGTTAACTTCAACCTTTTATTTCCTTATCCTAAGCAGCCTCTTTTCTCTTTATCATTTA
GTCCTGTGCTTCTCAACTTTGATAAGTAAAAAAGTTATTGCACTAAATAAATCTTATTGAAATGCAGGATCTGATTGAGTG
GGTGGGGTAGGTGGAATGAGGGTGGGGAAGTTGAGATTCTGCATTTCTTAGAAGTTTCTACTTTATGTTAAAATGGCTAAT
CCATCTCAACATTGAGAAGTAAGGTTTCACTTAATTTCAGCCTGTGTAAGTTTATCCCATATGTACATTTCCTAAAACTCTA
ATCTCAGGCCCCAGGAATTTCTCCTTTAGTTAAAATATTTTTAGGAATAAATTTGAATTGCATTAATACACAATTTATAAA
TTTAACACAAAAAATTATTTGAAGTTTGAGACTTTAGGTTGCATGAAATCAATTTCATACTTGAAAATTTTCTATAAATTC
AAAAGTCTGTGTATTTAAATACAATTTAAATACCTGTGTTACAGTGACATTTGTTTTTCTGTCTCTCTCTCCACCATTTCCA
GAGTCATCATCCCTGTACAGAAAAATTTTTCCCACATGATTTCACCATAAATTCATTAAATATGATGCTTACTTGATAATTT
CTCCAGGTTCTTTTTTTTTTTAATTATACTTTAAGTTCTAGGGTACATGTGCACAACCTGCAGGTTTGTTACATATGTATAC
ATGTGCCATGTTGGTGTGCTGCACCCATTAACTCGTCATTTACATTAGGTATATCTCCTAATGCTATCCCTCCCCCCTACCC
CTACTCCATGACAGGTCCCAGTGTGTGATGTTCCCCACCCTGTGTCCAAGTGTTCTCATTGTTCAGTTCCCACCTATGAGTG
AGAACATGCGGTGTTTGGTTTTCTGTCCTTGCGATAGTTTGCTCAGAATGATGTCCTTGCTCACTGATGGACATTTGGTTGG
CTCCAAGTATTTGCTATTGTAAATAGTGCCGCAATAAACATACGTGTGCATGTGTCTTTATAGTAGCATGATTTATAATCC
TCTGGGTATATACCCAGTAATGGGATGGCTGGCTCAAATGGTATTTCTAGTTCTAGATCCTAGAGGAATCGCCACACTGTC
TTCCACAATGTTTGAACTAGTTTACAGTCCCATCAACAGTGTAAAAGTGTTCCTATTTCTCTACATCCTTTCCAGCACCTGT
TGTTCCGGACTTTAATGATCGCCATTCTAACTGGTGTGAGATGGTATCTCATTGTGGTTTTGATTTGCATTTCTCTGATGGC
CAGTGATGATGAGCATTTTTTCATGTGTCTTTTGGCTACATAAATGTCTTCTTTTGAGAAGTGTCTGTTCATATCCTTCACC
CACTTTTTGATGGGGTCATTTGATTTTTTCTTGTAAATTTGTTTAAGTTCTTTTAGATTCTGGATATTAGCCCTTTGTCAGAT
GGGTAGATTGTAAAAATTTTCTCCCATTCCGTAGGTTTCCTATTCACTCTGATGGTAGTTTCTTTTGCTGTGCAGAAGCTCT
TTAGTTTAATTAGATCCCATTTGTCAATTTTGGCTTTTGTTGCCATTGCTTTTGGTGTTTTAGTCATGAAGTCCTTGTCCATG
CCTATGTCCTGAATGGTATTGCCTAGGTTTTCTTCTAGGGTTTTTATGGTTTTAGGTCTAACGTGTAAGTCTTTAATTCATCT
TGAATTAATTTTTGTATAAGGTGTAAAGAAGGGATCCAGTTTCAGCTTTCTACATATGGCTAGCCAGTTTTCCCAGCACCA

FIG.2 (Continued)

TTTATTAAATAGAGAATCCTTTCCCCATTTCTTGTTTTTGTCAGGTTTGTCAAAGATCAGATGGTTGTAGATGTGTGGTATT
GTTTCTGAGGGCTCTGTTCTGTTCCATTGGTCTATATCTCTGTTTTGGTACCAGTACCATGCTGTTTTGGTTACTGTAGCCTT
GTAATATAGTTTGAAGTCAGGTAGCGTGATGCCTCCAGCTTTGTTCTTTTGGTTTAGGATTGTCTTGGCGATGCGGGCTCTT
TTTTGGTTCCATATGAACTTTAAAGTAGTTTTTTTCCAATTCTGTGGAGAAAGTCATTGGTAGCTTGATGGGGATGGCATTG
AATCTATAAATTACCTTGGGTAGTATGGCCATTTTCATGATATTGATTCTTCCTACCCATGAGAATGGAATGTTCTTCCATT
TGTTTGCGTCCTCTTTTATTTCCTTGAGCAGTGGTTTGTAGTTCTCCTTGAAGAGGTCTTCCACATCCCTTGTAAGTTGGATT
CCTAAGTATTTTATTCTCTTTGAAACAATTGTGAATGGGAGTTCACTCATGATTTGGCTCTCTGTTTGTCTGTTATTGGTGT
ATAGGAATGCTTGTGATTTTTGCACATTGATTTTGTATCCTGAGACTTTGCTGAAGTTGCTTATCAGCTTAAGGAGATTTTG
GGCTGAGATGATGGGGTTTTCTAAATATACAATCATGTCATCTGCAAACAGAGACAATTTGACTTCCTCTCTTCCTATTTG
AATATCCTTTATTTCTTTCTATTGCCTGATTGCCCTGGCTAGAACGTCCAATACTATGTTGAATAGGAGTGGTGACAGAGG
ACATCCTTGTTTTGTGCCAGTTTTCAAAGGGAATGCTTCCAGCTTTTGCCCATTCAGTATGACATTGGCTGTGGGTTTGTCG
TGAATAGCTCTTATTATTTTGAGATATGTCCCATCAATACCTAGTTTATTTAGAGTTTTTAGCACAAAGGCTGTTGAATTTT
GTCAAAGGCCTTTTCTGCATCTATTGAGATAATCATGGTTTTTGTCTTTGATTCTGTTTATATGATGGATTATATTTATTGAT
TTGCATATGTTGAACCAGCCTTGCATCCCAGGGATGAAGCCAACTTGATCATGGTGGATAAGCTTTTTGATGTTCTGCTGG
ATTCGGTTTGCCAGTATTTTACTGAGGATTTTTCCATCGATCTTCATCAGGGATATTGGCCTGAAATTCTCTTTTTTTGTTGT
GTCTCTGTCAGGCTGTGGTATCAGGATGATGCTGGCCTCATAAAATGAGTTAGGGAGGATTCCCTCTTTTTCTATTGATTA
GAATAGTTTCAGAATGGTACCAGCTCCTCCTTATACCTCTGGTAGAATTCAGCTGTGAATCCATCTGGTCCTGATGGATTT
TTTTGGTTGGTAGGCTATTAATTATTGCCTCAATTTCAGAGCCTGTTATTGGTCTATTAAGAGATTCAACTTCTTCCTGGTT
TAGTCCTGGGAGGGTGTGTGTGTCCAGGAATTTATAAATTTCTTTTAGGTTTTCTAGTTTATTTGCATAGAAGTGTTTATAG
TGTTCTCTGATGGTAGTTTGTATTTCTGTGGGATTGGTGGTGATATCCCCTTTATCACCTTTTATTGCATCTATTTGATTCTT
TTCTCTTTTCTTCTTTATTAGTCTTGCTAGTGATCTATCAATTTTGTTGATCTTTTTAAAAAACCAGCTCCTGGGTTCATTGA
TTTTTTGAAGGAGTTTTTCTGTCTCTATCTCCTTCAGTTCTACTCTGATCTTAGTTATTTCTTGTCTTCTGCTAGCTTTTGAAT
GTGTTTGCTCTTGCTTCTCTAAATTGTGATGTTAGGGTGTCAATTTTAGATCTTTCCTGCTTTCTCTTGTGGGCATTTAGTGC
TATAAATTTCCCTCTACACACTGCTTTAAATGTGTCCCAGAGATTCTGGTATGTTGTGTCTTTGTTCTCATTGGTTTCAAAG
AACATCTTTATTTCTGCCTTCACTTCGTTAAGTACCCAGTAGTCACTCAGGAGCAGGTTGCTCAGTTTCCATGTAGTTGAGT
GGTTCTGAGTGAGTTTCTTAATCCTGAGTTCTAGTTTGAAAGCACTGTAGTCTGAGAGGCAGTTTGTTATAATTTCTGTTCT
TTTACATTTGCTGAGGAGTGCTTTACTTCCAACTATGTAGTCAATTTTTGGAATAAGTGTGATGTGGTGCCGAGAAGAATG
TATATTCTGTTGATTTGGAGTGGAGAGTTCTGTAGATGTCTATTAGGTCCGCTTGGTGCAGAGCTGAGTTCAATTTCTGGA
TATCTTTGTTAATTTTCTGTCTTGTTGATCTGTCTAATATTGACCGTGGGGTGATAAAGTCTCCCATTATTATTGTGTGGGA
GTCTAAGTCTCTTTGTAGGTCTCTAAGGACTTGCTTTGTGAATCTGGTGCTCCTGTATTAGGTGCATATATTTTTAGGATAG
TTAGCTCTTCTTGTTGAATTGATCCCTTTATCATTATGTAATGGCCTTCTTTGTCTCTTTTGATCTTTGTTGGTTTAAAGTCT
GTTTTATCAGAGACTAGGATTGCAACTCCTGCTTTTTTTTGCTTTCCATTTCCTTGGTAGATCTTCCTCCATCCCTTTATTTT
GAGCCTATGTGCGTCTCTGCACATGAGATGGGTCTGCTGAATACAGCACACTGATGGGTCTTGACTCTTTATCCAATTTGC
CAGTCCATGTCTTTTAACTGGAGCATTTAGCCCATTTACATTTAAGGTTAATATTGTTATGTGTGAATTTGATCCTGTCATT
ATGATGTTAGCTGGTTATTTTGCTCGTTAGTTGATGCAGTTTCTTCCTAGCCTCAATGATCTTTACAATTTGGCATGTTTTTG
CAGTGGCTGGTACTGGTTGTTCCTTTCCATGTTTAGTGCTTCCTTCAGGAGCTCTTGTAAGGCAGGCCTGGTGGTGACAAA
ATCTCTCAGCATTTGCTTGTCTGTAAAGGATTTTATTTCTCCTTCACTTATGAAGCTTAGTTTGGCTGGATATGAAATTCTG
GGTTGAAAATTCTTTTCTTTAAGAATGTTGAATATTGGCCCCCACTCTCTTCTGGCTTGTAGAGTTTCTGCCGAAAGATGCT
GTTAGTCTGATGGACTTCCCTTTGTGGGTAACCTGCCCTTTCTCTCTCGCTGCACTTAATGTTTTTTCCTTCATTTCAACTTT
GGTGAATCTGACAATTATGTGTCTTTGAGTTACTCTTCTTGAGGAGTATCTTTGCGGCATTCTCTGTATTTCCTGAATTTGA
ATGCTGGCCTGCCTCACTAGATTGGGGAAGTTCTCCTGGATAATATCCTGCAGAGCGTTTTCCAACTTGGTTCCATTCTCCC
CATCACTTTCAGGTACACCAATCAGATGTAGATTTGGTCTTTTCACATAGTCCCATATTTCTTGGAGGCTTTGTTCATTTCT
TTTTACTCTTTTTTCTCTAAACTTCTCTTCTTGCTTCATTTCATTCATTTGATCTTCAATCCCTTTCTTCCACTTGATTGAATC
AGCTACTGAAGCTTGTGCATGTGTCACATAGTTCTCGTGCCATGGTTTTCAGCTCCATCAGGTCATTTAAGGTCTTCTCTAT
GCTGTTTTTTCTAGTTAGCCATTCGTCTAATGTTTTTTCAAGGTTTTTAGCTTCTTTGCTAAAAGGTTCAAACATCCTCCTTT
AGCTCGGAGGAGTTTGTTATTACTGATCATCTGAAGCCTTCTTCTCTCAACTTGTGAAAGTCATTCTCTGTCCAGCTTTGTT
CCATTGCTGGCGAGGAGCTGCATTCCTTTGGAGGAGAAGACGTGCTCTGATTTTTAGAATTTTCAGCTTCTCTGCTCTGGTT
TCTCCCCATCTTATTGGTTTTATCTACCTTTGGTCTTTGATGATGGTGACGTACAGATGGGGTTTTGGTGTGGATGTTCTTTC
TCTTTGTTAGTTTTCCTTCTAACAGTCAGGACCCTCAGCTGCAGGTCTGTTGGAGTTTGCTGGAGGTCCACTCCAGACCCTG
TTTGCTTGGGTATCACCAGCAGAGGCTGCAGAACAGCAAATATTGCAGAACGGCAAATGTTGCTCCCTGATTGTTCCTCTG
GAAGCTTCGTCTCAGAGGGGCACCTGGCCGTATGAGGTGTCAGTCGGCCCCTACTGGGAGGTGCCTCCCAGTTAGGCTAC
TCAGGGGTCAGGAACCCACTTGAAGAGGCAGACTGTCCATTCTCAGATATCATATTCCATGCTGGGAGGACCCCTACTCTT
TTCAAAGCTGTCAGACAGGGACATTTAAGTCTGCAGAAGTTTCTGCTGTCTTTTGTTCAGCTGTGCCCTGCCCCTAGAGGT
GGAGTCTACAGAGGCAGGCAGGCCTCCTTGAGCTGCGGTGGGCTCCACCCATTTCGAGCTTCCTGGCTGCTTTGTTTACCT
ACTCAAGTCTCAGCAATGGTGGACACCCCTCCCCCAGCCTCGCTGCTGCTTTGCAGTTCGATCTCAGACTGCTGTGCTAGC
AGTGAGCCAGGCTCCGTGGGCATGGGACCCTCCGAGCCAGGCCTGGGACATAATCTCCTGGTGTGCCGTTTGCTAAGACC
ATTGGAAAAGCACAGTATTAGGGTGGGGAGTGTCCTGATTTTCCAGGTACCGTCAGTCATGGCTTCCCTTGGCTAGGAAA
GGGAATTCCCCAACCCCTTGTGCTTCCTGGGTGAGGTGATGCCCCACCCTGCTTTGGCTCATGCTCCGTGGGTTGTACCCA

FIG.2 (Continued)

CTGTCTGACAAGCCCCAGTGAGATGAACCCGGTACCTCAGTTGGAAATGCAGAAATCACCCGTCTTCTGCATCACTCACG
CTGGGGGCTGTAGACTGGAGCTGTTCATATTTGGCCATCTTGGAACCTCCCTTTCCAAGTTCTTTATTACAGAGTGGGTCA
CTGAAACTTCATGGAACAAATTGGAAATTATCTTCTTAATTAATGTCACTGTCTACCATGTATGGGAATTTGGTAAATATT
ATATGGTTTCAATAACATAGTAGATAGAACATTGTCAAATCTAAACTTCAGTGAATTGTAACAGATCCCACCTGAAATTCT
AAAGAAAACAGAATTCTAATTGAAGAGGTTAAACTTTTACAGGGAATGTCAACTGCCATTTGGGTCCTGTAAACAAAAAA
CTGTTTTTTAAAAAAGTAAACTTTAAAAGTATTTTCAGATGACCTCATTTGCTATCCAAGTGGCTTGAGTATGCTTGATGCT
AAGACTTCTTTGTTACAGACTGGAGATGTGTGCTACTGGGGCAGTGTTGCTCTGTGACAAGGAGGCAGAGGATGAGGGCA
AGGTTCGATGTGACTGTGAATTCTGGGTGGCTCTGGCTATCGGGAGCCTTCATTGATTACAGCAAAACAGTTGCTTTCCTA
GGGCAATAGTGTCTCTGTCACCCAGGCTGGAGTTCAGTGGCATGATCAATCGCTCACTGTAGCCTCAACTTCTTAGACTCA
AGTAATCCTCCCACCTCAGCCTCCCAAGTAGCTGAAACTACAGGTGTGCACCACCACACCTAATTTTTTTAATTTTTAAGT
TTTTGTAGAGACATGGTCTCACTGTGTTGCCCAGGTTGATCTCGAATTCCTGGGCTCTAGTGATCCTCCCGCCTCGGCCTCC
CAAAGTGTTGGGATTACAAATGTGAGCCACTGCACCTGGCCCTTTGCAACCTTCTTGACAATGCATTCCTTTATTCCCTAA
CTGGAAGTAACTTCTTTCTCTTTATAAAATTGTATCTGTACCTTTTCTGGGTCATTTCTACCTTTATATTCTAGTTACGTATG
TCCTACCTCCCTCCTAGGGAGGGAGGTAAGTAAGACTGGAAAGTAGACTTCATGTGTGATGAATGAATGAACAAAAGGA
AGTCTAACATATGGATATAGTCAACTGGATGCAAATTAAAAATTTTTAAATATTGATTTGCAAGATTTCATTAAGGTCAAC
TCTTAATAGTTTGTATCATATATGTTAGGAACCAAATATTAATAACTTCTTCAGCATTACCATTATCTTTATAGGACTGTCT
AAAATGAGCAGCCATATCTTTAAACTGTGTTTTCTCTGATTACACGCTCACAGGTAAAACCCAAAGGGGCTGGGAACAAA
CAAGACTTTTTTTTTTTTCTGTATGCCTGAATTATCTGTACTGTTGCTTGTTTTCCCACCTTTGGCCATAGAAACTTAGTTCT
AACATGCTACAATTTTTGCAGTTCTTTCTCTTAGAAAAAGACCACATTGTCTGAAATTTCATCCATTTAAGTAATCAAGCCT
TAAAGTTGAAGGATCTTGGTCATGATTAATCTAGACCTACAAAGTAGTATCTTAATGGCACTCCTTTTAGAAAGTTAGGTT
CCAGGACACACATAGCTGCAGTGTCCACATTTTGTAAGCTCCTTCGTTGTCACAGCCACTCTCTTCTCTGTGGCTGATATTC
TAAAACTGGCAACACATCCTGATGGTAAAAGCTTGGTTCAGGAGACAGGTGACCTACTAGCTTTATGGCATTTGACAGGT
TACCTAACCTCTCTGACGCATAATTGCCTCATCTATATAATGGGGATAATAATACCCATCCTGTCTCCTTGTAAAAATCAA
ATTAGATGACGCCTGTGAATGTTCTATAGTCTCTTAGACAAATGTAAGTTATGACTACAGCAAGAGTAAAAGAGCATGTT
GTTATGGACATTCTTTCAGTGAAATGTCTAAGACTTGTGAGTCACACTTAAAGCTAAACTTGATATCTACTTCATTGATTTT
CTTTTTAGTTCTATGTACTATATTGAATTTCCTGACAGTGGGGCTATGAAAGCCTTCCTAGCATTTTATAGATGTGGTTGAA
TTAATGGCTGTAAGCCTTAAAGCAGAATTAGACAGCATCAATGAATTTATTAAGTATAAATAAATATATAATCTGCTTAGC
AATATTACACAGCCTCTTTATCTTATGTGTGATAAAGAGTCATCCGAAGGTTGAAAATGAAGAATTGTCCTGGAAGCTCTT
ACTTAATCTTTTATTATTTCCTAATACAGTATATAAAATTACTCATTGAAAGCTTAGCAGAATAAGAAACAAGAAGTTAAA
AGGCTGAAAACTACAAATTTTGCTATTATTATTGTTATTACTTCCCAAGTCTCTTATTGATCTGTTAGAAATAGAGCTACAC
AGGAAATTGTAGGACAGTTAGTATGTGGTAGTGTTATCTGCTTTTTAATTATTCAAGTAAGGTTTTATTCCATTAGAGGAA
CTCAAGAAGTTGGTCATGGCTGATAATTGCTATCTGTCAAATTCCTTAGAGCAGGGATCCGCAACACCCAGGCCATGGAT
TGTTACCAGTCCCTGGCCTGTTAGGAACCAGGCTGCACAGTAGGAAGTGAGCGGCGGGTGAGCAAACATTGCCATCTGAG
CTCTGTCTCCTTTCAGATCAGCAGCAGCATTAGATTCTCATAGAAGCATGAGCCCTGTTGTGAACTGCACATGCAAGGGAT
CTAGGTTGTGTGCTCCTTATGAGAATCCAATTCCTTATGATAATTTAACTGATGATCTAAGGTGGAACCATTTCATCCCAA
AACCATCCACCCTGCTACTCCCAGACCGTGGAAAAATTGTCTTCCACAAAACTGGTTCCTGCTGCCAAAAAGGTTGGGAC
CACTGCCTTAGAGTTTATAATTTGGGGTTAGCACAGCCTATATTTACCTGAGAATTTCAATGGGTTCACTGATCTTTCCAA
ATGAAAAGGCTTCTTACGAAAATTATATCCAAACTGTCTTTTCTCTTAGTTTAATAAACCTATCAGTAAGTTTTTACTGAGT
ACTGCTATTACATTTTTCTCTGTTAAGCATTATGGGGGCTCAGACATGATCCATTCCCTCAAAGAACTTACCTTTCAGCTGA
AGACTGACTAGAATGAGCAAATACGGTTAACAATTAACAAGTGAGTAGGCCAGCTCGGCCAACATGGTGAAACCCTGTCT
CTACTAAAAATACAAAAATTAGCCGGGCATGGTGGTGGGCGCCTGTAATCCCAGCTACCTCCTGCTGAGGCAGGAGAATT
GCTTGAACCCAGGAGGTGGAGATTGCAGTGAGCCGAGATTGCACCATTGCACTCCAGCCTGGGCGACAGAGCAAGACTCT
GTCTTGGGAAAAAAACAAAACAAAACAAGTGAGAAGGGAATCAAGTACTACGTAAGATGTAATGTGGAATTTTAGGGAA
GGAAGGCAGTGTATGCTGGAGTAATTAGAGAAAGGGGCATGCATGATTTGATGCTTGAACTGGATCATGAAGGATAAGC
AAGATTTTGGCAGCAAGTGAGAGGGAGAGAGGAGTTTGTCAGAGGAATGGAACAAGTCAGGAGGCAGTAATGTGTACGG
CACTCCAAGGACTCTGTCCTGATCGGAGCAGAAGTGATGAAGCATTGAGTAGTTTGAGAAAGTTAGCTAAGAAGGGTGA
GGGCAGATGTTGGAGAGAGTTGAGTATCAGAGAGAAGACATTAGATTTGAGCAGATAGAACAAAAATGCCATTGCCAGT
TTTTGTGTAAGAGAATAGTATTAGGGTGGTTACCCAGGAAGTGGTCATCAGAGTTGAATGGAGCAGAAAGAGTGTCTGAT
ACAGCATCGGGACGTTGTGGTCACAAAATGAGGTGGTGAGGGCTGAGCCAAGATGGTGGCAGTGGGATGGATAAAAAGG
GATGGCCAGGACAAATATTTTAAAGGAAAAATTAACAGGACATCTTTACTGACTGGATTGGAAGGCTATGCAGGAAATAT
ATTGTCAAACTTGATTCCAGGATTTCTATCCTATGCCTGGGTTGCCCAAAATATCAGGGAACCATTGTTAGAAAAGGTAGG
AGATACCACTGTTCCAACAAAAAGTATTGAGTTTGGTGTTGCACCCACTTAACTTCAAGGCCTTACAAGTGAGTAGACAG
TTAGTTAGAATTGCAGAAGTGCCACTCAGAGAGCAGGGCTTGCAATGTGGGGTTGGACTTTGTCACCATTGTGTTAATTCC
TAATTCTATGCAGATGCTCAGCTTGAGGAATACCCATGTTTGGGCTTCAGAATGAAAGCCAAGTAATATTTACTCAGATGC
CAATTTTCCCTCTGAAATATTTGCTCATGGAACTGAGAGAACAATATATAAAGCATTAATTATTTTTCTCATAAAGTTATT
AATAAAAAGATAAGATCAGTGAAAGGCAGAGTAAACTAGAAGCCAAGTATAGAAAATGGTATCATTCAAAGACTCATTA
CTGTAGTGGTGAAAACAAAACAATTTTCCAACAGCTTAAGATGCCTCAGTATTTTGGACCATTTTTAAGTAGTTAGTGTGG
GCACTTAGTAAATATGTATTAAACTATAGTTCATTAATTCTTTTTTTTTTTTTTTTGAGATGGAGTTTCACTCTGGTCACCCA

FIG.2 (Continued)

GGCTGCATTTTTGCTTTCTTAGTGATATATAAAATGTCGAGTTTCACAATGATGGTATCTTAGATTTGATTAAATATGGTAT
TAAAAAATAGCTGATCACAGAAAGTCTCTACCAGTGTGATGTAGATGGCTAAAGTATTCCACATTTGCAAACTTTTATTGA
CCTAAATAAGAGGTGCCCCTTGGGTTGTTTTTATTTGGACTGGGAATATTAGGAGAAAGCTTTTTCATTCAGTGTGTAAGT
ACAATCTACCAGAAATAGAAACCCCCATGGACGATCTATTTCTTTGATGGTACAGGACTCAGAACATTCACAAAGATTTA
GTTGTTAGCGGAATAGACATCTGTATTTTATTCAAACCAATTTTCCCTTCCTAATCTGAGAACATTGTGCAATCTAAGCAG
TTCTAAGCATGTTTGCTATTCGTGCAAAGTGAGAGTAAATCTAAAAGAAATTTTTTTGTGTGTTTAGGGATGGTAATAAAG
TCTCTTAGTGGTTGAAAATGTTATTTCTTACAAAAGTGGAGAACATTTGCTTTTCAATACCAGAGTTTTCAGCCATTTCTGC
ATTCTGACCTATTGACTGGAGGTAGGTTGCCTTTGAATTCAGTAAAACTTCATGGGCAGAAACACAGTTCCTTTTCCTACT
TATTTGGATATCATGATGGCCATTGCATGTATGTGTCTTTTTGTAAGTCCATGCCTCAGAACTGAGAAGTAGGAATAAAAT
TAGGGTCAGGGCTGGGGATGCTACTCTTTGCTGCTGAGAAACACAATGCTTCAGGTAAGTGATTCTGAAGTCCTTCACCAC
CTGACGGTAACCTTGGGTTGGTCCATAGGTATGTTTTCATTTTGCTTGTTCATCCATTTTAATTGGCTTCCTAGAGCATGCT
TGTAGATGTAGAGCCAAATTTAGAGTAGAGCAACCCTCTGGCAAACAGGAAGAGATTAATTTTGTGGTATGCTTTTAAGG
GACTTCCCAGGAAACTTCAAAAGCAGAAAAAGAAGCACTAGCTGCCTATTCCAAAATGTGTAAAACACCACTCAGCTTTT
TAAAAGTAGGATAAACTCAGAGCGCGCGCACACGCGCGCGCGCACACACACACACACACACAGAGAGAACATCTCTAGT
AAAAAGAAAAGTTGAGCTTTCTTAGCTAGATGTGTGTATTAGCCAGAAAAAGCCAAGGAGTGAAGGGTTTTAGAGAACT
GGAGGAGATAAAGTGGAGTCTGCATATGGGAGGCATTTGAAATGGACTTAAATGTCTTTTTAATGCTGACTTTTTCAGTTT
TCTCCTTACCAGACACATTGTTTTCATGACATTAGCCCCAGGCATAGACACATCATTAAAATGAACATGTCAAAAAATGAT
TTCTGTTTAGAAATAAGCAAAACATTTTCAGTTGTGACCACCCAGGTGTAGAATAAAGAACAGTGGAATTGGGAGCCCTG
AGTTCTAACATAAACTTTCTTCATGACATAAGGCAAGTCTTCTATGGCCTTTGGTTTCCTTACCTGTAAAACAGGATGGCT
CAATGAAATTATCTTTCTTCTTTGCTATAATAGAGTATCTCTGTGGGAAGAGGAAAAAAAAAGTCAATTTAAAGGCTCCTT
ATAGTTCCCCAACTGCTGTTTTATTGTGCTATTCATGCCTAGACATCACATAGCTAGAAAGGCCCATCAGACCCCTCAGGC
CACTGCTGTTCCTGTCACACATTCCTGCAAAGGACCATGTTGCTAACTTGAAAAAAATTACTATTAATTACACTTGCAGTT
GTTGCTTAGTAACATTTATGATTTTGTGTTTCTCGTGACAGCATGAGCAGAGATCATTAAAAATTAAACTTACAAAGCTGC
TAAAGTGGGAAGAAGGAGAACTTGAAGCCACAATTTTTGCACTTGCTTAGAAGCCATCTAATCTCAGGTTTATATGCTAG
ATCTTGGGGGAAACACTGCATGTCTCTGGTTTATATTAAACCACATACAGCACACTACTGACACTGATTTGTGTCTGGTGC
AGCTGGAGTTTATCACCAAGACATAAAAAAACCTTGACCCTGCAGAATGGCCTGGAATTACAATCAGATGGGCCACATGG
CATCCCGGTGAAAGAAAGCCCTAACCAGTTTTCTGTCTTGTTTCTGCTTTCTCCCTACAGTTCCACCAGGTGAGAAGAGTG
ATGACCATCCTTTTCCTTACTATGGTTATTTCATACTTTGGTTGCATGAAGGCTGCCCCCATGAAAGAAGCAAACATCCGA
GGACAAGGTGGCTTGGCCTACCCAGGTGTGCGGACCCATGGGACTCTGGAGAGCGTGAATGGGCCCAAGGCAGGTTCAA
GAGGCTTGACATCATTGGCTGACACTTTCGAACACGTGATAGAAGAGCTGTTGGATGAGGACCAGAAAGTTCGGCCCAAT
GAAGAAAACAATAAGGACGCAGACTTGTACACGTCCAGGGTGATGCTCAGTAGTCAAGTGCCTTTGGAGCCTCCTCTTCT
CTTTCTGCTGGAGGAATACAAAAATTACCTAGATGCTGCAAACATGTCCATGAGGGTCCGGCGCCACTCTGACCCTGCCC
GCCGAGGGGAGCTGAGCGTGTGTGACAGTATTAGTGAGTGGGTAACGGCAGCAGACAAAAAGACTGCAGTGGACATGTC
GGGCGGGACGGTCACAGTCCTTGAAAAGGTCCCTGTATCAAAAGGCCAACTGAAGCAATACTTCTACGAGACCAAGTGC
AATCCCATGGGTTACACAAAAGAAGGCTGCAGGGGCATAGACAAAAGGCATTGGAACTCCCAGTGCCGAACTACCCAGT
CGTACGTGCGGGCCCTTACCATGGATAGCAAAAAGAGAATTGGCTGGCGATTCATAAGGATAGACACTTCTTGTGTATGT
ACATTGACCATTAAAAGGGGAAGATAGTGGATTTATGTTGTATAGATTAGATTATATTGAGACAAAAATTATCTATTTGTA
TATATACATAACAGGGTAAATTATTCAGTTAAGAAAAAAATAATTTTATGAACTGCATGTATAAATGAAGTTTATACAGT
ACAGTGGTTCTACAATCTATTTATTGGACATGTCCATGACCAGAAGGGAAACAGTCATTTGCGCACAACTTAAAAAGTCT
GCATTACATTCCTTGATAATGTTGTGGTTTGTTGCCGTTGCCAAGAACTGAAAACATAAAAAGTTAAAAAAAATAATAAA
TTGCATGCTGCTTTAATTGTGAATTGATAATAAACTGTCCTCTTTCAGAAAACAGAAAAAAAACACACACACACACAACA
AAAATTTGAACCAAAACATTCCGTTTACATTTTAGACAGTAAGTATCTTCGTTCTTGTTAGTACTATATCTGTTTTACTGCT
TTTAACTTCTGATAGCGTTGGAATTAAAACAATGTCAAGGTGCTGTTGTCATTGCTTTACTGGCTTAGGGGATGGGGGATG
GGGGGTATATTTTTGTTTGTTTTGTGTTTTTTTTTCGTTTGTTTGTTTTGTTTTTTAGTTCCCACAGGGAGTAGAGATGGGGA
AAGAATTCCTACAATATATATTCTGGCTGATAAAAGATACATTTGTATGTTGTGAAGATGTTTGCAATATCGATCAGATGA
CTAGAAAGTGAATAAAAATTAAGGCAACTGAACAAAAAAATGCTCACACTCCACATCCCGTGATGCACCTCCCAGGCCCC
GCTCATTCTTTGGGCGTTGGTCAGAGTAAGCTGCTTTTGACGGAAGGACCTATGTTTGCTCAGAACACATTCTTTCCCCCC
CTCCCCCTCTGGTCTCCTCTTTGTTTTGTTTTAAGGAAGAAAAATCAGTTGCGCGTTCTGAAATATTTTACCACTGCTGTGA
ACAAGTGAACACATTGTGTCACATCATGACACTCGTATAAGCATGGAGAACAGTGATTTTTTTTTTAGAACAGAAAACAAC
AAAAAATAACCCCAAAATGAAGATTATTTTTTATGAGGAGTGAACATTTGGGTAAATCATGGCTAAGCTTAAAAAAAACT
CATGGTGAGGCTTAACAATGTCTTGTAAGCAAAAGGTAGAGCCCTGTATCAACCCAGAAACACCTAGATCAGAACAGGA
ATCCACATTGCCAGTGACATGAGACTGAACAGCCAAATGGAGGCTATGTGGAGTTGGCATTGCATTTACCGGCAGTGCGG
GAGGAATTTCTGAGTGGCCATCCCAAGGTCTAGGTGGAGGTGGGGCATGGTATTTGAGACATTCCAAAACGAAGGCCTCT
GAAGGACCCTTCAGAGGTGGCTCTGGAATGACATGTGTCAAGCTGCTTGGACCTCGTGCTTTAAGTGCCTACATTATCTAA
CTGTGCTCAAGAGGTTCTCGACTGGAGGACCACACTCAAGCCGACTTATGCCCACCATCCCACCTCTGGATAATTTTGCAT
AAAATTGGATTAGCCTGGAGCAGGTTGGGAGCCAAATGTGGCATTTGTGATCATGAGATTGATGCAATGAGATAGAAGAT
GTTTGCTACCTGAACACTTATTGCTTTGAAACTAGACTTGAGGAAACCAGGGTTTATCTTTTGAGAACTTTTGGTAAGGGA
AAAGGGAACAGGAAAAGAAACCCCAAACTCAGGCCGAATGATCAAGGGGACCCATAGGAAATCTTGTCCAGAGACAAG

FIG.2 (Continued)

ACTTCGGGAAGGTGTCTGGACATTCAGAACACCAAGACTTGAAGGTGCCTTGCTCAATGGAAGAGGCCAGGACAGAGCT
GACAAAATTTTGCTCCCCAGTGAAGGCCACAGCAACCTTCTGCCCATCCTGTCTGTTCATGGAGAGGGTCCCTGCCTCACC
TCTGCCATTTTGGGTTAGGAGAAGTCAAGTTGGGAGCCTGAAATAGTGGTTCTTGGAAAAATGGATCCCCAGTGAAAACT
AGAGCTCTAAGCCCATTCAGCCCATTTCACACCTGAAAATGTTAGTGATCACCACTTGGACCAGCATCCTTAAGTATCAGA
AAGCCCCAAGCAATTGCTGCATCTTAGTAGGGTGAGGGATAAGCAAAAGAGGATGTTCACCATAACCCAGGAATGAAGA
TACCATCAGCAAAGAATTTCAATTTGTTCAGTCTTTCATTTAGAGCTAGTCTTTCACAGTACCATCTGAATACCTCTTTGAA
AGAAGGAAGACTTTACGTAGTGTAGATTTGTTTTGTGTTGTTTGAAAATATTATCTTTGTAATTATTTTTAATATGTAAGGA
ATGCTTGGAATATCTGCTGTATGTCAACTTTATGCAGCTTCCTTTTGAGGGACAAATTTAAAACAAACAACCCCCCATCAC
AAACTTAAAGGATTGCAAGGGCCAGATCTGTTAAGTGGTTTCATAGGAGACACATCCAGCAATTGTGTGGTCAGTGGCTC
TTTTACCCAATAAGATACATCACAGTCACATGCTTGATGGTTTATGTTGACCTAAGATTTATTTTGTTAAAATCTCTCTCTG
TTGTGTTCGTTCTTGTTCTGTTTTGTTTTGTTTTTTAAAGTCTTGCTGTGGTCTCTTTGTGGCAGAAGTGTTTCATGCATGGC
AGCAGGCCTGTTGCTTTTTTATGGCGATTCCCATTGAAAATGTAAGTAAATGTCTGTGGCCTTGTTCTCTCTATGGTAAAG
ATATTATTCACCATGTAAAACAAAAAACAATATTTATTGTATTTTAGTATATTTATATAATTATGTTATTGAAAAAAATTG
GCATTAAAACTTAACCGCATCAGAAGCCTATTGTAAATACAAGTTCTATTTAAGTGTACTAATTAACATATAATATATGTT
TTAAATATAGAATTTTTAATGTTTTTAAATATATTTTCAAAGTACATAA

FIG.3

Natural antisense sequence (NR_002832.1): SEQ ID NO: 2

>gi |84872122 | ref | NR _002832.1| Homo sapiens BDNF opposite strand (non-protein coding) (BDNFOS ), non-coding RNA CNGCNNAAAGATTTCTTCACAGGGTCCTTTAAACTGTCNNTTTNTAAGAGGTCCTTCCACTACAGGTAAAGGGAAATTCCC
TCTACCCTAGGGCCCCTCAGGANCCCTTCCTCTCTCACACGTTTCTTCGACTGCTNNNGATTTAAGCATTCAGCTGGCCAC
GCAACGCAAGAAGCAATAAGAACACAAAAACCCTACCCTGTTCNTCCTCTATCCGTGGCCTTTGCCACCACCTCCACAAC
CTAGTTCAGATTCCTCTTCTTTTCTCAAGGGAACGTCTAAAGCTCTCAAGTCCGTTTTGGCAGGGCGATTTTGTAAGTCTGA
ANCATTTCAGTGTGTCTCTCGATCTCAGGCAGCTCAAAAGAAAAGATCTGCTGGCTGCGTGAAGGTGCATTAGAAACCTG
CTGCTACCTTGCAGCCTGGGCTGAGCATATGCTCCGGAACTTGCTTCTCTTCCAACATCCTGCACCTCAGGGTTGCACGCT
CTGGTTCCCAAGCCCCCGGCCGCTGGCTTATGCAAATCACTTAGGTACATGCAAAAGTATCCCTTCTCCCGGAGCGCCATT
GGCCCGGGGAGGTCTCGAGCTCATTACTATGCAGAGAGGAGAGCCGCCATTGGCCAAGAGGAGGACCAGAGGGGCGTGT
TTCTCGGGCAAATTGGATCTCCTAAATTGGATGACCTGGGCTGAAAGACAACTTAAAGACCCCCAGAAAACTCTGGTTTT
ATAGATAAGAAATCTGAGGCTCGAGAGAGAGTGTGTTCTGCCCAACATCATCACGGAACAGCTCCTGGGCTCCTGGCTCC
TAATCTGTCATCGCTGTCTGGAACAGCGATGACTCGATCGCGAGATCAGGAAGGTGGCCGAGTGTGTCGCCGCGGCCATC
AGGCACTTCTCCTTCCTGCCCTTGTATGAAGAAGGATGTGTTTGCTTCCCCTTGTGCCATGATTGTAAATTTCCTGAGGCCT
CCTCAGCCCTGCAGAACTGGGGTTATAGCCATGTGACTGATCTTCGTCCAAGAATATGTAAAGAAAAAGTGTTGAGTTGG
CTTTTAGGGCTAGAGCAATGTATCTTAGGCTCACTTAAGGAAGCTGTAGAGATGAGCCCAAGGAGGGAAACCAGAAGAG
CCCCCCAGGCTCACCAGTTGTTTGTTGGCTCCCTACAAACATGTCATTCAAGTGGCTAATCTTACAACAGCACAAATTCAT
CTAACCAGAAAGAGAAGAGGAGGCTCCAAAGGCACTTGACTACTGAGCATCACCCTGGACGTGTACAAGTCTGCGTCCTT
ATTGTTTTCTTCATTGGGCCGAACTTTCTGGTCCTCATCCAACAGCTCTTCTATCACGTGTTCGAAAGTGTCAGCCAATGAT
GTCAAGCATCTTGAACCTGCCTTGGGCCCATTCACGCTCTCCAGAGTCCCATGGGTCCGCACACCTGGAGATACTCTATTA
TAGCAAAGAAGAAAGATAATTTCATTGAGCCATCCTGTTTTACAGTATTGAATTATTACCACAAGGTACCAACCATATATG
CATACTTAATAGGGTATTTTGTCAAAACTATGCATGAAGGTCATTTGTTTGAGATGTCAGAACATTTTCCCGTGAGAAGAT
CTCATTGGGCATTGAAACAGAACCACATGCTCTTCAGACCAGCAACCGCGACTACCAAATACTCCTCTGTCAACTCTACTT
GAGTAAGAACGCTTTCAATTAAGGCCTAAGTGTCAACATGCCTTTAAAAAAAATCGTGGTGACACAAAATCTTTCTTTTTA
GCACCCAACAGAATCCCTTCAAAGCCTCGTGGTCTGACACCCTATGCTACGTGACTTGTGACCCATCCATTTGTCATGTTC
TTCGGGAATGTGGCTAAGGGGCTAAGATGTGACTTGAAAAGAAAGGTAGAACAAGATCATCTCAAATTTATTATCAAGGA
ATAGTTCAGAAAACGACTTCAGACCACAGAGACAGCAGAACAGATGGTCCGGCATGGATAGAGCATCAGACACTCACAG
ACTGTGCCAACAAGAGCCATCGAGTCAAAACAGCCAAAGGAAGGAGGGTCATGGAATGGGTTCTCTCACACCAAACTGA
TGCCCAGAGGCCCTCAGCATGAATAACAAAGGCAACCAGACCCACAAGCCATACTGAGTGGATACAAAACCTATACCTA

FIG.3 (Continued)

GGCTGACATCCCAAATGTGTGTGGCAAGTTAGATGATGATGGCACAAAAGACAGAACACCTTGCTTCTGGCCATTGTCAG
CTCTTGGAAGAGAGCACACTTTTAGAGGAGCAGCTGCAAGGAGCCTGAGAACAAAACTGGAAATGTCTGTTATGAAAGC
CTTCACAGGAAATTCTGCAAGTGGCAACGTGGGTCCATTCCGTGTGTGTCACTAGAGCTGGCGCAAGCCCATGGCCATGG
TGAGGCAGCGTTTCCACTGGAACTAATCTGATACCTGCACCAACTCTTGCAACTGTGCAGTGTTCCCACTGCAAACTACGG
ATGGGGTAAAAGACTGCTCACCTCCTATTTCTCATCTAATCTCACACACTCTGTTTGATGAGGCTATGGAGAAACAGGTCT
TCTCATACACTAAAGGTGGGAGTACAAACAATTCAAGCCCTGTGCAGGACAATTAGGCAATACCTATCAAAATTATACAT
GATTTTTCCTGCTGACCCAGCAATTCCACTTTTGGGAATAATTGACAGATATAGGTGCATATGTACAAAATGATGGAAAGC
TCTCTGGTATATATTAGTAAGTGATAAAACAAGGTGTGTGTATATATGGCTACTACCTTTTGTTTTAAAAATGGGGGAAAA
TGGTGGAGCTTGCGGTGAGCCGAGATCGTGCCACTGCACTCCAGCCTGGGCGACAGAGCGAGACTCCGTCTCAAAAAAA
AAACAGGGTGGGGTGGGGGGAAATAATAGTACATACTCATATTTACCTGTATCTATATAAAACACACTATCAAGGATTC
ACAAGAAACTAATACAAATGATCCCCTTATAGATGGTATGTATTGGGGGATACTGAGGTGAGCAGGGTATAAGTGGGGC
AAGACTTTTCAGTGTAAACTTCTTTTAAATTTTATTTTGATTTTTGAATAATGTAAATTAACTGTCAAATAATTAAATTAAA
AATAACCAATTTATTAACAAAAAAAAAAAAAAAAAAAATA

FIG.4

| Sequence ID | Sequence |
|---|---|
| SEQ ID NO :3 | CTTGAATTGT TTGTA |
| SEQ ID NO :4 | AGTTGCAAGA GTTGG |
| SEQ ID NO :5 | ATCTGTTCTG CTGTC |
| SEQ ID NO :6 | CATATTCTTG GACGA |
| SEQ ID NO :7 | TGTGCTGTTG TAAGA |
| SEQ ID NO :8 | TGACAGAGGA GTATT |

FIG.5

| Sequence ID | Sequence |
|---|---|
| SEQ ID NO :9 | GCACACCTGG AGATACTCTA TTATA |
| SEQ ID NO :10 | CCTGCAGAAT GGCCTGGAAT TACAA |

SEQUENCE LISTING

```
<160> NUMBER OF SEQ ID NOS: 11

<210> SEQ ID NO 1
```

<211> LENGTH: 4755
<212> TYPE: DNA
<213> ORGANISM: Homo sapiens
<300> PUBLICATION INFORMATION:
<308> DATABASE ACCESSION NUMBER: NM_170735
<309> DATABASE ENTRY DATE: 2010-07-18
<313> RELEVANT RESIDUES IN SEQ ID NO: (1)..(4755)

<400> SEQUENCE: 1

```
cacacacaca cacacacaca gagagaacat ctctagtaaa aagaaaagtt gagctttctt     60

agctagatgt gtgtattagc cagaaaaagc caaggagtga agggttttag agaactggag    120

gagataaagt ggagtctgca tatgggaggc atttgaaatg gacttaaatg tctttttaat    180

gctgactttt tcagttttct ccttaccaga cacattgttt tcatgacatt agccccaggc    240

atagacacat cattaaaatg aacatgtcaa aaaatgattt ctgtttagaa ataagcaaaa    300

cattttcagt tgtgaccacc caggtgtaga ataaagaaca gtggaattgg gagccctgag    360

ttctaacata aactttcttc atgacataag gcaagtcttc tatggccttt ggtttcctta    420

cctgtaaaac aggatggctc aatgaaatta tctttcttct ttgctataat agagtatctc    480

tgtgggaaga ggaaaaaaaa agtcaattta aaggctcctt atagttcccc aactgctgtt    540

ttattgtgct attcatgcct agacatcaca tagctagaaa ggcccatcag acccctcagg    600

ccactgctgt tcctgtcaca cattcctgca aaggaccatg ttgctaactt gaaaaaaatt    660

actattaatt acacttgcag ttgttgctta gtaacattta tgattttgtg tttctcgtga    720

cagcatgagc agagatcatt aaaaattaaa cttacaaagc tgctaaagtg ggaagaagga    780

gaacttgaag ccacaatttt tgcacttgct tagaagccat ctaatctcag gttatatgct    840

agatcttggg ggcaaacact gcatgtctct ggtttatatt aaaccacata cagcacacta    900

ctgacactga tttgtgtctg gtgcagctgg agtttatcac caagacataa aaaaaccttg    960

accctgcaga atggcctgga attacaatca gatgggccac atggcatccc ggtgaaagaa   1020

agccctaacc agttttctgt cttgtttctg ctttctccct acagttccac caggtgagaa   1080

gagtgatgac catccttttc cttactatgg ttatttcata ctttggttgc atgaaggctg   1140

cccccatgaa agaagcaaac atccgaggac aaggtggctt ggcctaccca ggtgtgcgga   1200

cccatgggac tctggagagc gtgaatgggc ccaaggcagg ttcaagaggc ttgacatcat   1260

tggctgacac tttcgaacac gtgatagaag agctgttgga tgaggaccag aaagttcggc   1320

ccaatgaaga aaacaataag gacgcagact tgtacacgtc cagggtgatg ctcagtagtc   1380

aagtgccttt ggagcctcct cttctctttc tgctggagga atacaaaaat tacctagatg   1440

ctgcaaacat gtccatgagg gtccggcgcc actctgaccc tgcccgccga ggggagctga   1500

gcgtgtgtga cagtattagt gagtgggtaa cggcggcaga caaaaagact gcagtggaca   1560

tgtcgggcgg gacggtcaca gtccttgaaa aggtccctgt atcaaaaggc caactgaagc   1620

aatacttcta cgagaccaag tgcaatccca tgggttacac aaaagaaggc tgcaggggca   1680

tagacaaaag gcattggaac tcccagtgcc gaactaccca gtcgtacgtg cgggccctta   1740

ccatggatag caaaaagaga attggctggc gattcataag gatagacact tcttgtgtat   1800

gtacattgac cattaaaagg ggaagatagt ggatttatgt tgtatagatt agattatatt   1860

gagacaaaaa ttatctattt gtatatatac ataacagggt aaattattca gttaagaaaa   1920

aaataatttt atgaactgca tgtataaatg aagtttatac agtacagtgg ttctacaatc   1980

tatttattgg acatgtccat gaccagaagg gaaacagtca tttgcgcaca acttaaaaag   2040

tctgcattac attccttgat aatgttgtgg tttgttgccg ttgccaagaa ctgaaaacat   2100
```

```
aaaaagttaa aaaaaataat aaattgcatg ctgctttaat tgtgaattga taataaactg   2160
tcctctttca gaaaacagaa aaaaacacac acacacacaa caaaaatttg aaccaaaaca   2220
ttccgtttac attttagaca gtaagtatct tcgttcttgt tagtactata tctgttttac   2280
tgcttttaac ttctgatagc gttggaatta aaacaatgtc aaggtgctgt tgtcattgct   2340
ttactggctt aggggatggg ggatgggggg tatattttg tttgttttgt gttttttttt    2400
cgtttgtttg ttttgttttt tagttcccac agggagtaga gatggggaaa gaattcctac   2460
aatatatatt ctggctgata aaagatacat ttgtatgttg tgaagatgtt tgcaatatcg   2520
atcagatgac tagaaagtga ataaaaatta aggcaactga acaaaaaaat gctcacactc   2580
cacatcccgt gatgcacctc ccaggccccg ctcattcttt gggcgttggt cagagtaagc   2640
tgcttttgac ggaaggacct atgtttgctc agaacacatt ctttcccccc ctcccccctct  2700
ggtctcctct ttgttttgtt ttaaggaaga aaaatcagtt gcgcgttctg aaatatttta   2760
ccactgctgt gaacaagtga acacattgtg tcacatcatg acactcgtat aagcatggag   2820
aacagtgatt ttttttaga acagaaaaca acaaaaaaata accccaaaat gaagattatt   2880
ttttatgagg agtgaacatt tggtaaatc atggctaagc ttaaaaaaaa ctcatggtga    2940
ggcttaacaa tgtcttgtaa gcaaaaggta gagccctgta tcaacccaga aacacctaga   3000
tcagaacagg aatccacatt gccagtgaca tgagactgaa cagccaaatg gaggctatgt   3060
ggagttggca ttgcatttac cggcagtgcg ggaggaattt ctgagtggcc atcccaaggt   3120
ctaggtggag gtggggcatg gtatttgaga cattccaaaa cgaaggcctc tgaaggaccc   3180
ttcagaggtg gctctggaat gacatgtgtc aagctgcttg gacctcgtgc tttaagtgcc   3240
tacattatct aactgtgctc aagaggttct cgactggagg accacactca agccgactta   3300
tgcccaccat cccacctctg gataattttg cataaaattg gattagcctg gagcaggttg   3360
ggagccaaat gtggcatttg tgatcatgag attgatgcaa tgagatagaa gatgtttgct   3420
acctgaacac ttattgcttt gaaactagac ttgaggaaac cagggtttat cttttgagaa   3480
cttttggtaa gggaaaaggg aacaggaaaa gaaaccccaa actcaggccg aatgatcaag   3540
gggacccata ggaaatcttg tccagagaca agacttcggg aaggtgtctg gacattcaga   3600
acaccaagac ttgaaggtgc cttgctcaat ggaagaggcc aggacagagc tgacaaaatt   3660
ttgctcccca gtgaaggcca cagcaacctt ctgcccatcc tgtctgttca tggagagggt   3720
ccctgcctca cctctgccat tttgggttag gagaagtcaa gttgggagcc tgaaatagtg   3780
gttcttggaa aaatggatcc ccagtgaaaa ctagagctct aagcccattc agcccatttc   3840
acacctgaaa atgttagtga tcaccacttg gaccagcatc cttaagtatc agaaagcccc   3900
aagcaattgc tgcatcttag tagggtgagg gataagcaaa agaggatgtt caccataacc   3960
caggaatgaa gataccatca gcaaagaatt tcaatttgtt cagtctttca tttagagcta   4020
gtctttcaca gtaccatctg aatacctctt tgaaagaagg aagactttac gtagtgtaga   4080
tttgttttgt gttgtttgaa aatattatct ttgtaattat ttttaatatg taaggaatgc   4140
ttggaatatc tgctatatgt caactttatg cagcttcctt ttgagggaca aatttaaaac   4200
aaacaacccc ccatcacaaa cttaaaggat tgcaagggcc agatctgtta agtggtttca   4260
taggagacac atccagcaat tgtgtggtca gtggctcttt tacccaataa gatacatcac   4320
agtcacatgc ttgatggttt atgttgacct aagatttatt ttgttaaaat ctctctctgt   4380
tgtgttcgtt cttgttctgt tttgttttgt tttttaaagt cttgctgtgg tctctttgtg   4440
```

```
gcagaagtgt ttcatgcatg gcagcaggcc tgttgctttt ttatggcgat tcccattgaa   4500

aatgtaagta aatgtctgtg gccttgttct ctctatggta aagatattat tcaccatgta   4560

aaacaaaaaa caatatttat tgtattttag tatatttata taattatgtt attgaaaaaa   4620

attggcatta aaacttaacc gcatcagaac ctattgtaaa tacaagttct atttaagtgt   4680

actaattaac atataatata tgttttaaat atagaatttt taatgttttt aaatatattt   4740

tcaaagtaca taaaa                                                    4755
```

<210> SEQ ID NO 2
<211> LENGTH: 3175
<212> TYPE: DNA
<213> ORGANISM: Homo sapiens
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (104)..(104)
<223> OTHER INFORMATION: n is a, c, g, or t
<220> FEATURE:
<221> NAME/KEY: misc_feature
<222> LOCATION: (137)..(139)
<223> OTHER INFORMATION: n is a, c, g, or t
<220> FEATURE:
<221> NAME/KEY: misc_feature
<222> LOCATION: (206)..(206)
<223> OTHER INFORMATION: n is a, c, g, or t
<220> FEATURE:
<221> NAME/KEY: misc_feature
<222> LOCATION: (326)..(326)
<223> OTHER INFORMATION: n is a, c, g, or t

<400> SEQUENCE: 2

```
cngcnnaaag atttcttcac agggtccttt aaactgtcnn tttntaagag gtccttccac     60

tacaggtaaa gggaaattcc ctctacccta gggcccctca ggancccttc ctctctcaca    120

cgtttcttcg actgctnnng atttaagcat tcagctggcc acgcaacgca agaagcaata    180

agaacacaaa aaccctaccc tgttcntcct ctatccgtgg cctttgccac cacctccaca    240

acctagttca gattcctctt cttttctcaa gggaacgtct aaagctctca agtccgtttt    300

ggcagggcga ttttgtaagt ctgaancatt tcagtgtgtc tctcgatctc aggcagctca    360

aaagaaaaga tctgctggct gcgtgaaggt gcattagaaa cctgctgcta ccttgcagcc    420

tgggctgagc atatgctccg gaacttgctt ctcttccaac atcctgcacc tcagggttgc    480

acgctctggt tcccaagccc ccggccgctg gcttatgcaa atcacttagg tacatgcaaa    540

agtatccctt ctcccggagc gccattggcc cggggaggtc tcgagctcat tactatgcag    600

agaggagagc cgccattggc caagaggagg accagagggg cgtgtttctc gggcaaattg    660

gatctcctaa attggatgac ctgggctgaa agacaactta aagacccccca gaaaactctg   720

gttttataga taagaaatct gaggctcgag agagagtgtg ttctgcccaa catcatcacg    780

gaacagctcc tgggctcctg gctcctaatc tgtcatcgct gtctggaaca gcgatgactc    840
```

```
gatcgcgaga tcaggaaggt ggccgagtgt gtcgccgcgg ccatcaggca cttctccttc    900
ctgcccttgt atgaagaagg atgtgtttgc ttccccttgt gccatgattg taaatttcct    960
gaggcctcct cagccctgca gaactggggt tatagccatg tgactgatct tcgtccaaga   1020
atatgtaaag aaaaagtgtt gagttggctt ttagggctag agcaatgtat cttaggctca   1080
cttaaggaag ctgtagagat gagcccaagg agggaaacca gaagagcccc ccaggctcac   1140
cagttgtttg ttggctccct acaaacatgt cattcaagtg gctaatctta caacagcaca   1200
aattcatcta accagaaaga gaagaggagg ctccaaaggc acttgactac tgagcatcac   1260
cctggacgtg tacaagtctg cgtccttatt gttttcttca ttgggccgaa ctttctggtc   1320
ctcatccaac agctcttcta tcacgtgttc gaaagtgtca gccaatgatg tcaagcatct   1380
tgaacctgcc ttgggcccat tcacgctctc cagagtccca tgggtccgca cacctggaga   1440
tactctatta tagcaaagaa gaaagataat ttcattgagc catcctgttt tacagtattg   1500
aattattacc acaaggtacc aaccatatat gcatacttaa tagggtattt tgtcaaaact   1560
atgcatgaag gtcatttgtt tgagatgtca gaacattttc ccgtgagaag atctcattgg   1620
gcattgaaac agaaccacat gctcttcaga ccagcaaccg cgactaccaa atactcctct   1680
gtcaactcta cttgagtaag aacgctttca attaaggcct aagtgtcaac atgcctttaa   1740
aaaaaatcgt ggtgacacaa aatctttctt tttagcaccc aacagaatcc cttcaaagcc   1800
tcgtggtctg acaccctatg ctacgtgact tgtgacccat ccatttgtca tgttcttcgg   1860
gaatgtggct aaggggctaa gatgtgactt gaaaagaaag gtagaacaag atcatctcaa   1920
atttattatc aaggaatagt tcagaaaacg acttcagacc acagagacag cagaacagat   1980
ggtccggcat ggatagagca tcagacactc acagactgtg ccaacaagag ccatcgagtc   2040
aaaacagcca aaggaaggag ggtcatggaa tgggttctct cacaccaaac tgatgcccag   2100
aggccctcag catgaataac aaaggcaacc agacccacaa gccatactga gtggatacaa   2160
aacctatacc taggctgaca tcccaaatgt gtgtggcaag ttagatgatg atggcacaaa   2220
agacagaaca ccttgcttct ggccattgtc agctcttgga agagagcaca cttttagagg   2280
agcagctgca aggagcctga gaacaaaact ggaaatgtct gttatgaaag ccttcacagg   2340
aaattctgca agtggcaacg tgggtccatt ccgtgtgtgt cactagagct ggcgcaagcc   2400
catggccatg gtgaggcagc gtttccactg gaactaatct gatacctgca ccaactcttg   2460
caactgtgca gtgttcccac tgcaaactac ggatggggta aaagactgct cacctcctat   2520
ttctcatcta atctcacaca ctctgtttga tgaggctatg gagaaacagg tcttctcata   2580
cactaaaggt gggagtacaa acaattcaag ccctgtgcag gacaattagg caatacctat   2640
caaaattata catgattttt cctgctgacc cagcaattcc acttttggga ataattgaca   2700
gatataggtg catatgtaca aaatgatgga aagctctctg gtatatatta gtaagtgata   2760
aaacaaggtg tgtgtatata tggctactac cttttgtttt aaaaatgggg gaaaatggtg   2820
gagcttgcgg tgagccgaga tcgtgccact gcactccagc ctgggcgaca gagcgagact   2880
ccgtctcaaa aaaaaaacag ggtggggtgg gggggaaata atagtacata ctcatattta   2940
cctgtatcta tataaaacac actatcaagg attcacaaga aactaataca aatgatcccc   3000
ttatagatgg tatgtattgg gggatactga ggtgagcagg gtataagtgg ggcaagactt   3060
ttcagtgtaa acttctttta aattttattt tgatttttga ataatgtaaa ttaactgtca   3120
aataattaaa ttaaaaataa ccaatttatt aacaaaaaaa aaaaaaaaaa aaata        3175
```

<210> SEQ ID NO 3
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 3
cttgaattgt ttgta 15

<210> SEQ ID NO 4
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 4
agttgcaaga gttgg 15

<210> SEQ ID NO 5
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 5
atctgttctg ctgtc 15

<210> SEQ ID NO 6
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 6
catattcttg gacga 15

<210> SEQ ID NO 7
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 7
tgtgctgttg taaga 15

<210> SEQ ID NO 8
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 8
tgacagagga gtatt 15

<210> SEQ ID NO 9
<211> LENGTH: 25
<212> TYPE: DNA
<213> ORGANISM: Artificial Sequence
<220> FEATURE:
<223> OTHER INFORMATION: Assay sequence

<400> SEQUENCE: 9
gcacacctgg agatactcta ttata 25

<210> SEQ ID NO 10
<211> LENGTH: 25
<212> TYPE: DNA
<213> ORGANISM: Artificial Sequence
<220> FEATURE:
<223> OTHER INFORMATION: Assay Sequence

<400> SEQUENCE: 10
cctgcagaat ggcctggaat tacaa 25

<210> SEQ ID NO 11
<211> LENGTH: 46159
<212> TYPE: DNA
<213> ORGANISM: Homo sapiens

<400> SEQUENCE: 11
gtaaaccaat agcccccatg ctctgtgcga tttcattgtg tgctcgcgtt cgcaagctcc 60
gtagtgcagg aaggtgcggg aaggtgtgtc tgtggcccgg gaaacgcacg ccctctccca 120
gagaacttgg gtgctgggat ggggaggaag gggagagttg aaagctaggg gagcgagacc 180
tcggggcgtg cgattctcac tcgctccctc ccgccccagc gcccacagcc ggggtttctg 240
cagagggcgc gggacgcggg gttccccggg gctgaggctg ggctggaac acccctcgaa 300 gccgcgggcg tcctgtccaa ggcgccccag gagggcgcag gactcgcagg gcgatgtcgc 360
ggggccctag gggaggaggt gaggacaggc cccgggggag cggggagttc cgggcgcccc 420
tcggttcccc gcgcgaggaa aagacgcggc gttcccttta agcggccgcc tcgaacgggt 480
atcggtagcg cgggcgagcg gggagcgggg ggcgggggc gggggggggg gggcggcgcc 540
gtttgaccaa tcgaagctca accgaagagc taaataatgt ctgacccggg cgcaaggcgc 600
agcctggagc tccgggtccc cgacgctgcc gccgccgcgc ccgggcgcac ccgcccgctc 660
gctgtcccgc gcaccccgta gcgcctcggg ctcccgggcc ggacagagga gccagcccgg 720
tgcgcccctc cacctcctgc tcggggggct ttaatgagac acccaccgct gctgtggggc 780
cggcggggag cagcaccgcg acggggaccg gggctgggcg ctggagccag aatcggaacc 840
acgatgtgac tccgccgccg gggacccgtg aggtttgtgt ggaccccgag gtaggcaagc 900
gctgggaatg gggcttggtg caggagctgc ccgtccgcgg gagagagttg actgggggat 960
cccccacccc aaagttgtgg gacgaggcca gtctccttct ttcctcccct ccggtagaag 1020
ggacgatttg gagttactct tggggagttt tctcccccat cccacaaccc agaaggtcag 1080
ccggcaccac cagggaaaaa gggacccggg gaagtcacga agtagaggag ggaaggcctg 1140
gaggagaccc agagctgcgt gatgggagca aagacggcga cccggggatc cctcgcagcc 1200
ctcccccagc ccaggagtag tcgagagaga cttagggggc cagagctgtc gagggtcctg 1260
actgagggga gggtgctggg gctaggctag gaatccttcc agggggtggg tggtccccgc 1320
gccgacttgc ggggggagtg ggagggaagc ttgcgccttc agcccgcatc ccttccccgg 1380
agctgcacac ggctacctgc tccccaggaa ttgagactga agtggactta caagtccgaa 1440
gccaatgtag cttggaaaac ttgggaggcg gaattcctac cgctgggaac tgaaagggtc 1500
tgcgacactc tcgggcaggc cgaacccaca tctctaccca tcctgcgccc ctcttctgaa 1560
gcgccctcca gggaagttaa gagttttgac tttcggggag tggttgggat gtacgtgggg 1620

-continued

```
gattcttgac tcgggttagt ctctggggat gcagagccgg gaagaggaat gggtgagtga   1680
gttactcctg gaaagaaata gctgaggatt gggggctctg tgcctgacgg gcaagaagaa   1740
ggggagatta cagactaggg gcatccctaa ggaagaagcc tcggggctgc gagggtgaac   1800
tggaggatgc agtgtttgtg tgttgggggt agagcgggga tgagggaccg gggtggaggg   1860
gaggcgagga ggaggagggg acccagagaa cgaagctagg gaaggtagag ggtgccctct   1920
gccggccatg ctgccaagag cagctactgg gggcgggagg ctgggggtgg ggaagtggta   1980
aaggaaggtt ttgcgggatc ccttagagag ctggtaggag ggacttgttg aatggtgctg   2040
ctgactccag ctcggtgggg cgtgcgactc gtcgtcggtg gattttgact cctcgttctt   2100
gtttggcttc tatgcaagtt ttcctcgcgc tgggggagct ttgataagcc tcgattggcg   2160
gtgtgttagg gcttcttgga tcttatttta gggtcctcta gttatcctgc acttactcct   2220
taatgtcagt agcaaccaaa gaacattttc cgacaagcac gcaggaatgt tcttggccag   2280
aagcaaagaa aggcatattt ctgagtgttt attaatcctc ctagtaatct tttaaagcaa   2340
agtaatatgt aattgggaac gttgattttc taactgcata taaaaggcga catgatatta   2400
aatgagaccc ctccctactg actcaatatc ctgcaaaatc tctctctccc ctttattatt   2460
atggaaaaat ctatttttat atgagtttgt tgtaaggtca aaagccattt tggtcttaca   2520
atttgatatg tctttacatt ttaacttatt gaggcataat tacagattta atttgtatga   2580
acgtgtgtgc cttcaatgct tatctcatgc aacataattt ttaggttgga gatttctgat   2640
gttatggcat gtagcgtttc aaggcattac acataatagg taacatagca tgttgaaatt   2700
acaccacaaa gttttgaccc tgggaacagc accttttaaa aacaatcact aaactcctgt   2760
tcctgttttc tgattttgca aatgccttgc ttaagacttt tttttttttt tttttttttt   2820
tttttttggg aaatttacct ctgggttagc aggagaggta aaaaaaagga aagagacact   2880
tgttgaaatg taaccataac ctttactgga atttaaaaca tgttggtcac cattactgga   2940
attccagggc cataaagtcg ttgtcttttt tttcttctac ttcattttgt aaaatgtgat   3000
aaatgttggt aaatatagac cagtagtaag tattatgaca ctaaaagcat tatgtatgtg   3060
gaactatttt aagttattac agaacatttt ctatttataa atgatataag cagaaagaaa   3120
tgatttccag ataaacaagg cttacgtaca tgttttgaag cattagaaca ttgcagacac   3180
tcttagacat cacatttttt aaagcaaaat aacagtaatt tttcacatac ctttggagcc   3240
tttcatagcc cattcagagc tgagttagta gctggaagtt tcctttattt taaggtgata   3300
ttttaaaacc atttaacatg tatagtaggt caacattggt gcatccagaa aatgaagcat   3360
ttaggaaatc tgtttcagtg tcttttcaat gtgtgtaact tttacttgca aaccaatgga   3420
accaagaaag tcatcatttg cctaaaatgc agtcatcacc tcaaatgatt catttatact   3480
atgtgagtta attgccttca tctcattaat ggccaaggag ggaagggagg tcctggggta   3540
tttcttgttc attttgactc accaggaggg aaaatcctgt aaaaaaagaa atgcaaattt   3600
ctaaaatcct ggctcaaagt ccgtgggttt cctgtttaaa aggggcgcca tgaaaatgta   3660
agctattccc tttttcctgg aatctttaag agtcccagct tttcaatagt caaaatgtag   3720
atgattgata tcatttctta tatgaatagc actggtttgt agttcagcac gcacagtgag   3780
ctgggcacgc ccacctgata gtatagcaga gaacttgttt acattctttt tacattcatc   3840
ttctaaaacc tggggtgctc tctctctctc tctctctctc tctctctctg tgtgtgtgtg   3900
tgtgtgtgtg cgtgcacgtg cgcgtgtgtg tagaggggga gagagagaga gagagaactg   3960
tgaactgtga aatataacac agccagcagc tttgggtctc aatcgtagac ttactcttaa   4020
```

-continued

```
ggaaatttac agaatggaaa ggtcatgttc aagtagttta ttaacatttt gagatgtagg   4080
aaattaatcc cggagtacag aagaacaatt tcagacttcc tgaataaaaa cagacagcat   4140
agagagtgga tgatagctaa actctgaata tcttttgaga agaaaggcac tcccatttca   4200
ggtgcccata atatggattt gattttagtg attaaaacat taattttcaa cttgcatctc   4260
cctgtgtgga agagttcaat ttgtgtgagg ggtctcgcct atccaacaaa agtgaatatg   4320
tccctttttat agggtaattg ctaacttgtc tcaacttgtt ttcaaacaat tgttatagag   4380
cactcagttt ccactaattg caaaattgtt gcttaattga aggactctca gccatctagt   4440
gcagccattc agccactggc aggctctgtg atctcaaact gtgaattgca ttttaaagag   4500
gaatcgagga gagaattctg tggaattcta ggttttaagt gctggctgtt gttcaatgga   4560
agaggaaatc atttgaacaa gaatcgcatc aagttgtgtt gtgataaatt ttctttatta   4620
ggatgaataa catgcacaga tgagcttcaa aagtgaatga gcaaacttac tggttacact   4680
ctgcatccat ttactctgtt tagtatggag taatgttagg caataaatga tgctggcaaa   4740
tgaaatccgt atgttatttg catgtggtat ttaaacctag gaaacataga gtggctttgg   4800
tatttgtagg cttagtcatg tgtgtcctaa acgtcctctt aaacttctac ttaaggcata   4860
gaattattta atcctaaata attttatact taagtgcctc actggatttc cagaatattt   4920
acactgtaaa gatttagaaa ggtcatgaac ccaattattg actatatgga atcattattg   4980
atggcagatg caaaatggag ctcactaatg tactgacatt gaaaaccttt tgcaggggag   5040
aggaggggga gtggtaaatg tgtgtgttct ttaagtggaa caggaaggta ttctcttttc   5100
tgtagaaaaa tttgagtatc tggtcagata agtgtggaag ctttcattta aattaagtat   5160
ttaagttcaa gtagaagctc tagggcactt atcctcttga tgagacaaat cttatcaaat   5220
atactagatg ctaagaagtg gctcattgcc ctgatgtctc atttatagat tgatgtttga   5280
ggatgggttg cattaagtga gttagggggc tgagtgtggg acaggagaac gattggaagg   5340
aagcaaagta aatttacaag ctttagtgac agccataata aagtaaaagt ttatttccag   5400
agagcctaga gagtaaggaa cgttatatag ttttccccaa aggttcactt gaaagaactt   5460
ttcattggtt gtcatggtag taatgtcctg attttgaaat ctcccagaac ctagtagctc   5520
ttaaacatgc tttcatcttg gttcctttgg tctgacggaa actttatgac gaccctctgt   5580
gtttttgaca tgcctctgca tttttggaga gaggaggtca ggcaagggag gatttcttaa   5640
aactaagaca gtatagtaag gaaacataaa attatatgat aaaaaatcac tgaacttcaa   5700
attgacttac tgaaataaaa cctagaaggc aacctgtcgt ttaattacaa ctagcttgta   5760
taaaattaaa atttataaaa tgggaattca aagaaaataa acgggcagtt ccaagtaatt   5820
taagcaactc accaaaaatt gaagtaatag tgccacctag agaacaaaat caccagcttt   5880
actagccaaa tggcttattt ccatatgaac catttttcca acgctacagt tactaggatt   5940
tccttgttac catattcaga tcttgtgagt gtgtatgggg gtgggggttg catgtggaat   6000
tacagatgaa attttaaaac aagcagatcc acaatttgat atatgcacta aatcctttta   6060
acgttgtaat gtagccaaat gtagaatagc atgccaggaa tcaacggcta gcatcctttt   6120
taacatttat tattttcatg gatatgtacc aaaccgaacc attgagtata aaggttctga   6180
ttttatttat ttgctacagg caattcatta tactttctga gatacaataa caccaaataa   6240
tttgagtaga gagaccttta agaatgtttt cgatttatga tctaccttta actttaatgt   6300
actcagaaga tgtgagaata aaataaagtc aaatataagc aagattttaa acacacacac   6360
```

-continued

```
aaaaaacaaa caaacaagaa aaaggaagaa aattataagg attgccttaa ccttagaata   6420

gatgaaggta tacatctgag ccagcaccaa aaaaaaaaaa aaaaaaagtt atggaaccag   6480

gaaccaataa ttacaaattg acttaaaatt cttggatgac aaaaatctat atttagttca   6540

tttttgcatg cgcccacaac agcatccaaa acagttctgg ggaggcactt tgataaatgt   6600

tgctgaatgc actaatagat tgattaatgg ctgcttcaga ttatcactag tgatgtagac   6660

agaaacttca tgaaaatggt ttgtcttgct ggaagaaagg cagaaattgg aggaaaaggt   6720

ttaataatat ttttccccag tacctattat aaaagtcatt tagttggctt agttctataa   6780

tttcttatgt gtaatttgat tcacttatga aattgtgaat atatgaaatg ttaaagttga   6840

tttagacagc aactataagc ttgtggattt tcttttaaat gtcttcaaat ttttaaatgc   6900

cagtggagat gccagcgact gtgcttcagg gagtagaata tagtatatct taaatttgtg   6960

ccaatttctg gtaagcagag aaaaaattgc atgataacca aagaaagtca tattgtttgt   7020

gctttgtgtt attcatggaa gcaatcaggt gcagaaaact ttctttttca gaaaaaaaaa   7080

attactaaaa taaaggtgcg tgtgtgtgta tgcacatata tctaaaggga gagagggaga   7140

aggaaactta ctaaataaaa tttttgccac atgggattta gtctaatcag tcttggtttt   7200

ggagttgcta tcatcagtag ttccattttg tgattctttc tttctgcctt catgtgcctt   7260

tgaaaactga aactatgccc aaattaaaac aagtttttct gtcttttcac atgttcactt   7320

atttcttgaa tgtgttttta aacacagaca aacttctttt acatcatgta gaatctgaag   7380

gtcgagaaat ttgcagtcat tttgctggag agagatgctt ggcggagtcc caggccacat   7440

tcctaggcca aactctcgaa ggtattcctc ttatgcaaca ttgggaaaat acatccagca   7500

ccgacatgtt ggctgataat gtgtctgaag gcacagacga tatgcttatc atatgaaaca   7560

taaagccagc agatattgca gacattctgt tgaatgatag aatctggatc atttacattt   7620

acttaaatgt aaaatactat gattaagtac aaaaaaatca atttaggaga gaatagagag   7680

ttgcgggcac ggttttaggg gatgacttat cagcagattg tagaaaggaa gcttgaatgt   7740

tttaaattaa ctgcaagttc agtataagcc agtggtgtga caagaggctg ttatcatagc   7800

tactgaaatt ttgggctgca ctgctagaaa tataatactg aaatggagaa gctaataatt   7860

cttcactttt taaatagact gtatctagaa tattatcatc agttcaagga aatgaaataa   7920

gttgttttag gtacatcatc gataaattag tgtacattca aatcactgtg accaggatgc   7980

atagggaatt tgaaagcatt gcatgtgagc aatggttgag gggacttgga atgcatgact   8040

tagggacaag aaaacttagg ctggaatggc aagtggtttt tgaatgttgg gttgagaaga   8100

attctaaaac tgtgaaggat tagtaaaaat aacattcaga ttgctaatgc ctactgtggc   8160

tgggagatta gagtgtcaac atgtgtgatg tatttttgac atccttattt tgaggatggg   8220

cttcaaagat ttgacgaact gtcataagtg taatttgtgt tgcttcagac agcagttcta   8280

gaaccaatga tgtaaattta gatactctac atggtagtta gaaaactttc cattaattta   8340

atttagcaaa tattgaatgc tcactgcata cagagcactt tattagagga atatataata   8400

aagaaaaaag aggtctggtg tggtggctca tgcctgtaat cccagcactc tgggaggctg   8460

aggtgggagg atcacttgag cccaggagat cattacgagt ctggacaaca tagcaagacc   8520

ccatctttac aaaagacaaa aaaaattatc caagcctggt gacaggcact tgtagtccca   8580

gctacttggg aggctgaggc agtaggatcg tttgagccca ggaggttggg gctgcagtga   8640

gccgtgattg tcccactgct cttcagcctg ggtgacagag tgagaccccg ttggagggaa   8700

ggaagggaag gaaggaagaa aggtaggaag gctgaaatga aaccctttta gaaatgacac   8760
```

```
taaaatggga ggttggagta aggtattttc tgaagtgcct ttgtacttgt ttttttctaa   8820
tgcattggcc ataagtctgc tccttattta tagtccataa acaatcctaa tgagaacagt   8880
tatatatttc tgcctttgaa tcatctactt gaagtgttta gcatcatgaa ttgagtatca   8940
gaaatccctc ccatttcttt gcaaagcgct gtattttact tttccttatt tgtatacaga   9000
ttctcaaaat tggctatttt tcctttgggt tagacagaac agaatgtctg gaaaaaaaag   9060
ttcttatcaa attcaggtgc ccaaattgct taagaaatta acttttgagg ttatattttt   9120
ttagggttca gtagctaaac taagaaaact tctcaccgtt caccttcact tttggaaacc   9180
acaaaatctt cagatattac agttttccaa agagtttctc tttttaaata taaactaaaa   9240
ggaattgact cctcccccaa ctccctcagg cctcagcatg gatagagtta ctttttttct   9300
ttaataattt atttataact tattttgctc ttctgtagaa cagctggaga ttaagcaaca   9360
tggccatgac ataaaatgca agttagacca taagatgagc agcccactcc aagtatgaat   9420
gagtacttat tctttgtgat ctctcatact gcttttaggt attaatagtg tcagtcagca   9480
aagcaaacag tttaatattt acatctcctt taggatatca tatagtttat agtttgtatg   9540
tgttcttgcg tgtatgtttt cttctgtttc aaattctttt ttcttaaagt aagaatgtta   9600
tatgtagcaa atggttcttt cattaattca tttgttaatt caccgtgcat taattgagtg   9660
cccagtgagt gtcaggcact gggctacttg gatttctttt ccctgtattg atccatatat   9720
cttcaggtgc tccttgatat ggctctccat tgactctctc atataaggct ttcattacct   9780
attcacatac tccctcccaa agaggactgg tccaaaagta aaatcttgag caagttctct   9840
gagttatttc agaacttctt gcccccaaac tgtattttta attattgact ggtagcattt   9900
tggaataact tacctctctt ttttaaagat tgaagttctt tatcctctct gattttcagg   9960
tgtcagtttg tgtacaaatt gagacaataa aaatgtttgt tagacatttt cttaaagcat  10020
tttgctatgt gagaatcttt catgaagaac tctttttaac aatgactcta tagcagaagc  10080
cacagtagag ggagaactac tgaatcaaag atggtgtttg agtctatgat tttatgatgg  10140
attttttttt tttttacata caaggatatg catgggtctt ttagtattca ggaatctgtt  10200
cttcacttga cagtatttat aaattgtgtg tttcccccta aaaaaactta aattgtgaga  10260
atgcttccat ttactagaag ttggttaatg attatgccaa ataaggaaaa taagacagaa  10320
aaatcagttt agtgaatact attttgcctt taaatttagt aatttagtaa cagtatctct  10380
ttggggttta ctagaaacca ctttttaatc caataggtct ctttcattgt gaagtcagga  10440
ggtgattttg cttaaatgtg tagtatagga atctatatgt ggtgttcaag gatcatgtaa  10500
atatgctgat ataatcggag cacagtttgg catcattaac tcagaaatat ttaaactctt  10560
gctatacaac atggaagcaa acttgtgcat agtttgtgtg tgtgtgtgtg tgtgaatctc  10620
aaaaaaagaa aaaaatcaca ggatcaggaa gtcggaatag gtcccacttt tcttctagta  10680
ccaaacctac agccatgttc ctagccttct cttttactcc caagcaagac agacaggcaa  10740
atgaccatcc tgctgcccat ttctgtgtat attcacttgc attgagagtt gtattcacct  10800
gcttgttgag agtattcaca aatggtacct gataaagtag atacttcttt aaacatgtga  10860
atttttttgc attgtataat gtttagaaat aatcatgtat aaatggttga atattaatac  10920
aggattgcct tatcaagtat tttattaatc attaaaatgt ggtgtcatta atacaattta  10980
ttttaagtgc ttttcctaaa ataccagatt atttttctga ttttcacatc cctgacaatg  11040
actttcttaa acttggtagc caggaacaga aaacctaaca ctgcatgttc tcactcataa  11100
```

```
gtgggagctg aacagagaga acacatggac tcagggaggg gaaccacaca cactggggcc  11160
tggagcaggg ggcaggggaa gggagagagt gcgtcaggac aaacagacaa atagctaatg  11220
catgcgagcc ttaataccta ggtgatgggt tgataggtgc agcaaaccac catgacacat  11280
atttacctat gtaacaaacc tgcacattct gcacatgtat cccggaactt aaagtaaaat  11340
aaaaaataat aataaaataa aataaactta gtagcatcta ttgttccaga gcctgtaatt  11400
gctcttcagg cagtctcaca taaaaaccta ggagaacctt cactgtcact gttccatgag  11460
gtgttaggaa aacttgctct actgcagtgc cccagtaggc attggtactg agaccaaaat  11520
tcagctggtt tgttgttact acgattccta cgtgatttca cttgtcatgt agacaagatt  11580
gcacacttca ataataatct tgtccaaatg tgtggtattc catacatttt taaaatgcat  11640
tcacatatct cattccattt gatcctacaa ataactctat aaaaaagatt ggcagacatt  11700
atttctatat aacagaggag gaaactggag cttagagaag ctaaatagca atccaaaatg  11760
cacagctgta gaaccagagc aaggatgata gcccagtgac ttcacctaac ctagtcccct  11820
taccaccact ccagctgtct ataaccaaaa cctgcagtat tcaagtaaga aaccatatct  11880
tgcccttgat gcattaatgt gagacctgga gcaggaacag gctgatattg tcaccctggc  11940
ctactgtcca cctttgtctc cagcagagac tggtaccctt ctgtgtgcca aggaataaag  12000
tggtaatggg aagattaaaa atgtttttc caaggagttt tttaatttaa ttttttaaa  12060
aaagaaaaaa ctcttagagg gaaaaatgaa tatatgactt ttgatgtatt gttccttagt  12120
aacttagtta taattttact taaacctgag actcttgcta agtgaatgat tagaaatatt  12180
aggtggctgg ccagatggca aataggaaca gctgcagtct gcagctccca gagagatcaa  12240
tgcagaaggt gggtgatttc tgcatttcca actgaggtac cgggctcatc tcattgggac  12300
tggttagaca gtgggtgcag cccatggagg gtgagccaaa gcagggtgga gcattgcctc  12360
actcaggaag cgcaaggggt caggggaact ccctccccta gccaagggaa gccctgaggg  12420
actgtgccat gagggacagt gctatctggc ccagatacta cacatttcct acagtctttg  12480
cagccggcag accaggagat tcccttgggt gcctacacca ccagggccct gggtttcaag  12540
tacaaaactg ggtggccatt tgggcagaca cccagttagc tgcaggagtt ttttctcata  12600
ccccagtggc acctgaaatt ccagtgagac agaaccattc actcccccgg aaaggggctg  12660
aaggccaggc agccaagtga tctagctcag cagatcccac ccccatggag cacggcaagg  12720
taagatctgc tggtttgaaa ttctcactgc cagcacagct gcctgaagtc aacctgggat  12780
gctccagctt ggtcgggga ggggcatccg ccattactga ggcttgagta ggctgttttc  12840
ctctcacaat gtaaacaaag ccactgggaa gtttgaactg ggtggagcct accacagctc  12900
agcaaagccc ctgtagccag attgcctctc tagattctcc ctctctgggc agggcatctg  12960
ggaaagaaag gcagcagccc cagtcagggg cttatagata aaactcccat ctcatgggac  13020
agagcacctg ggagaggggg tggctgtggg cccagcttca gcagacttaa atgttctttg  13080
cctgttggct gtgaagagag cagtggatct cccagcacag cacttgagct ctgctaaggg  13140
acagactgcc ttcttaagca ggtccctgac cctcgtgatt cctgagtggg agacacctcc  13200
cagcaggggt cgacagacac ttcatacagg agagctctgg ctggcatctg gtgggtgccc  13260
ctctgggaca aaccttccag aggaaggaac aggcagcagt ctttgctgtt ctgcagcttc  13320
tgctggtgat acccaggcaa acagggtctg gagtggacct ccaccaaatt ccagcagacc  13380
tgcagcagag gggcctgact gttagaagga aaactaacaa acaggaatag catcaacatc  13440
aacaaaaagg atgtccacac gaaaaccccg tacaaaggtc gccaacatca aagatcaaac  13500
```

```
atagataaat ccacaaggat gaggaaaatc cagcacaaaa aggctgaaaa ttccaaaaac  13560
cagaatgcct cttctcctcc aagggagcac aactctttgc cagcaaggga acaaaactgg  13620
atggagaatg agtttgatga attgacagaa gtatgcttca gaaagtgggt aaaaacagac  13680
tcctccaagc taaaggagca tgctctaacc caatgcaaag aagctaagaa ccttgaaaaa  13740
aggttggagg aattgctaac tagaataact agtttagaga agaacataaa tgacctaatg  13800
gagctgaaaa acacagcacg agaactctgt gaagcataca caagcttcaa taactgaatc  13860
gataaagcag aggaaaggat atcagagatt gaagatcaat ttaatgaaat aaagcatgaa  13920
gacaagatta gagaaaaaaa gaatgaaaag gaaggaacaa agcctccaag aaatgtggga  13980
ctatgtgaaa agaccaaacc tacatttcat tggtgtacct gaaagtggcg gggacaatgg  14040
aaccaagttg gaaaacactc cttaggatat tatccaggag aacttcccca aactagcaag  14100
acaagccaac attcaaattc aggaaataca gagaacacca caaagatacc cctcaagaag  14160
agcaaaccca agacatgtaa ttgtcagatt caccaaggtt gaaatgcagg aaaaaaagtt  14220
aagggcagcg agagagaaag gtcgggttac ccaaaaaggg aagcccatca gactaacagt  14280
ggatctctca gcagaaaccc tacaagccta caagccagaa gagagtgggg gccaatattc  14340
aacattctta aagaaaagaa ttttcaaccc agaatttcat atccagccaa ctaagcttca  14400
gaagtgaagt agaaataaaa tcctttacag acgagcaaat gctgagagat tttgtcacca  14460
ccaggcatgc cttacaagag ctcctgaagg aagtactaaa taaggaaagg aaaaaccggt  14520
accagccact gcagaaacat accaaattgt aaagaccatt gaaactatga agaaactgca  14580
tcaactaatg ggcaaaataa ccagctaaca tcataatgac aggatcaaat tcacacataa  14640
caatattaac cttaaatata aatgggctaa atgccccaat taaaagacca cagactggca  14700
aattggataa agagtcaaga cccatcagtg tgctgtgttc tggagaccca tctcacatgc  14760
aaagacacac ataggctgaa aataaaggga tggaggaaga tctaccaagc aaatggaaag  14820
caaaaaaaaa gcaggggttg caatcctagt ctctgataaa acagacttta aaccaacaaa  14880
gatcaaaaga gacaaagaag gccattacat aatgataaag ggatcaattc aacaagaaga  14940
gctaactatc ctaaacatat atgcacccaa tacaggagca cccagattca taaagcaagt  15000
tcttagagac ccacaaagag accaagactc ccacacaata atagtgtgag actttaacac  15060
cccaatgtca atattaggtc aacgagacag aaaattaaca agcatattca ggatttgaac  15120
tcagctctgg acccagtgga actaatagac atctacagaa ctctccaccc catatcaaca  15180
gaatatacat tcttctcagc accacatcac acttattcta aaattgacca cataattgga  15240
agtaaaacac tcctcagcaa atgcaaaaga atggaaatca taacaaacag tctctcagac  15300
caaagtgcaa ttaaattaga actcaggatt aagaaactaa ctcaaaacca tacaactaca  15360
gtggaaactg aacaacctgc tcctgaatga ctactgagta aataacaaaa agaaggcaga  15420
aataaataca ttatttgaga ccaatgagaa taaagataca acataccaga atctctggga  15480
cacagctaaa acagtgttta ggggaaattc atagcaataa atgcccacag gagaaagcag  15540
gaaagagcta aaatcaacac tctaacatca caattaaagg aactagagaa gcaagagcaa  15600
acacattcaa aagctagcag aagacaagaa ataactaaga tcagagcaga actgaaggag  15660
attagagaca caaaaaaccc ttcaaaaaaa tcagtgaatc cagaagctgg ttttttgaaa  15720
agattaacaa aatagataga atgctagcca gattgataaa gaagaaaaga gagaagaatc  15780
aaatagacgc aataaaagat gataaagagg atatcaccac tgatcccaca aaaatacaat  15840
```

```
ctaccatcag agaacactat aaacacctct atgcaaataa actagaaaat ctagaagaaa  15900
tgaataaatt cctggacaca tacaccctcc taagactaaa ggaagaagtc aaattcctga  15960
atagaccaat aataagttct gaaatcgagg cagtaattaa cagcctacca accaaaaaaa  16020
gcccaggacc agacggattc acagctgaat tctaccagaa gtacaaagaa gagctggtac  16080
cattccttct gaaactattc caatcaatag aaaaggaggg aatcctccct aactcatttt  16140
atgagtccgg catcatcctg atacaaaaac ctggcagaga cacagcaaaa aaataaaatt  16200
gtaggccaat atccctgatg aacattgatg caaaaatctt caataaaaaa ctggtaaact  16260
gaatccagca gcacatcaaa aagcttatct accatgataa tttggcttca tccctgggat  16320
gcaaggctgg ttcaacatat gcaaatcaat aaagataatc catcacataa agagaaccaa  16380
tgacaaaaac cacatgatta tttcaataga tgcagaaaag gcctttcata aaattcaaca  16440
gcccttcatg ctaaaaactc tcaataaact aggtattgat ggaacatatc tcaaaataat  16500
aagagctatt tatgagaaac ccacagccaa tatcatactg aatgggcaaa agctggaagc  16560
attcatttga aaaccggcac aaaacaagga tgccctctgt caccactcct attcaacata  16620
gtattggacg ttctagccag ggcaatcagg caatagaaag aaataaagca tattcaaata  16680
ggaagagagg aagtcaaatt gtctctgttt gcagatgaca tgattgtata tttagaaaac  16740
cccatcatct cagcccaaaa tctccttaag ctgataagca acttcagcaa agtctcagga  16800
tacaaaatca atgtgcaaaa atcacgagca ttcctataca ccaataatga caaacagcca  16860
agtcatgagt gaactcccat tcacaattgc tacaaagaga ataaaatgcc taggaataca  16920
acttacaagg gatgtgaagg acctctttaa agagaactac aaaccactgc tcaatgaaat  16980
aagagaggac acaaacaaat ggaagaacat tccattctca tggataggaa gaatcaatat  17040
cgtgaaaatg gccatactgc ccaaagtaat ttatagatcc aatgctatcc ccatcaagct  17100
accattgact ttcttcatag aattagaaaa aactacttta aatttcatat ggaaccaaaa  17160
aacagcccgt atagccaaga caatcctaag caaaatgaac aagctggagg catcatgcta  17220
cctgacttca aactatacta caaggctaca gtaaccaaaa catcatggta ctggtacata  17280
aacagataga tagaccaatg gaacagaaca gaggcctcag aaataacgcc acacatctac  17340
aaccatctga tctttgacaa acatgacaaa aacaagcaat gcagaaagga ttccctattt  17400
aataaatggt gtcgggaaaa ctggctagcc atttgcagaa aactgaaact ggaccccttc  17460
cttacacgtt atacaaaaat taactcaaga tggattaaag acttaaacat aaaacataaa  17520
accataaaaa ccctagaaga aaacctaggc aataccattc aggacatagg catggcaaag  17580
acttcatgac taaaatacca aaagcaatgg caacaaaagc caaaattgac aaatgggatc  17640
taattaaact aaagagcttc tgcacagcaa aagaaactaa catcagagtg aacaggcaac  17700
cgacagaatg ggtgaaattt tttgcaacgt atccatctga caaaaggcta atatccagaa  17760
tctacaagga acctaaacaa gtttacaaga aaaaaaacaa ccccatcaaa aagtgggcga  17820
agggtatgaa cagatgcttc tcaaaagaag aaatttatgc tgccaacaaa catacgaaga  17880
aaagctcatc atcactggtc attagagaaa tgcaaatcaa aaccacagtg agataccatc  17940
ttatgccagt tagaatggcg atcattaaaa agtcaggaaa caacagatgc aggagaggat  18000
gtagagaaat aggaacactt ttacactgtt ggtgggagtg taaattagtt caaccattgt  18060
ggaagacagt gtggtgattc ctcaaggatc tagaaccaga aatatctttt gacccagcca  18120
tcccattact gggtatatac tcaaaggatt ataaatcatg ctactataaa gacacatgca  18180
catgtatgtt tattgtggca ctattcacaa tagcaaagac ttggaaccaa tccgaatgcc  18240
```

```
catcaatgat agactggata aagaaaatgt gacacacata caccatggaa tactatgcag  18300
ccataaaaaa ggatgagttc atgtcctttg cagggacatg gatgaagctg gaaaccatca  18360
ttcttggcaa ggtaacacag gaacagaaaa ccaaacacca catgttctca ctcataagtg  18420
ggagttgaac agtgagaaca catggacact gggaggagaa catcacacac tggggcctgt  18480
cagggtgtag gaggctaggg gagggatagc attaggagaa atacctaatg tagatgacaa  18540
gttgatgagt gcagcaaacc accatggcat ctgtatacct aggtaacaaa cctgcacgtt  18600
ctgcacatgt accccagaac ttaaaagtat tattattatt attataataa taataataaa  18660
agaaatacaa taaaatagaa tgcagcatac agcagtgatt ctcaaacaca ttcagcatca  18720
gaattaccct tgaatcttta aaatatatat acatatgaga tcttagtctc caagatttgt  18780
aagtttggta ttgggtccct gggcctatgt tgggtttaga aacttctaca gatggtttgg  18840
atgtatggga cagtttaaga atcgctgaac taaaatcaaa taaactgaat atcctgtgat  18900
ttagagagac ttatcgttta tttcactatc caagtacttg cattagagcg tggctagaag  18960
ggatttgcag ccttgtaaat aatcagaaat tcagacattt tgagatgaga gaactgctga  19020
agattttatt ctgacttgaa ataaattttc taattagaaa cttccaggtg agagcaaagg  19080
cctggaacaa tattcctgag ccagaggagg atcgagtttg actccaggcc taacacttac  19140
taggtctatg accttgggtc agtaatttaa attctctgta tctcaacctc tcaacagggt  19200
attggtaggg attaaatgtg ttagtgtctg tgaagtgctt agagcagtgc ttggcatagt  19260
aaatgcttaa tgaatttcag ccactgtttt tatttttagt actttccagc tcccccaaaa  19320
agatactttt tttagacttg tattaagaca ataaaaagtt taatcagcat gcttcatacc  19380
taaatatgct tcactttata gcaaagttta caagactaaa actgttttgt tgtaattctc  19440
tgagtctcat gtgtttatta atgatttttt ctgctgttta ttcatctgaa ttctactcat  19500
tcttcaagac ctagctggaa tcctgtttct agaaagactc ttgcccataa taataaacct  19560
gccctatctg agttcctagg tggtctgtac ctcataattt ggtaattaat tgtatatgca  19620
cttatataac aaaacattat tgtgtgtctt tgctgtatca gattctaggc tggaagttgt  19680
agatatgatg tttttgtcta gaaaaatgtt ctagaatgtc ctactcagga cagtctgttg  19740
actttaaaga cacatttcct aaacagacac ttcatgaggc agccccagcc tgtacctgtg  19800
ttcctggacc tgatgatcaa gtttgattta agcctcacca cttactagct ctgtgatttt  19860
gggcaagtta cttgaattct ctgtgtgtag atagaacaat gttgagggaa atccctttcc  19920
cccatccttg tgtttccaca agggaacttg cttcctaata agtaacactt tcaggggaat  19980
attctaggcc cttctcttat ccccattact tgttctttct gtgaaaagag gagaggttaa  20040
tctgatggat gaaatcctta atctttcatc ttctggactg tagagcctgt gaaccaaagc  20100
aatggaccac ttgcactgaa attgaggctg accctgtatt ttgattctta tttggcaact  20160
tatttctatt ctgttcccaa ttcaaaatcc caaggggaga aggaagataa ttgattacca  20220
gaagtatgta atggtggtag gaagttgaat aaatggtaac tttttaaaag ttgcatgaga  20280
tatagtcctt atcccagaga agctaagttt gcttttcttt cctctcatgt attttagtat  20340
tatttctaca attagattgt aaacccttta aaagcaagaa tatttctaca ttttcttact  20400
cctgatagca cacagtagac tgctgggcac atacatagta ggtggctctg taggtacttg  20460
ctaaatgatt caacatgttt ttccctcatg gaaaagaaag atttcagtat tgttcttatc  20520
agctaggaag gcactctgaa taggaaatca gttctaggca ggtatccata aatgggttat  20580
```

-continued

```
gatttccaac ttacttgccc cagaggctcg ctaatgttga actcttcatg ggtactttgt  20640
cttgcttcat gagctataca tgctaagggg ttagcagatc atataatctt ttgatctaca  20700
aaatatgatc tttattgaac aaaaacttgg gccaaaggcc tttctccttt gccaccttcc  20760
tccctctttt cattctcttt tttgggaatg ccctttgtgc atgttagtta cagcatgtac  20820
cacattgcac tgtattgttg gtttttgggt ctaacccacc cttaacactg cagtccccaa  20880
gggcagaaat tcagtctcat tcattttgat gtcctcagtg cctgtgctca gagaatatct  20940
attatttgaa aaaatagtgc aaaagtaaat tttaggagac tacatcacac tcatctaaac  21000
tgcaagtttg acaagttgac atccaaaaga aaggctctcc taaataacct cgccacagaa  21060
atttgggtga cctttgtagc tctggagaaa gcagaggcaa aaatgaaacc taaaaattat  21120
ttgtgggttt ttaaaaaatg ttttctcatg gagtaaaggt ctacagctga gttcttttca  21180
tatgagggaa tgacagaaac acagctggtt ctgactttca gcttcaactg agcgaccaga  21240
gctctgctgg tgaaacagga acttgtattg tgcccctgac gtgcaccttg aaggtgtcag  21300
ctcattgtcc ctttgttcac ataaatagtt ttttaagaat tgtttttgat cttgtgagcc  21360
tctaactaaa tgattaacca tgcaaagttg gccatttggg gtaatactga agcacttctc  21420
ttgagggcta ttgacaggtg ggaatgtgcc cacctccttg ggtctctggt tttcatgtca  21480
tacttgcaaa tcagtgacag tttaaacttg gggcaatcac ttagcaagtc tattgagtta  21540
ccaagttaat tattcccact ttgcatgaag caaccttgaa aatgattttc ctaaagcaaa  21600
gtacatccaa actcagtacc ttcttaataa cctttgctga atgaataaat gactaattca  21660
taaaaaatgt aacatatctt taattcttac ttacgggcag tttaagcctc ttgtgtaaga  21720
ggaggcctcg gcttgagata acataggata gtaagcctcc tagagaaatt tctatatgga  21780
aacatggtct gctatgaagc tagaagtgag aggacattat atttgaccat tatatttggc  21840
ttcagagctt ctcaacatgg ggcccaaagt caaggtccct tgtttcatta agaggaggtc  21900
caggagtgca tgacacccat cagactactg agacccagct ggaactaggc accttgcaca  21960
ggggccttgc ctaatcaaaa tagttcttat tttttctgag ttccaagtaa ctagtttcct  22020
aacccagtgt ctggatagta gtgccaagtg ggagtacctt caatgaactt cctcatgagg  22080
ttatttctag cctattggaa tgtttcgttt taggagggtg aggaagggaa gtcttgaatt  22140
tttgtgctta gtttaatgtt gtgatacagc tttgaccatc cgtttaatgg gagatctgtt  22200
ttccagatga ctatacatgt ggaaaggaga agtttttga gtgtttttt taacccccttt  22260
taaagaatgg tttttcattt agtctctaca tttgggggta aaaggtcctc tagggagact  22320
tttcaaaagt atttgaagtt tgcatctgat ttcagaggtg agttggaggc ctatctgtgt  22380
atgacagaca catgtctcca acaactatat gttcacaagg actaagagcc atccttttgg  22440
gtccatcatt caacattgat ctcacattcg tgttcgtatc agtatcttta cagtgcgctc  22500
ccagttacat ctccctaatt tcccttagta ggcttcacag aatttgcagt gtatgcaatg  22560
gcagatgacc acatgtggag tcatttaacc acatcttcca ctgcaagtca gcccgctctt  22620
gatgtctgtt tatgtttaga ttccatcttt tggaagattt cattcctctg cactatctca  22680
gtatctcaga tgcttttgag actgggtcct tttcccctcc tatgtttggc catggccacc  22740
ccctcagggt tgtgttgtgt ttcacagctg ctgtttgtag ggttgacctt tacaatgtac  22800
aaagctcttt cccatatgtt gacaatccct ggtgtgatgc tgtgagttag gcagggtgtg  22860
tatacgtgtc ctcatcatat tacagtggta aggcaacagg gtttttgaat ttgatcaccc  22920
atgaatttgt ctaatttgtt ggtaaaaaat ggtcatgtat cagccgtttc acagggtcag  22980
```

```
cttaatagaa agtgggagtt aggcaggacc agaattcagg acttcagccc ccggtcccag  23040
ggactattct ctatacccaa ttgtcccacc ttgaatcagt ttcttctagg gaaatatctc  23100
caaaactgag atggcaccca caggacttct taattgtagt cattaccagg aaaaacaagc  23160
aaaggaactg gtgtaaatct ctgtttttgg tgattggtgg agatttggag attgtcttgt  23220
gtcaaaagta aagccactag attaaatgtt ttgttaataa attggttatt tttaatttaa  23280
ttatttgaca gttaatttac attattcaaa aatcaaaata aaatttaaaa gaagtttaca  23340
ctgaaaagtc ttgccccact tataccctgc tcacctcagt atcccccaat acataccatc  23400
tataaggtga tcatttgtat tagtttcttg tgaatccttg atagtgtgtt ttatatagat  23460
acaggtaaat atgagtatgt actattattt cccccccacc ccaccctgtt tttttttga  23520
gacggagtct cgctctgtcg cccaggctgg agtgcagtgg cacgatctcg gctcaccgca  23580
agctccacca ttttccccca tttttaaaac aaaaggtagt agccatatat acactatttt  23640
acaccttgtt ttatcactta ctaatatata ccagagagct ttccatcatt ttgtacatat  23700
gcacctatat ctgtcaatta ttcccagaag tggaattgct gggtcagcag gaaaaatcat  23760
gtataatttt gataggtatt gcctaattgt cctgcacagg gcttgaattg tttgtactcc  23820
cacctttagt gtatgagaag acctgtttct ccatagcctc atcaaacaga gtgtgtgaga  23880
ttagatgaga aataggaggt gagcagtctt ttaccccatc cgtagtttgc agtgggaaca  23940
ctgcacagtt gcaagagctg gtgcaggtat cagattagtt ccagtggaaa cgctgcctca  24000
ccatggccat gggcttgcgc cagctctagt gacacacacg gaatggaccc acgttgccac  24060
ttgcagaatt tcctgtagca gaaagttgaa catgcattca ttattcatct aactagccat  24120
gctggatcta aagagcacaa cagtgttttt tagaaccaaa aagaaaattg tttcactaca  24180
acacactgtg tataaggctt tcaatgctct tttctcagct attaacatta ttttcaggac  24240
tgagttcaag agatgtatcc caaatcacag ggatgtcttg ctaagcttgg aactttcata  24300
ctcaagggat gctttttga ggaatgattt tacacttact caacatttgt aattaaataa  24360
ttagtacttt ataagataaa tttaaactgt ccaagtacaa tataaacatt gaactatgat  24420
gcattattgc tagacttttt ccttaaagtt gccaagtggt ttcctgcatt aggcaaatag  24480
gggatcatat aaaaatgcca tgatttacgg cctagataac atctccacca tttgagcagc  24540
atatattcca ggtcatcccc acataactcc ttaccattct cattagaaag gttgattctt  24600
agtcttattt ttctctgagg acagcaaaaa aaaaaatccc cttcagttcc actgcataga  24660
aaagtgtggt aaatggagcc gggcacagtg gttatttaat ttaaatggac aatatttttt  24720
atagaatttt gacagggcca ctgtataggg gaaagtcact cctcttcccc tttatagaag  24780
agttgcacct ggacagttgc attgatgact gtatccagtc tacacaagag gtcattcctg  24840
ggcataagaa tggactgcca aaatctagct gaaacaccat tgacaaatag acattttctt  24900
ttgttaataa tacctgtgaa ggctttcata acagacattt ccagttttgt tctcaggctc  24960
cttgcagctg ctcctctaaa agtgtgctct cttccaagag ctgacaatgg ccagaagcaa  25020
ggtgttctgt cttttgtgcc atcatcatct aacttgccac acacatttgg gatgtcagcc  25080
taggtatagg ttttgtatcc actcagtatg gcttgtgggt ctggttgcct ttgttattca  25140
tgctgagggc ctctgggcat cagtttggtg tgagagaacc cattccatga ccctccttcc  25200
tttggctgtt ttgactcgat ggctcttgtt ggcacagtct gtgagtgtct gatgctctat  25260
ccatgccgga ccatctgttc tgctgtctct gtggtctgaa gtcgttttct gaactattcc  25320
```

-continued

```
ttgataataa atttgagatg atcttgttct acctttcttt tcaagtcaca tcttagcccc  25380
ttagccacat tcccgaagaa catgacaaat ggatgggtca caagtcacgt agcatagggt  25440
gtcagaccac gaggctttga agggattctg ttgggtgcta aaaagaaaga ttttgtgtca  25500
ccacgatttt ttttaaaggc atgttgacac ttaggcctta attgaaagcg ttcttactca  25560
agtagagttg acagaggagt atttggtagt cgcggttgct ggtctgaaga gcatgtggtt  25620
ctgtttcaat gcccaatgag atcttctcac gggaaaatgt tctgacatct caaacaaatg  25680
accttcatgc atagttttga caaaataccc tattaagtat gcatatatgg ttggtacctt  25740
gtggtaataa ttcaatactg gaaacagagt agcaacaaag aaacattagg gttatattta  25800
acctctgtgg aattagtgtg taaacaaact gcttatcaga aatgctcata tggggctttg  25860
tttaaataaa taagaaactg gcatataggg tctgcaggat atttctgcca agtagacctc  25920
cctcacatta taagacacca catctatgtc tgaccccata tggaaagagg catagcaagc  25980
cagcactggt tcatattccc tctccaccac ataatgggta tgtgatctta gggaatccac  26040
cgaaactctc tgggcctcag tttcctcagc tataaatggt ggataatcaa attatttacc  26100
tcaccattaa taaatgttag ctattatttt ttatcaagtt taatacaaag agaaacattt  26160
tacttatttt tccagctatc cagagcatct tccaaaatcc tatcaccaac aaatactgta  26220
ttgtatttat tatagcaact atgtaaaaat ggagtccctg tcctatgctt agatgaaata  26280
tgttggtatt tgagtttgca tgtcttctat aggaatcagt gtttagtgaa aacgggtgga  26340
gataaacaga tgttttcaca gtcctgttgt tcacagtacc gccaaattga atgtttccat  26400
ataggtgcat tctaatggct taaatgatgc agatattttc tggccagcca tatggatctt  26460
ttgtcatcta agatgttaat attttcctta tattttatag tagttctgga gtacagccag  26520
tttcttgaat agggtccaca tggctcatta tgcacagggc ctggaaactg ccttactcgt  26580
gctgttgaaa tgaaccgtga cacttcagaa gagctgggag ctggggtaga gcagtggcta  26640
ggagaacata ttcaattata tttcctcctg cattaagcta caagtaatga gcactttcct  26700
gtgctttaca gttaagtaat taaaagaaat tatagagtgg gatgcaaaaa taacccgaag  26760
gacaactgga tgtgtggagc caccagtttt ctccatgagt gcacaaggtt aatccttgtt  26820
actactcaga atgctgagtt tctacagaaa gggttgcagg tccacacatg ttttggcgtc  26880
tacccacacg cttctgtatg gcatgactgt gcatcccaga agaagggctg tgctgtgtac  26940
ctccacgttt cagtggaatt taacaaactg atccctgaaa atggtttcat aaaggtgagt  27000
aacagagagc taatagcctt ctcttgctaa ttttatcttt cccccaagat ttcttgataa  27060
tagtttgaaa aggagtgtta ttctttggtc tctagaggca acttaccttt ccagtttctt  27120
ccatcacctg ttttcatctc tcttgttttt ttaaatttaa tgctgtatgt atttcagagg  27180
ataggatcta atctagtgcg gtcccttcat caggtgagaa ttattcatct cattttcatt  27240
ttagcccttc tgaattaatg acattgaagc ccggcagttt ggtcctaaga tgggtttaat  27300
tatgtacaga tactctttct ataatggaaa ttgctcagat aactaattaa ccacaagaat  27360
acactgtcta tggaaaattt caggagcacc gtctgtggaa aaactgggaa gggcatgctg  27420
tcaccacagc tctggggtct attaaaagtg tggttatgca gcactggtgt ctagtggggt  27480
gttggctctc aactgccaga attcccatag catttcatgg cagaaagtca aggtgtccag  27540
caatactctg aaagtgacct gttgattaaa gtcgtcaatt ctgaagaaag agactgaaat  27600
aagacaaatg ggtcttaact ttttttctct ttctctctct tgtaaaaatg tgtgattgtt  27660
ctggcatgtt cccaatcccc acataatgcc aacatctttt cttaaagggg gattcccttt  27720
```

```
atccttggat ctgagaatta ttgcatgttc tccctttagg gacaatgaat gcagttgcat  27780
caccttgct tttttttttt tttttgtaca cagcatgctt attcttggat gcagggactt  27840
gaaagacaaa gccccacctg gctttcacaa catctcctat tagtaggtgt gccttgtgtg  27900
taatttgaag gaggcggtcc cttagctgtg tttacactgt acttttaaat gtggggctga  27960
aggtagaatc aaccatactt aagatgccac ctgggaaaat agggttctgt gtcatctcag  28020
ccccacccat ttgcaaatga cttaacagca gcactattag ggttcctagt gtgagtcatt  28080
tgcatttgga ctggtgaact tggtgacttc ttggtgtttg gaaacaaaca acctttgcag  28140
tctttcgtaa aaagcctgaa cagtggacca gtctccagtt ctacttgcaa agctgccccc  28200
atcaaatccc tcataatgtt caacttaaaa aatgttacac ttttctctgg aaatctaacc  28260
ttttttcctt ttttaaaagc cattttaagt acttcagtct tgaatcaaat gatcccaaat  28320
attggacacc aacctagaaa ttgggttacc tcctgggaac tttatcgaag aagagagatt  28380
ttggttggag agggggtttt gatgtttgat acttatattt actattttaa tatttcattg  28440
ttgttgttgc tgctgctgct gtattatttt gcgagtttcg tttgtttaaa tttcatggta  28500
tttggtagga gagagctgga tctgttggtt tcaggacaag tctagaaata agaaatctgc  28560
cttgagtgag tgagttggtt ccctctgttg ctatttcacc attaaggacg aaaggaactc  28620
acaaggacca gagacatctg gctgaaagca atactagtgt gactggacat ctactacctg  28680
ccatagttgg tcatatcgtt tccagtatga ttctgattga gtgagtgata ttaggctatg  28740
ttcagggatc agggaggcta attatgctta tattgccttg tagcattttg gtaagaatta  28800
atgattgtgt agatgtccag atttaggtca gcaatattct aaaagttctc attgaactaa  28860
tcatgtttat aagtagcctg tactttctat cataataaca atagtggaaa agctagttga  28920
cataaaagga gcccagattt tacttaagta aaaacacaaa agcaaagata ttttcccaca  28980
taaattacaa aagcaaagat attttcccac ataaatgtcc ccataaaaca agttgaacca  29040
aagaggaaag atgacaggta accgtatgac acgctaagaa agtatcataa tacttaagtt  29100
aacttcaacc ttttatttcc ttatcctaag cagcctcttt tctctttatc atttagtcct  29160
gtgcttctca actttgataa gtaaaaaagt tattgcacta aataaatctt attgaaatgc  29220
aggatctgat tgagtgggtg gggtaggtgg aatgagggtg gggaagttga gattctgcat  29280
ttcttagaag tttctacttt atgttaaaat ggctaatcca tctcaacatt gagaagtaag  29340
gtttcactta atttcagcct gtgtaagttt atcccatatg tacatttcct aaaactctaa  29400
tctcaggccc caggaatttc tcctttagtt aaaatatttt taggaataaa tttgaattgc  29460
attaatacac aatttataaa tttaacacaa aaaattattt gaagtttgag actttaggtt  29520
gcatgaaatc aatttcatac ttgaaaattt tctataaatt caaaagtctg tgtatttaaa  29580
tacaatttaa atacctgtgt tacagtgaca tttgtttttc tgtctctctc tccaccattt  29640
ccagagtcat catccctgta cagaaaaatt tttcccacat gatttcacca taaattcatt  29700
aaatatgatg cttacttgat aatttctcca ggttcttttt ttttttaatt atactttaag  29760
ttctagggta catgtgcaca acctgcaggt ttgttacata tgtatacatg tgccatgttg  29820
gtgtgctgca cccattaact cgtcatttac attaggtata tctcctaatg ctatccctcc  29880
cccctacccc tactccatga caggtcccag tgtgtgatgt tccccaccct gtgtccaagt  29940
gttctcattg ttcagttccc acctatgagt gagaacatgc ggtgtttggt tttctgtcct  30000
tgcgatagtt tgctcagaat gatgtccttg ctcactgatg gacatttggt tggctccaag  30060
```

```
tatttgctat tgtaaatagt gccgcaataa acatacgtgt gcatgtgtct ttatagtagc  30120
atgatttata atcctctggg tatataccca gtaatgggat ggctggctca aatggtattt  30180
ctagttctag atcctagagg aatcgccaca ctgtcttcca caatgtttga actagtttac  30240
agtcccatca acagtgtaaa agtgttccta tttctctaca tcctttccag cacctgttgt  30300
ttccggactt taatgatcgc cattctaact ggtgtgagat ggtatctcat tgtggttttg  30360
atttgcattt ctctgatggc cagtgatgat gagcattttt tcatgtgtct tttggctaca  30420
taaatgtctt cttttgagaa gtgtctgttc atatccttca cccacttttt gatggggtca  30480
tttgattttt tcttgtaaat ttgtttaagt tcttttagat tctggatatt agccctttgt  30540
cagatgggta gattgtaaaa attttctccc attccgtagg tttcctattc actctgatgg  30600
tagtttcttt tgctgtgcag aagctcttta gtttaattag atcccatttg tcaattttgg  30660
cttttgttgc cattgctttt ggtgttttag tcatgaagtc cttgtccatg cctatgtcct  30720
gaatggtatt gcctaggttt tcttctaggg tttttatggt tttaggtcta acgtgtaagt  30780
ctttaattca tcttgaatta atttttgtat aaggtgtaaa gaagggatcc agtttcagct  30840
ttctacatat ggctagccag ttttcccagc accatttatt aaatagagaa tcctttcccc  30900
atttcttgtt tttgtcaggt ttgtcaaaga tcagatggtt gtagatgtgt ggtattgttt  30960
ctgagggctc tgttctgttc cattggtcta tatctctgtt ttggtaccag taccatgctg  31020
ttttggttac tgtagccttg taatatagtt tgaagtcagg tagcgtgatg cctccagctt  31080
tgttcttttg gtttaggatt gtcttggcga tgcgggctct tttttggttc catatgaact  31140
ttaaagtagt ttttttccaa ttctgtggag aaagtcattg gtagcttgat ggggatggca  31200
ttgaatctat aaattacctt gggtagtatg gccattttca tgatattgat tcttcctacc  31260
catgagaatg gaatgttctt ccatttgttt gcgtcctctt ttatttcctt gagcagtggt  31320
ttgtagttct ccttgaagag gtcttccaca tcccttgtaa gttggattcc taagtatttt  31380
attctctttg aaacaattgt gaatgggagt tcactcatga tttggctctc tgtttgtctg  31440
ttattggtgt ataggaatgc ttgtgatttt tgcacattga ttttgtatcc tgagactttg  31500
ctgaagttgc ttatcagctt aaggagattt tgggctgaga tgatggggtt ttctaaatat  31560
acaatcatgt catctgcaaa cagagacaat ttgacttcct ctcttcctat ttgaatatcc  31620
tttatttctt tctattgcct gattgccctg gctagaacgt ccaatactat gttgaatagg  31680
agtggtgaca gaggacatcc ttgttttgtg ccagttttca aagggaatgc ttccagcttt  31740
tgcccattca gtatgacatt ggctgtgggt ttgtcgtgaa tagctcttat tattttgaga  31800
tatgtcccat caatacctag tttatttaga gtttttagca caaaggctgt tgaattttgt  31860
caaaggcctt ttctgcatct attgagataa tcatggtttt tgtctttgat tctgtttata  31920
tgatggatta tatttattga tttgcatatg ttgaaccagc cttgcatccc agggatgaag  31980
ccaacttgat catggtggat aagctttttg atgttctgct ggattcggtt tgccagtatt  32040
ttactgagga tttttccatc gatcttcatc agggatattg gcctgaaatt ctcttttttt  32100
gttgtgtctc tgtcaggctg tggtatcagg atgatgctgg cctcataaaa tgagttaggg  32160
aggattccct ctttttctat tgattagaat agtttcagaa tggtaccagc tcctccttat  32220
acctctggta gaattcagct gtgaatccat ctggtcctga tggatttttt tggttggtag  32280
gctattaatt attgcctcaa tttcagagcc tgttattggt ctattaagag attcaacttc  32340
ttcctggttt agtcctggga gggtgtgtgt gtccaggaat ttataaattt cttttaggtt  32400
ttctagttta tttgcataga agtgtttata gtgttctctg atggtagttt gtatttctgt  32460
```

```
gggattggtg gtgatatccc ctttatcacc ttttattgca tctatttgat tcttttctct  32520
tttcttcttt attagtcttg ctagtgatct atcaattttg ttgatctttt taaaaaacca  32580
gctcctgggt tcattgattt tttgaaggag tttttctgtc tctatctcct tcagttctac  32640
tctgatctta gttatttctt gtcttctgct agcttttgaa tgtgtttgct cttgcttctc  32700
taaattgtga tgttagggtg tcaattttag atctttcctg ctttctcttg tgggcattta  32760
gtgctataaa tttccctcta cacactgctt taaatgtgtc ccagagattc tggtatgttg  32820
tgtctttgtt ctcattggtt tcaaagaaca tctttatttc tgccttcact tcgttaagta  32880
cccagtagtc actcaggagc aggttgctca gtttccatgt agttgagtgg ttctgagtga  32940
gtttcttaat cctgagttct agtttgaaag cactgtagtc tgagaggcag tttgttataa  33000
tttctgttct tttacatttg ctgaggagtg ctttacttcc aactatgtag tcaatttttg  33060
gaataagtgt gatgtggtgc cgagaagaat gtatattctg ttgatttgga gtggagagtt  33120
ctgtagatgt ctattaggtc cgcttggtgc agagctgagt tcaatttctg gatatctttg  33180
ttaatttctt gtcttgttga tctgtctaat attgaccgtg gggtgataaa gtctcccatt  33240
attattgtgt gggagtctaa gtctctttgt aggtctctaa ggacttgctt tgtgaatctg  33300
gtgctcctgt attaggtgca tatattttta ggatagttag ctcttcttgt tgaattgatc  33360
cctttatcat tatgtaatgg ccttctttgt ctcttttgat ctttgttggt ttaaagtctg  33420
ttttatcaga gactaggatt gcaactcctg cttttttttg ctttccattt ccttggtaga  33480
tcttcctcca tccctttatt ttgagcctat gtgcgtctct gcacatgaga tgggtctgct  33540
gaatacagca cactgatggg tcttgactct ttatccaatt tgccagtcca tgtcttttaa  33600
ctggagcatt tagcccattt acatttaagg ttaatattgt tatgtgtgaa tttgatcctg  33660
tcattatgat gttagctggt tattttgctc gttagttgat gcagtttctt cctagcctca  33720
atgatcttta caatttggca tgtttttgca gtggctggta ctggttgttc ctttccatgt  33780
ttagtgcttc cttcaggagc tcttgtaagg caggcctggt ggtgacaaaa tctctcagca  33840
tttgcttgtc tgtaaaggat tttatttctc cttcacttat gaagcttagt ttggctggat  33900
atgaaattct gggttgaaaa ttcttttctt taagaatgtt gaatattggc ccccactctc  33960
ttctggcttg tagagtttct gccgaaagat gctgttagtc tgatggactt ccctttgtgg  34020
gtaacctgcc ctttctctct cgctgcactt aatgtttttt ccttcatttc aactttggtg  34080
aatctgacaa ttatgtgtct ttgagttact cttcttgagg agtatctttg cggcattctc  34140
tgtatttcct gaatttgaat gctggcctgc ctcactagat tggggaagtt ctcctggata  34200
atatcctgca gagcgttttc caacttggtt ccattctccc catcactttc aggtacacca  34260
atcagatgta gatttggtct tttcacatag tcccatattt cttggaggct ttgttcattt  34320
ctttttactc ttttttctct aaacttctct tcttgcttca tttcattcat ttgatcttca  34380
atccctttct tccacttgat tgaatcagct actgaagctt gtgcatgtgt cacatagttc  34440
tcgtgccatg gttttcagct ccatcaggtc atttaaggtc ttctctatgc tgtttttttct  34500
agttagccat tcgtctaatg ttttttcaag gtttttagct tctttgctaa aaggttcaaa  34560
catcctcctt tagctcggag gagtttgtta ttactgatca tctgaagcct tcttctctca  34620
acttgtgaaa gtcattctct gtccagcttt gttccattgc tggcgaggag ctgcattcct  34680
ttggaggaga agacgtgctc tgatttttag aattttcagc ttctctgctc tggtttctcc  34740
ccatcttatt ggttttatct acctttggtc tttgatgatg gtgacgtaca gatggggttt  34800
```

tggtgtggat gttctttctc tttgttagtt ttccttctaa cagtcaggac cctcagctgc 34860
aggtctgttg gagtttgctg gaggtccact ccagaccctg tttgcttggg tatcaccagc 34920
agaggctgca gaacagcaaa tattgcagaa cggcaaatgt tgctccctga ttgttcctct 34980
ggaagcttcg tctcagaggg gcacctggcc gtatgaggtg tcagtcggcc cctactggga 35040
ggtgcctccc agttaggcta ctcaggggtc aggaacccac ttgaagaggc agactgtcca 35100
ttctcagata tcatattcca tgctgggagg acccctactc ttttcaaagc tgtcagacag 35160
ggacatttaa gtctgcagaa gtttctgctg tcttttgttc agctgtgccc tgcccctaga 35220
ggtggagtct acagaggcag gcaggcctcc ttgagctgcg gtgggctcca cccatttcga 35280
gcttcctggc tgctttgttt acctactcaa gtctcagcaa tggtggacac ccctccccca 35340
gcctcgctgc tgctttgcag ttcgatctca gactgctgtg ctagcagtga gccaggctcc 35400
gtgggcatgg gaccctccga gccaggcctg ggacataatc tcctggtgtg ccgtttgcta 35460
agaccattgg aaaagcacag tattagggtg gggagtgtcc tgattttcca ggtaccgtca 35520
gtcatggctt cccttggcta ggaaagggaa ttccccaacc ccttgtgctt cctgggtgag 35580
gtgatgcccc accctgcttt ggctcatgct ccgtgggttg tacccactgt ctgacaagcc 35640
ccagtgagat gaacccggta cctcagttgg aaatgcagaa atcacccgtc ttctgcatca 35700
ctcacgctgg gggctgtaga ctggagctgt tcatatttgg ccatcttgga acctcccttt 35760
ccaagttctt tattacagag tgggtcactg aaacttcatg gaacaaattg gaaattatct 35820
tcttaattaa tgtcactgtc taccatgtat gggaatttgg taaatattat atggtttcaa 35880
taacatagta gatagaacat tgtcaaatct aaacttcagt gaattgtaac agatcccacc 35940
tgaaattcta aagaaaacag aattctaatt gaagaggtta aacttttaca gggaatgtca 36000
actgccattt gggtcctgta aacaaaaaac tgttttttaa aaaagtaaac tttaaaagta 36060
ttttcagatg acctcatttg ctatccaagt ggcttgagta tgcttgatgc taagacttct 36120
ttgttacaga ctggagatgt gtgctactgg ggcagtgttg ctctgtgaca aggaggcaga 36180
ggatgagggc aaggttcgat gtgactgtga attctgggtg gctctggcta tcgggagcct 36240
tcattgatta cagcaaaaca gttgctttcc tagggcaata gtgtctctgt cacccaggct 36300
ggagttcagt ggcatgatca atcgctcact gtagcctcaa cttcttagac tcaagtaatc 36360
ctcccacctc agcctcccaa gtagctgaaa ctacaggtgt gcaccaccac acctaatttt 36420
tttaattttt aagtttttgt agagacatgg tctcactgtg ttgcccaggt tgatctcgaa 36480
ttcctgggct ctagtgatcc tcccgcctcg gcctcccaaa gtgttgggat tacaaatgtg 36540
agccactgca cctggccctt tgcaaccttc ttgacaatgc attcctttat tccctaactg 36600
gaagtaactt ctttctcttt ataaaattgt atctgtacct tttctgggtc atttctacct 36660
ttatattcta gttacgtatg tcctacctcc ctcctaggga gggaggtaag taagactgga 36720
aagtagactt catgtgtgat gaatgaatga acaaaaggaa gtctaacata tggatatagt 36780
caactggatg caaattaaaa atttttaaat attgatttgc aagatttcat taaggtcaac 36840
tcttaatagt ttgtatcata tatgttagga accaaatatt aataacttct tcagcattac 36900
cattatcttt ataggactgt ctaaaatgag cagccatatc tttaaactgt gttttctctg 36960
attacacgct cacaggtaaa acccaaaggg gctgggaaca aacaagactt tttttttttt 37020
ctgtatgcct gaattatctg tactgttgct tgttttccca cctttggcca tagaaactta 37080
gttctaacat gctacaattt ttgcagttct ttctcttaga aaaagaccac attgtctgaa 37140
atttcatcca tttaagtaat caagccttaa agttgaagga tcttggtcat gattaatcta 37200

```
gacctacaaa gtagtatctt aatggcactc cttttagaaa gttaggttcc aggacacaca  37260
tagctgcagt gtccacattt tgtaagctcc ttcgttgtca cagccactct cttctctgtg  37320
gctgatattc taaaactggc aacacatcct gatggtaaaa gcttggttca ggagacaggt  37380
gacctactag ctttatggca tttgacaggt tacctaacct ctctgacgca taattgcctc  37440
atctatataa tggggataat aatacccatc ctgtctcctt gtaaaaatca aattagatga  37500
cgcctgtgaa tgttctatag tctcttagac aaatgtaagt tatgactaca gcaagagtaa  37560
aagagcatgt tgttatggac attctttcag tgaaatgtct aagacttgtg agtcacactt  37620
aaagctaaac ttgatatcta cttcattgat tttcttttta gttctatgta ctatattgaa  37680
tttcctgaca gtggggctat gaaagccttc ctagcatttt atagatgtgg ttgaattaat  37740
ggctgtaagc cttaaagcag aattagacag catcaatgaa tttattaagt ataaataaat  37800
atataatctg cttagcaata ttacacagcc tctttatctt atgtgtgata aagagtcatc  37860
cgaaggttga aaatgaagaa ttgtcctgga agctcttact taatctttta ttatttccta  37920
atacagtata taaaattact cattgaaagc ttagcagaat aagaaacaag aagttaaaag  37980
gctgaaaact acaaattttg ctattattat tgttattact tcccaagtct cttattgatc  38040
tgttagaaat agagctacac aggaaattgt aggacagtta gtatgtggta gtgttatctg  38100
ctttttaatt attcaagtaa ggttttattc cattagagga actcaagaag ttggtcatgg  38160
ctgataattg ctatctgtca aattccttag agcagggatc cgcaacaccc aggccatgga  38220
ttgttaccag tccctggcct gttaggaacc aggctgcaca gtaggaagtg agcggcgggt  38280
gagcaaacat tgccatctga gctctgtctc ctttcagatc agcagcagca ttagattctc  38340
atagaagcat gagccctgtt gtgaactgca catgcaaggg atctaggttg tgtgctcctt  38400
atgagaatcc aattccttat gataatttaa ctgatgatct aaggtggaac catttcatcc  38460
caaaaccatc caccctgcta ctcccagacc gtggaaaaat tgtcttccac aaaactggtt  38520
cctgctgcca aaaaggttgg gaccactgcc ttagagttta taatttgggg ttagcacagc  38580
ctatatttac ctgagaattt caatgggttc actgatcttt ccaaatgaaa aggcttctta  38640
cgaaaattat atccaaactg tcttttctct tagtttaata aacctatcag taagttttta  38700
ctgagtactg ctattacatt tttctctgtt aagcattatg gggctcaga catgatccat  38760
tccctcaaag aacttacctt tcagctgaag actgactaga atgagcaaat acggttaaca  38820
attaacaagt gagtaggcca gctcggccaa catggtgaaa ccctgtctct actaaaaata  38880
caaaaattag ccgggcatgg tggtgggcgc ctgtaatccc agctacctcc tgctgaggca  38940
ggagaattgc ttgaacccag gaggtggaga ttgcagtgag ccgagattgc accattgcac  39000
tccagcctgg gcgacagagc aagactctgt cttgggaaaa aaacaaaaca aaacaagtga  39060
gaagggaatc aagtactacg taagatgtaa tgtggaattt tagggaagga aggcagtgta  39120
tgctggagta attagagaaa ggggcatgca tgatttgatg cttgaactgg atcatgaagg  39180
ataagcaaga ttttggcagc aagtgagagg gagagaggag tttgtcagag gaatggaaca  39240
agtcaggagg cagtaatgtg tacggcactc caaggactct gtcctgatcg gagcagaagt  39300
gatgaagcat tgagtagttt gagaaagtta gctaagaagg gtgagggcag atgttggaga  39360
gagttgagta tcagagagaa gacattagat ttgagcagat agaacaaaaa tgccattgcc  39420
agtttttgtg taagagaata gtattagggt ggttacccag gaagtggtca tcagagttga  39480
atggagcaga aagagtgtct gatacagcat cgggacgttg tggtcacaaa atgaggtggt  39540
```

```
gagggctgag ccaagatggt ggcagtggga tggataaaaa gggatggcca ggacaaatat  39600
tttaaaggaa aaattaacag gacatcttta ctgactggat tggaaggcta tgcaggaaat  39660
atattgtcaa acttgattcc aggatttcta tcctatgcct gggttgccca aaatatcagg  39720
gaaccattgt tagaaaaggt aggagatacc actgttccaa caaaaagtat tgagtttggt  39780
gttgcaccca cttaacttca aggccttaca agtgagtaga cagttagtta gaattgcaga  39840
agtgccactc agagagcagg gcttgcaatg tggggttgga ctttgtcacc attgtgttaa  39900
ttcctaattc tatgcagatg ctcagcttga ggaataccca tgtttgggct tcagaatgaa  39960
agccaagtaa tatttactca gatgccaatt ttccctctga aatatttgct catggaactg  40020
agagaacaat atataaagca ttaattattt ttctcataaa gttattaata aaaagataag  40080
atcagtgaaa ggcagagtaa actagaagcc aagtatagaa aatggtatca ttcaaagact  40140
cattactgta gtggtgaaaa caaaacaatt ttccaacagc ttaagatgcc tcagtatttt  40200
ggaccatttt taagtagtta gtgtgggcac ttagtaaata tgtattaaac tatagttcat  40260
taattctttt tttttttttt ttgagatgga gtttcactct ggtcacccag gctgcatttt  40320
tgctttctta gtgatatata aaatgtcgag tttcacaatg atggtatctt agatttgatt  40380
aaatatggta ttaaaaaata gctgatcaca gaaagtctct accagtgtga tgtagatggc  40440
taaagtattc cacatttgca aacttttatt gacctaaata agaggtgccc cttgggttgt  40500
ttttatttgg actgggaata ttaggagaaa gctttttcat tcagtgtgta agtacaatct  40560
accagaaata gaaacccca tggacgatct atttctttga tggtacagga ctcagaacat  40620
tcacaaagat ttagttgtta gcggaataga catctgtatt ttattcaaac caattttccc  40680
ttcctaatct gagaacattg tgcaatctaa gcagttctaa gcatgtttgc tattcgtgca  40740
aagtgagagt aaatctaaaa gaaatttttt tgtgtgttta gggatggtaa taaagtctct  40800
tagtggttga aaatgttatt tcttacaaaa gtggagaaca tttgcttttc aataccagag  40860
ttttcagcca tttctgcatt ctgacctatt gactggaggt aggttgcctt tgaattcagt  40920
aaaacttcat gggcagaaac acagttcctt ttcctactta tttggatatc atgatggcca  40980
ttgcatgtat gtgtcttttt gtaagtccat gcctcagaac tgagaagtag gaataaaatt  41040
agggtcaggg ctggggatgc tactctttgc tgctgagaaa cacaatgctt caggtaagtg  41100
attctgaagt ccttcaccac ctgacggtaa ccttgggttg gtccataggt atgttttcat  41160
tttgcttgtt catccatttt aattggcttc ctagagcatg cttgtagatg tagagccaaa  41220
tttagagtag agcaaccctc tggcaaacag gaagagatta attttgtggt atgcttttaa  41280
gggacttccc aggaaacttc aaaagcagaa aaagaagcac tagctgccta ttccaaaatg  41340
tgtaaaacac cactcagctt tttaaaagta ggataaactc agagcgcgcg cacacgcgcg  41400
cgcgcacaca cacacacaca cacagagaga acatctctag taaaaagaaa agttgagctt  41460
tcttagctag atgtgtgtat tagccagaaa aagccaagga gtgaagggtt ttagagaact  41520
ggaggagata aagtggagtc tgcatatggg aggcatttga aatggactta aatgtctttt  41580
taatgctgac tttttcagtt ttctccttac cagacacatt gttttcatga cattagcccc  41640
aggcatagac acatcattaa aatgaacatg tcaaaaaatg atttctgttt agaaataagc  41700
aaaacatttt cagttgtgac cacccaggtg tagaataaag aacagtggaa ttgggagccc  41760
tgagttctaa cataaacttt cttcatgaca taaggcaagt cttctatggc ctttggtttc  41820
cttacctgta aaacaggatg gctcaatgaa attatctttc ttctttgcta taatagagta  41880
tctctgtggg aagaggaaaa aaaaagtcaa tttaaaggct ccttatagtt ccccaactgc  41940
```

```
tgttttattg tgctattcat gcctagacat cacatagcta gaaaggccca tcagacccct  42000
caggccactg ctgttcctgt cacacattcc tgcaaaggac catgttgcta acttgaaaaa  42060
aattactatt aattacactt gcagttgttg cttagtaaca tttatgattt tgtgtttctc  42120
gtgacagcat gagcagagat cattaaaaat taaacttaca aagctgctaa agtgggaaga  42180
aggagaactt gaagccacaa tttttgcact tgcttagaag ccatctaatc tcaggtttat  42240
atgctagatc ttgggggaaa cactgcatgt ctctggttta tattaaacca catacagcac  42300
actactgaca ctgatttgtg tctggtgcag ctggagttta tcaccaagac ataaaaaaac  42360
cttgaccctg cagaatggcc tggaattaca atcagatggg ccacatggca tcccggtgaa  42420
agaaagccct aaccagtttt ctgtcttgtt tctgctttct ccctacagtt ccaccaggtg  42480
agaagagtga tgaccatcct tttccttact atggttattt catactttgg ttgcatgaag  42540
gctgccccca tgaaagaagc aaacatccga ggacaaggtg gcttggccta cccaggtgtg  42600
cggacccatg ggactctgga gagcgtgaat gggcccaagg caggttcaag aggcttgaca  42660
tcattggctg acactttcga acacgtgata gaagagctgt tggatgagga ccagaaagtt  42720
cggcccaatg aagaaaacaa taaggacgca gacttgtaca cgtccagggt gatgctcagt  42780
agtcaagtgc ctttggagcc tcctcttctc tttctgctgg aggaatacaa aaattaccta  42840
gatgctgcaa acatgtccat gagggtccgg cgccactctg accctgcccg ccgaggggag  42900
ctgagcgtgt gtgacagtat tagtgagtgg gtaacggcag cagacaaaaa gactgcagtg  42960
gacatgtcgg gcgggacggt cacagtcctt gaaaaggtcc ctgtatcaaa aggccaactg  43020
aagcaatact tctacgagac caagtgcaat cccatgggtt acacaaaaga aggctgcagg  43080
ggcatagaca aaaggcattg gaactcccag tgccgaacta cccagtcgta cgtgcgggcc  43140
cttaccatgg atagcaaaaa gagaattggc tggcgattca taaggataga cacttcttgt  43200
gtatgtacat tgaccattaa aaggggaaga tagtggattt atgttgtata gattagatta  43260
tattgagaca aaaattatct atttgtatat atacataaca gggtaaatta ttcagttaag  43320
aaaaaaataa ttttatgaac tgcatgtata aatgaagttt atacagtaca gtggttctac  43380
aatctattta ttggacatgt ccatgaccag aagggaaaca gtcatttgcg cacaacttaa  43440
aaagtctgca ttacattcct tgataatgtt gtggtttgtt gccgttgcca agaactgaaa  43500
acataaaaag ttaaaaaaaa taataaattg catgctgctt taattgtgaa ttgataataa  43560
actgtcctct ttcagaaaac agaaaaaaaa cacacacaca cacaacaaaa atttgaacca  43620
aaacattccg tttacatttt agacagtaag tatcttcgtt cttgttagta ctatatctgt  43680
tttactgctt ttaacttctg atagcgttgg aattaaaaca atgtcaaggt gctgttgtca  43740
ttgctttact ggcttagggg atgggggatg gggggtatat ttttgtttgt tttgtgtttt  43800
tttttcgttt gtttgttttg ttttttagtt cccacaggga gtagagatgg ggaaagaatt  43860
cctacaatat atattctggc tgataaaaga tacatttgta tgttgtgaag atgtttgcaa  43920
tatcgatcag atgactagaa agtgaataaa aattaaggca actgaacaaa aaaatgctca  43980
cactccacat cccgtgatgc acctcccagg ccccgctcat tctttgggcg ttggtcagag  44040
taagctgctt ttgacggaag gacctatgtt tgctcagaac acattctttc ccccctccc   44100
cctctggtct cctctttgtt ttgttttaag gaagaaaaat cagttgcgcg ttctgaaata  44160
ttttaccact gctgtgaaca agtgaacaca ttgtgtcaca tcatgacact cgtataagca  44220
tggagaacag tgattttttt ttagaacaga aacaacaaa aaataacccc aaaatgaaga   44280
```

-continued

```
ttattttta tgaggagtga acatttgggt aaatcatggc taagcttaaa aaaaactcat  44340

ggtgaggctt aacaatgtct tgtaagcaaa aggtagagcc ctgtatcaac ccagaaacac  44400

ctagatcaga acaggaatcc acattgccag tgacatgaga ctgaacagcc aaatggaggc  44460

tatgtggagt tggcattgca tttaccggca gtgcgggagg aatttctgag tggccatccc  44520

aaggtctagg tggaggtggg gcatggtatt tgagacattc caaaacgaag gcctctgaag  44580

gacccttcag aggtggctct ggaatgacat gtgtcaagct gcttggacct cgtgctttaa  44640

gtgcctacat tatctaactg tgctcaagag gttctcgact ggaggaccac actcaagccg  44700

acttatgccc accatcccac ctctggataa ttttgcataa aattggatta gcctggagca  44760

ggttgggagc caaatgtggc atttgtgatc atgagattga tgcaatgaga tagaagatgt  44820

ttgctacctg aacacttatt gctttgaaac tagacttgag gaaaccaggg tttatctttt  44880

gagaactttt ggtaagggaa aagggaacag gaaaagaaac cccaaactca ggccgaatga  44940

tcaaggggac ccataggaaa tcttgtccag agacaagact tcgggaaggt gtctggacat  45000

tcagaacacc aagacttgaa ggtgccttgc tcaatggaag aggccaggac agagctgaca  45060

aaattttgct ccccagtgaa ggccacagca accttctgcc catcctgtct gttcatggag  45120

agggtccctg cctcacctct gccattttgg gttaggagaa gtcaagttgg gagcctgaaa  45180

tagtggttct tggaaaaatg gatccccagt gaaaactaga gctctaagcc cattcagccc  45240

atttcacacc tgaaaatgtt agtgatcacc acttggacca gcatccttaa gtatcagaaa  45300

gccccaagca attgctgcat cttagtaggg tgagggataa gcaaaagagg atgttcacca  45360

taacccagga atgaagatac catcagcaaa gaatttcaat ttgttcagtc tttcatttag  45420

agctagtctt tcacagtacc atctgaatac ctctttgaaa gaaggaagac tttacgtagt  45480

gtagatttgt tttgtgttgt ttgaaaatat tatctttgta attattttta atatgtaagg  45540

aatgcttgga atatctgctg tatgtcaact ttatgcagct tccttttgag ggacaaattt  45600

aaaacaaaca accccccatc acaaacttaa aggattgcaa gggccagatc tgttaagtgg  45660

tttcatagga gacacatcca gcaattgtgt ggtcagtggc tcttttaccc aataagatac  45720

atcacagtca catgcttgat ggtttatgtt gacctaagat ttattttgtt aaaatctctc  45780

tctgttgtgt tcgttcttgt tctgttttgt tttgtttttt aaagtcttgc tgtggtctct  45840

ttgtggcaga agtgtttcat gcatggcagc aggcctgttg cttttttatg gcgattccca  45900

ttgaaaatgt aagtaaatgt ctgtggcctt gttctctcta tggtaaagat attattcacc  45960

atgtaaaaca aaaaacaata tttattgtat tttagtatat ttatataatt atgttattga  46020

aaaaaattgg cattaaaact taaccgcatc agaagcctat tgtaaataca agttctattt  46080

aagtgtacta attaacatat aatatatgtt ttaaatatag aatttttaat gtttttaaat  46140

atattttcaa agtacataa                                               46159
```

TREATMENT OF BRAIN DERIVED NEUROTROPHIC FACTOR (BDNF) RELATED DISEASES BY INHIBITION OF NATURAL ANTISENSE TRANSCRIPT TO BDNF

CROSS REFERENCE

The present Application is a Divisional of U.S. Ser. No. 13/201,254 filed on Sep. 13, 2011, now U.S. Pat. Number 9,074,210, which is a National Stage Entry of International Application No. PCT/US2010/024075, filed Feb. 12, 2010, which claims priority U.S. Provisional Application No. 61/152,132, filed Feb. 12, 2009, which are all incorporated herein by reference in their entireties.

FIELD OF THE INVENTION

Embodiments of the invention comprise oligonucleotides modulating expression and/or function of BDNF and associated molecules.

BACKGROUND

DNA-RNA and RNA-RNA hybridization are important to many aspects of nucleic acid function including DNA replication, transcription, and translation. Hybridization is also central to a variety of technologies that either detect a particular nucleic acid or alter its expression. Antisense nucleotides, for example, disrupt gene expression by hybridizing to target RNA, thereby interfering with RNA splicing, transcription, translation, and replication. Antisense DNA has the added feature that DNA-RNA hybrids serve as a substrate for digestion by ribonuclease H, an activity that is present in most cell types. Antisense molecules can be delivered into cells, as is the case for oligodeoxynucleotides (ODNs), or they can be expressed from endogenous genes as RNA molecules. The FDA recently approved an antisense drug, VITRAVENE.TM. (for treatment of cytomegalovirus retinitis), reflecting that antisense has therapeutic utility.

SUMMARY

This Summary is provided to present a summary of the invention to briefly indicate the nature and substance of the invention. It is submitted with the understanding that it will not be used to interpret or limit the scope or meaning of the claims.

In one embodiment, the invention provides methods for inhibiting the action of a natural antisense transcript by using antisense oligonucleotide(s) targeted to any region of the natural antisense transcript resulting in up-regulation of the corresponding sense gene. It is also contemplated herein that inhibition of the natural antisense transcript can be achieved by siRNA, ribozymes and small molecules, which are considered to be within the scope of the present invention.

One embodiment provides a method of modulating function and/or expression of an BDNF polynucleotide in patient cells or tissues in vivo or in vitro comprising contacting said cells or tissues with an antisense oligonucleotide 5 to 30 nucleotides in length wherein said oligonucleotide has at least 50% sequence identity to a reverse complement of a polynucleotide comprising 5 to 30 consecutive nucleotides within nucleotides 1 to 3175 of SEQ ID NO: 2 (FIG. 3) thereby modulating function and/or expression of the BDNF polynucleotide in patient cells or tissues in vivo or in vitro.

In another preferred embodiment, an oligonucleotide targets a natural antisense sequence of BDNF polynucleotides, for example, nucleotides set forth in SEQ ID NO: 2, and any variants, alleles, homologs, mutants, derivatives, fragments and complementary sequences thereto. Examples of antisense oligonucleotides are set forth as SEQ ID NOS: 3 to 8 (FIG. 4).

Another embodiment provides a method of modulating function and/or expression of an BDNF polynucleotide in patient cells or tissues in vivo or in vitro comprising contacting said cells or tissues with an antisense oligonucleotide 5 to 30 nucleotides in length wherein said oligonucleotide has at least 50% sequence identity to a reverse complement of the an antisense of the BDNF polynucleotide; thereby modulating function and/or expression of the BDNF polynucleotide in patient cells or tissues in vivo or in vitro.

Another embodiment provides a method of modulating function and/or expression of an BDNF polynucleotide in patient cells or tissues in vivo or in vitro comprising contacting said cells or tissues with an antisense oligonucleotide 5 to 30 nucleotides in length wherein said oligonucleotide has at least 50% sequence identity to an antisense oligonucleotide to an BDNF antisense polynucleotide; thereby modulating function and/or expression of the BDNF polynucleotide in patient cells or tissues in vivo or in vitro.

In a preferred embodiment, a composition comprises one or more antisense oligonucleotides which bind to sense and/or antisense BDNF polynucleotides.

In another preferred embodiment, the oligonucleotides comprise one or more modified or substituted nucleotides.

In another preferred embodiment, the oligonucleotides comprise one or more modified bonds.

In yet another embodiment, the modified nucleotides comprise modified bases comprising phosphorothioate, methylphosphonate, peptide nucleic acids, 2'-O-methyl, fluoro- or carbon, methylene or other locked nucleic acid (LNA) molecules. Preferably, the modified nucleotides are locked nucleic acid molecules, including .alpha.-L-LNA.

In another preferred embodiment, the oligonucleotides are administered to a patient subcutaneously, intramuscularly, intravenously or intraperitoneally.

In another preferred embodiment, the oligonucleotides are administered in a pharmaceutical composition. A treatment regimen comprises administering the antisense compounds at least once to patient; however, this treatment can be modified to include multiple doses over a period of time. The treatment can be combined with one or more other types of therapies.

In another preferred embodiment, the oligonucleotides are encapsulated in a liposome or attached to a carrier molecule (e.g. cholesterol, TAT peptide).

Other aspects are described infra.

BRIEF DESCRIPTION OF THE DRAWINGS

FIG. 2 shows SEQ ID NO: 1: Homo sapiens brain-derived neurotrophic factor (BDNF), transcript variant 1, mRNA, (NCBI Accession No.: NM_170735) and SEQ ID NO: 11 shows the genomic sequence of BDNF (exons are shown in capital letters, introns in small).

FIG. 3 shows SEQ ID NO: 2: Natural BDNF antisense sequence (NR_002832.1) Homo sapiens BDNF opposite strand (non-protein coding) (BDNFOS), non-coding RNA.

FIG. 4 shows the antisense oligonucleotides. SEQ ID NOS: 3 to 8. * indicates phosphothioate bond and + indicates LNA modification.

FIG. 5 shows SEQ ID NOS: 9 and 10.

DETAILED DESCRIPTION

Figure 1A:
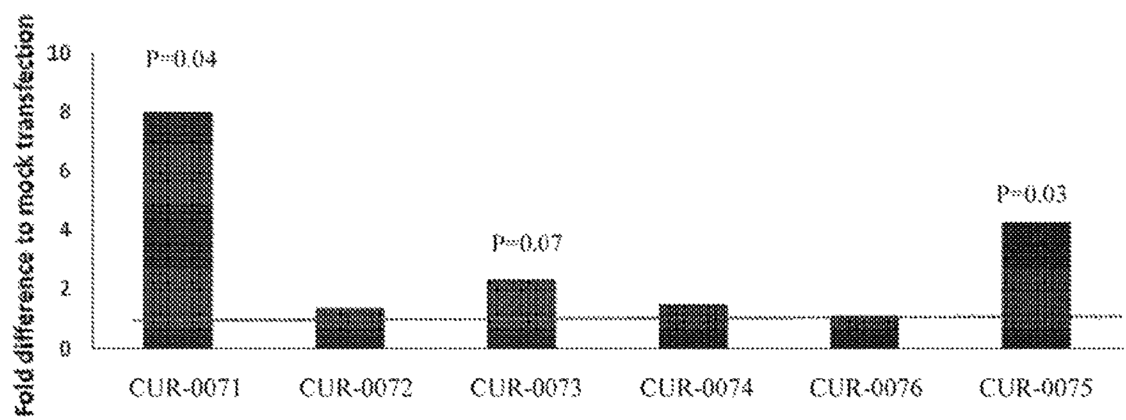
FIG. 1A: is a graph of real time PCR results showing the fold change+standard deviation in BDNF mRNA after treatment of HepG2 cells with LNA gapmer phosphorothioate oligonucleotides introduced using Lipofectamine 2000, as compared to control. Real time PCR results show that the levels of the BDNF mRNA in HepG2 cells are significantly increased 48 h after treatment with two of the LNA gapmers with fully phosphothioated backbone designed to BDNF antisense NM_170735 (CUR-0071, P=0.04, CUR-0073, P=0.07, CUR-0075, P=0.03). Bars denoted as CUR-0071, CUR-0072, CUR-0073, CUR-0074, CUR-0075 and CUR-0076 correspond to samples treated with SEQ ID NOS: 6, 7, 8, 5, 4 and 3, respectively.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced about one or more of the specific details or with other methods. The present invention is not limited by the ordering of acts or events, as some acts may occur in different orders and/or concurrently with other acts or events. Furthermore, not all illustrated acts or events are required to implement a methodology in accordance with the present invention.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes disclosed herein, which in some embodiments relate to mammalian nucleic acid and amino acid sequences are intended to encompass homologous and/or orthologous genes and gene products from other animals including, but not limited to other mammals, fish, amphibians, reptiles, and birds. In preferred embodiments, the genes or nucleic acid sequences are human.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "mRNA" means the presently known mRNA transcript(s) of a targeted gene, and any further transcripts which may be elucidated.

By "antisense oligonucleotides" or "antisense compound" is meant an RNA or DNA molecule that binds to another RNA or DNA (target RNA, DNA). For example, if it is an RNA oligonucleotide it binds to another RNA target by means of RNA-RNA interactions and alters the activity of the target RNA (Eguchi et al., (1991) Ann. Rev. Biochem. 60, 631-652). An antisense oligonucleotide can upregulate or downregulate expression and/or function of a particular polynucleotide. The definition is meant to include any foreign RNA or DNA molecule which is useful from a therapeutic, diagnostic, or other viewpoint. Such molecules include, for example, antisense RNA or DNA molecules, interference RNA (RNAi), micro RNA, decoy RNA molecules, siRNA, enzymatic RNA, therapeutic editing RNA and agonist and antagonist RNA, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

In the context of this invention, the term "oligonucleotide" refers to an oligomer or polymer of ribonucleic acid (RNA) or deoxyribonucleic acid (DNA) or mimetics thereof. The term "oligonucleotide", also includes linear or circular oligomers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like. Oligonucleotides are capable of specifically binding to a target polynucleotide by way of a regular pattern of monomer-tomonomer interactions, such as Watson-Crick type of base pairing, Hoogsteen or reverse Hoogsteen types of base pairing, or the like.

The oligonucleotide may be "chimeric", that is, composed of different regions. In the context of this invention "chimeric" compounds are oligonucleotides, which contain two or more chemical regions, for example, DNA region(s), RNA region(s), PNA region(s) etc. Each chemical region is made up of at least one monomer unit, i.e., a nucleotide in the case of an oligonucleotides compound. These oligonucleotides typically comprise at least one region wherein the oligonucleotide is modified in order to exhibit one or more desired properties. The desired properties of the oligonucleotide include, but are not limited, for example, to increased resistance to nuclease degradation, increased cellular uptake, and/or increased binding affinity for the target nucleic acid. Different regions of the oligonucleotide may therefore have different properties. The chimeric oligonucleotides of the present invention can be formed as mixed structures of two or more oligonucleotides, modified oligonucleotides, oligonucleosides and/or oligonucleotide analogs as described above.

The oligonucleotide can be composed of regions that can be linked in "register", that is, when the monomers are linked consecutively, as in native DNA, or linked via spacers. The spacers are intended to constitute a covalent "bridge" between the regions and have in preferred cases a length not exceeding about 100 carbon atoms. The spacers may carry different functionalities, for example, having positive or negative charge, carry special nucleic acid binding properties (intercalators, groove binders, toxins, fluorophors etc.), being lipophilic, inducing special secondary structures like, for example, alanine containing peptides that induce alpha-helices.

As used herein "BDNF" and "Brain derived neurotrophic factor" are inclusive of all family members, mutants, alleles, fragments, species, coding and noncoding sequences, sense and antisense polynucleotide strands, etc.

As used herein, the words 'Brain derived neurotrophic factor', 'Brain-derived neurotrophic factor' and BDNF, are used interchangeably in the present application.

As used herein, the term "oligonucleotide specific for" or "oligonucleotide which targets" refers to an oligonucleotide having a sequence (i) capable of forming a stable complex with a portion of the targeted gene, or (ii) capable of forming a stable duplex with a portion of a mRNA transcript of the targeted gene. Stability of the complexes and duplexes can be determined by theoretical calculations and/or in vitro assays. Exemplary assays for determining stability of hybridization complexes and duplexes are described in the Examples below.

As used herein, the term "target nucleic acid" encompasses DNA, RNA (comprising premRNA and mRNA) transcribed from such DNA, and also cDNA derived from such RNA, coding, noncoding sequences, sense or antisense polynucleotides. The specific hybridization of an oligomeric compound with its target nucleic acid interferes with the normal function of the nucleic acid. This modulation of function of a target nucleic acid by compounds, which specifically hybridize to it, is generally referred to as "antisense". The functions of DNA to be interfered include, for example, replication and transcription. The functions of RNA to be interfered, include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of an encoded product or oligonucleotides.

RNA interference "RNAi" is mediated by double stranded RNA (dsRNA) molecules that have sequence-specific homology to their "target" nucleic acid sequences (Caplen, N.J., et al. (2001) Proc. Natl. Acad. Sci. USA 98:9742-9747). In certain embodiments of the present invention, the mediators are 5-25 nucleotide "small interfering" RNA duplexes (siRNAs). The siRNAs are derived from the processing of dsRNA by an RNase enzyme known as Dicer (Bernstein, E., et al. (2001) Nature 409:363-366). siRNA duplex products are recruited into a multi-protein siRNA complex termed RISC (RNA Induced Silencing Complex). Without wishing to be bound by any particular theory, a RISC is then believed to be guided to a target nucleic acid (suitably mRNA), where the siRNA duplex interacts in a sequence-specific way to mediate cleavage in a catalytic fashion (Bernstein, E., et al. (2001) Nature 409:363-366; Boutla, A., et al. (2001) Curr. Biol. 11:1776-1780). Small interfering RNAs that can be used in accordance with the present invention can be synthesized and used according to procedures that are well known in the art and that will be familiar to the ordinarily skilled artisan. Small interfering RNAs for use in the methods of the present invention suitably comprise between about 1 to about 50 nucleotides (nt). In examples of non limiting embodiments, siRNAs can comprise about 5 to about 40 nt, about 5 to about 30 nt, about 10 to about 30 nt, about 15 to about 25 nt, or about 20-25 nucleotides.

Selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of oligonucleotides that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

By "enzymatic RNA" is meant an RNA molecule with enzymatic activity (Cech, (1988) J. American. Med. Assoc. 260, 3030-3035). Enzymatic nucleic acids (ribozymes) act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through base pairing, and once bound to the correct site, acts enzymatically to cut the target RNA.

By "decoy RNA" is meant an RNA molecule that mimics the natural binding domain for a ligand. The decoy RNA therefore competes with natural binding target for the binding of a specific ligand. For example, it has been shown that over-expression of HIV trans-activation response (TAR)

RNA can act as a "decoy" and efficiently binds HIV tat protein, thereby preventing it from binding to TAR sequences encoded in the HIV RNA (Sullenger et al. (1990) Cell, 63, 601-608). This is meant to be a specific example. Those in the art will recognize that this is but one example, and other embodiments can be readily generated using techniques generally known in the art.

As used herein, the term "monomers" typically indicates monomers linked by phosphodiester bonds or analogs thereof to form oligonucleotides ranging in size from a few monomeric units, e.g., from about 3-4, to about several hundreds of monomeric units. Analogs of phosphodiester linkages include: phosphorothioate, phosphorodithioate, methylphosphornates, phosphoroselenoate, phosphoramidate, and the like, as more fully described below.

The term "nucleotide" covers naturally occurring nucleotides as well as nonnaturally occurring nucleotides. It should be clear to the person skilled in the art that various nucleotides which previously have been considered "non-naturally occurring" have subsequently been found in nature. Thus, "nucleotides" includes not only the known purine and pyrimidine heterocycles-containing molecules, but also heterocyclic analogues and tautomers thereof. Illustrative examples of other types of nucleotides are molecules containing adenine, guanine, thymine, cytosine, uracil, purine, xanthine, diaminopurine, 8-oxo-N6-methyladenine, 7-deazaxanthine, 7-deazaguanine, N4,N4-ethanocytosin, N6,N6-ethano-2,6-diaminopurine, 5-methylcytosine, 5-(C3-C6)-alkynylcytosine, 5-fluorouracil, 5-bromouracil, pseudoisocytosine, 2-hydroxy-5-methyl-4-triazolopyridin, isocytosine, isoguanin, inosine and the "non-naturally occurring" nucleotides described in Benner et al., U.S. Pat. No. 5,432,272. The term "nucleotide" is intended to cover every and all of these examples as well as analogues and tautomers thereof. Especially interesting nucleotides are those containing adenine, guanine, thymine, cytosine, and uracil, which are considered as the naturally occurring nucleotides in relation to therapeutic and diagnostic application in humans. Nucleotides include the natural 2'-deoxy and 2'-hydroxyl sugars, e.g., as described in Kornberg and Baker, DNA Replication, 2nd Ed. (Freeman, San Francisco, 1992) as well as their analogs.

"Analogs" in reference to nucleotides includes synthetic nucleotides having modified base moieties and/or modified sugar moieties (see e.g., described generally by Scheit, Nucleotide Analogs, John Wiley, New York, 1980; Freier & Altmann, (1997) Nucl. Acid. Res., 25(22), 4429-4443, Toulme, J. J., (2001) Nature Biotechnology 19:17-18; Manoharan M., (1999) Biochemica et Biophysica Acta 1489:117-139; Freier S. M., (1997) Nucleic Acid Research, 25:4429-4443, Uhlman, E., (2000) Drug Discovery & Development, 3: 203-213, Herdewin P., (2000) Antisense & Nucleic Acid Drug Dev., 10:297-310); 2'-O, 3'-C-linked [3.2.0]bicycloarabinonucleosides (see e.g. N. K Christiensen., et al, (1998) J. Am. Chem. Soc., 120: 5458-5463; Prakash T P, Bhat B. (2007) Curr Top Med. Chem. 7(7): 641-9; Cho E J, et al. (2009) Annual Review of Analytical Chemistry, 2, 241-264). Such analogs include synthetic nucleotides designed to enhance binding properties, e.g., duplex or triplex stability, specificity, or the like.

As used herein, "hybridization" means the pairing of substantially complementary strands of oligomeric compounds. One mechanism of pairing involves hydrogen bonding, which may be Watson-Crick, Hoogsteen or reversed Hoogsteen hydrogen bonding, between complementary nucleoside or nucleotide bases (nucleotides) of the strands of oligomeric compounds. For example, adenine and thymine are complementary nucleotides which pair through the formation of hydrogen bonds. Hybridization can occur under varying circumstances.

An antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

As used herein, the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated. In general, stringent hybridization conditions comprise low concentrations (<0.15M) of salts with inorganic cations such as Na++ or K++ (i.e., low ionic strength), temperature higher than 20° C.-25° C. below the Tm of the oligomeric compound:target sequence complex, and the presence of denaturants such as formamide, dimethylformamide, dimethyl sulfoxide, or the detergent sodium dodecyl sulfate (SDS). For example, the hybridization rate decreases 1.1% for each 1% formamide. An example of a high stringency hybridization condition is 0.1.times. sodium chloride-sodium citrate buffer (SSC)/0.1% (w/v) SDS at 60° C. for 30 minutes.

"Complementary," as used herein, refers to the capacity for precise pairing between two nucleotides on one or two oligomeric strands. For example, if a nucleobase at a certain position of an antisense compound is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleotides which can hydrogen bond with each other. Thus, "specifically hybridizable" and "complementary" are terms which are used to indicate a sufficient degree of precise pairing or complementarity over a sufficient number of nucleotides such that stable and specific binding occurs between the oligomeric compound and a target nucleic acid.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure, mismatch or hairpin structure). The oligomeric compounds of the present invention comprise at least about 70%, or at least about 75%, or at least about 80%, or at least about 85%, or at least about 90%, or at least about 95%, or at least about 99% sequence complementarity to a target region within the target nucleic acid sequence to which they are targeted. For example, an antisense compound in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. As such, an antisense compound which is 18 nucleotides in length having 4 (four) noncomplementary nucleotides which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., (1990) J. Mol. Biol., 215, 403-410; Zhang and Madden, (1997) Genome Res., 7, 649-656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., (1981) 2, 482-489).

As used herein, the term "Thermal Melting Point (Tm)" refers to the temperature, under defined ionic strength, pH, and nucleic acid concentration, at which 50% of the oligonucleotides complementary to the target sequence hybridize to the target sequence at equilibrium. Typically, stringent conditions will be those in which the salt concentration is at least about 0.01 to 1.0 M Na ion concentration (or other salts) at pH 7.0 to 8.3 and the temperature is at least about 30° C. for short oligonucleotides (e.g., 10 to 50 nucleotide). Stringent conditions may also be achieved with the addition of destabilizing agents such as formamide.

As used herein, "modulation" means either an increase (stimulation) or a decrease (inhibition) in the expression of a gene.

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs,) or single base mutations in which the polynucleotide sequence varies by one base. The presence of SNPs may be indicative of, for example, a certain population with a propensity for a disease state, that is susceptibility versus resistance.

Derivative polynucleotides include nucleic acids subjected to chemical modification, for example, replacement of hydrogen by an alkyl, acyl, or amino group. Derivatives, e.g., derivative oligonucleotides, may comprise non-naturally-occurring portions, such as altered sugar moieties or inter-sugar linkages. Exemplary among these are phosphorothioate and other sulfur containing species which are known in the art. Derivative nucleic acids may also contain labels, including radionucleotides, enzymes, fluorescent agents, chemiluminescent agents, chromogenic agents, substrates, cofactors, inhibitors, magnetic particles, and the like.

A "derivative" polypeptide or peptide is one that is modified, for example, by glycosylation, pegylation, phosphorylation, sulfation, reduction alkylation, acylation, chemical coupling, or mild formalin treatment. A derivative may also be modified to contain a detectable label, either directly or indirectly, including, but not limited to, a radioisotope, fluorescent, and enzyme label.

As used herein, the term "animal" or "patient" is meant to include, for example, humans, sheep, elks, deer, mule deer, minks, mammals, monkeys, horses, cattle, pigs, goats, dogs, cats, rats, mice, birds, chicken, reptiles, fish, insects and arachnids.

"Mammal" covers warm blooded mammals that are typically under medical care (e.g., humans and domesticated animals). Examples include feline, canine, equine, bovine, and human, as well as just human.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

As used herein, the term "cancer" refers to any malignant tumor, particularly arising in the lung, kidney, or thyroid. The cancer manifests itself as a "tumor" or tissue comprising malignant cells of the cancer. Examples of tumors include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. As noted above, the invention specifically permits differential diagnosis of lung, kidney, and thyroid tumors.

Polynucleotide and Oligonucleotide Compositions and Molecules

Targets: In one embodiment, the targets comprise nucleic acid sequences of Brain derived neurotrophic factor (BDNF), including without limitation sense and/or antisense noncoding and/or coding sequences associated with BDNF.

Neurotrophins are a class of structurally related growth factors that promote neural survival and differentiation. They stimulate neurite outgrowth, suggesting that they can promote regeneration of injured neurons, and act as target-derived neurotrophic factors to stimulate collateral sprouting in target tissues that produce the neurotrophin (Korsching., (1993) J. Neurosci., 13: 2739). Brain-derived neurotrophic factor (BDNF) was initially characterized as a basic protein present in brain extracts and capable of increasing the survival of dorsal root ganglia (Leibrock., et al., (1989) Nature, 341:149). When axonal communication with the cell body is interrupted by injury, Schwann cells produce neurotrophic factors such as nerve growth factor (NGF) and BDNF. Neurotrophins are released from the Schwann cells and dispersed diffusely in gradient fashion around regenerating axons, which then extend distally along the neurotrophins' density gradient (Ide., (1996) Neurosci. Res., 25:101). Local application of BDNF to transected nerves in neonatal rats has been shown to prevent massive death of motor neurons that follows axotomy (DiStefano., et al., (1992) Neuron, 8:983; Oppenheim., et al., (1992) Nature, 360:755; Yan., et al., (1992) Nature, 360:753). The mRNA titer of BDNF increases to several times the normal level four days after axotomy and reaches its maximum at 4 weeks (Meyer., et al., (1992) J. Cell Biol. 119:45). Moreover, BDNF has been reported to enhance the survival of cholinergic neurons in culture (Nonomura, et al., (1995) Brain Res. 683:129).

Exemplary Brain derived neurotrophic factor (BDNF) mediated diseases and disorders which can be treated with cell/tissues regenerated from stem cells obtained using the antisense compounds comprise: a disease or a disorder associated with defective neurogenesis; a neurodegenerative disease or disorder (e.g., Alzheimer's disease, Parkinson's disease, Huntington's disease, amyotrophic lateral sclerosis etc.); a neuropsychiatric disorder (depression, schizophrenia, schizofreniform disorder, schizoaffective disorder, and delusional disorder; anxiety disorders such as panic disorder, phobias (including agoraphobia), an obsessive-compulsive disorder, a posttraumatic stress disorder, a bipolar disorder, anorexia nervosa, bulimia nervosa, an autoimmune disorder (e.g., multiple sclerosis) of the central nervous system, memory loss, a long term or a short term memory disorder, benign forgetfulness, a childhood learning disorder, close head injury, an attention deficit disorder, neuronal reaction to viral infection, brain damage, narcolepsy, a sleep disorder (e.g., circadian rhythm disorders, insomnia and narcolepsy); severance of nerves or nerve damage, severance of cerebrospinal nerve cord (CNS) and a damage to brain or nerve cells, a neurological deficit associated with AIDS, a motor and tic disorder characterized by motor and/or vocal tics (e.g., Tourette's disorder, chronic motor or vocal tic disorder, transient tic disorder, and stereotypic movement disorder), a substance abuse disorder (e.g., substance dependence, substance abuse and the sequalae of substance abuse/dependence, such as substance-induced psychological disorder, substance withdrawal and substance-induced dementia or amnestic disorder), traumatic brain injury, tinnitus, neuralgia (e.g., trigeminal neuralgia) pain (e.g chronic pain, chronic inflammatory pain, pain associated with arthritis, fibromyalgia, back pain, cancer-associated pain, pain associated with digestive disease, pain associated with Crohn's disease, pain associated with autoimmune disease, pain associated with endocrine disease, pain associated with diabetic neuropathy, phantom limb pain, spontaneous pain, chronic post-surgical pain, chronic temporomandibular pain, causalgia, post-herpetic neuralgia, AIDS-related pain, complex regional pain syndromes type I and II, trigeminal neuralgia, chronic back pain, pain associated with spinal cord injury, pain associated with drug intake and recurrent acute pain, neuropathic pain), inappropriate neuronal activity resulting in neurodysthesias in a disease such as diabetes, an MS and a motor neuron disease, ataxias, muscular rigidity (spasticity), temporomandibular joint dysfunction, Reward deficiency syndrome (RDS), neurotoxicity caused by alcohol or substance abuse (e.g., ecstacy, methamphetamine etc.), mental retardation or cognitive impairment (e.g., nonsyndromic X-linked mental retardation, fragile X syndrome, Down's syndrome, autism), aphasia, Bell's palsy, Creutzfeldt Jacob disease, encephalitis, age related macular degeneration, ondine syndrome, WAGR syndrome, hearing loss, Rett syndrome, epilepsy, spinal cord injury, stroke, hypoxia, ischemia, brain injury, optic nerve injury, diabetic neuropathy, peripheral neuropathy, nerve transplantation complications, motor neuron disease, peripheral nerve injury, obesity, a metabolic syndrome, cancer, asthma, an atopic disease, an allergic inflammation, eczema, a neuro-oncological disease or disorder, neuro-immunological disease or disorder and neuro-otological disease or disorder; and a disease or disorder associated with aging and senescence.

In a preferred embodiment, the oligonucleotides are specific for polynucleotides of BDNF, which includes, without limitation noncoding regions. The BDNF targets comprise variants of BDNF or BDNFOS; mutants of BDNF or BDNFOS, including SNPs; noncoding sequences of BDNF; alleles, fragments and the like. Preferably the oligonucleotide is an antisense RNA molecule.

In accordance with embodiments of the invention, the target nucleic acid molecule is not limited to BDNF polynucleotides alone but extends to any of the isoforms, receptors, homologs, non-coding regions and the like of BDNF.

In another preferred embodiment, an oligonucleotide targets a natural antisense sequence (natural antisense to the coding and non-coding regions) of BDNF targets, including, without limitation, variants, alleles, homologs, mutants, derivatives, fragments and complementary sequences thereto. Preferably the oligonucleotide is an antisense RNA or DNA molecule.

In another preferred embodiment, the oligomeric compounds of the present invention also include variants in which a different base is present at one or more of the nucleotide positions in the compound. For example, if the first nucleotide is an adenine, variants may be produced which contain thymidine, guanosine, cytidine or other natural or unnatural nucleotides at this position. This may be done at any of the positions of the antisense compound. These compounds are then tested using the methods described herein to determine their ability to inhibit expression of a target nucleic acid.

In some embodiments, homology, sequence identity or complementarity, between the antisense compound and target is from about 50% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired. Such conditions include, i.e., physiological conditions in the case of in vivo assays or therapeutic treatment, and conditions in which assays are performed in the case of in vitro assays.

An antisense compound, whether DNA, RNA, chimeric, substituted etc, is specifically hybridizable when binding of the compound to the target DNA or RNA molecule interferes with the normal function of the target DNA or RNA to cause a loss of utility, and there is a sufficient degree of complementarily to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

In another preferred embodiment, targeting of BDNF including without limitation, antisense sequences which are identified and expanded, using for example, PCR, hybridization etc., one or more of the sequences set forth as SEQ ID NO: 2, and the like, modulate the expression or function of BDNF. In one embodiment, expression or function is up-regulated as compared to a control. In another preferred embodiment, expression or function is down-regulated as compared to a control.

In another preferred embodiment, oligonucleotides comprise nucleic acid sequences set forth as SEQ ID NOS: 3 to 8 including antisense sequences which are identified and expanded, using for example, PCR, hybridization etc. These oligonucleotides can comprise one or more modified nucleotides, shorter or longer fragments, modified bonds and the like. Examples of modified bonds or internucleotide linkages comprise phosphorothioate, phosphorodithioate or the like. In another preferred embodiment, the nucleotides comprise a phosphorus derivative. The phosphorus derivative (or modified phosphate group) which may be attached to the sugar or sugar analog moiety in the modified oligonucleotides of the present invention may be a monophosphate, diphosphate, triphosphate, alkylphosphate, alkanephosphate, phosphorothioate and the like. The preparation of the above-noted phosphate analogs, and their incorporation into nucleotides, modified nucleotides and oligonucleotides, per se, is also known and need not be described here.

The specificity and sensitivity of antisense is also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In embodiments of the present invention oligomeric antisense compounds, particularly oligonucleotides, bind to target nucleic acid molecules and modulate the expression and/or function of molecules encoded by a target gene. The functions of DNA to be interfered comprise, for example, replication and transcription. The functions of RNA to be interfered comprise all vital functions such as, for example, translocation of the RNA to the site of protein translation, translation of protein from the RNA, splicing of the RNA to yield one or more mRNA species, and catalytic activity which may be engaged in or facilitated by the RNA. The functions may be up-regulated or inhibited depending on the functions desired.

The antisense compounds, include, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

Targeting an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes Brain derived neurotrophic factor (BDNF).

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

In a preferred embodiment, the antisense oligonucleotides bind to the natural antisense sequences of Brain derived neurotrophic factor (BDNF) and modulate the expression and/or function of Brain derived neurotrophic factor (BDNF) (SEQ ID NO: 1). Examples of antisense sequences include SEQ ID NOS: 2 to 8.

In another preferred embodiment, the antisense oligonucleotides bind to one or more segments of Brain derived neurotrophic factor (BDNF) polynucleotides and modulate the expression and/or function of Brain derived neurotrophic factor (BDNF). The segments comprise at least five consecutive nucleotides of the Brain derived neurotrophic factor (BDNF) sense or antisense polynucleotides.

In another preferred embodiment, the antisense oligonucleotides are specific for natural antisense sequences of Brain derived neurotrophic factor (BDNF) wherein binding of the oligonucleotides to the natural antisense sequences of Brain derived neurotrophic factor (BDNF) modulate expression and/or function of Brain derived neurotrophic factor (BDNF).

In another preferred embodiment, oligonucleotide compounds comprise sequences set forth as SEQ ID NOS: 3 to 8, antisense sequences which are identified and expanded, using for example, PCR, hybridization etc. These oligonucleotides can comprise one or more modified nucleotides, shorter or longer fragments, modified bonds and the like. Examples of modified bonds or internucleotide linkages comprise phosphorothioate, phosphorodithioate or the like.

In another preferred embodiment, the nucleotides comprise a phosphorus derivative. The phosphorus derivative (or modified phosphate group) which may be attached to the sugar or sugar analog moiety in the modified oligonucleotides of the present invention may be a monophosphate, diphosphate, triphosphate, alkylphosphate, alkanephosphate, phosphorothioate and the like. The preparation of the above-noted phosphate analogs, and their incorporation into nucleotides, modified nucleotides and oligonucleotides, per se, is also known and need not be described here.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes has a translation initiation codon having the RNA sequence 5'-GUG, 5'-UUG or 5'-CUG; and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding Brain derived neurotrophic factor (BDNF), regardless of the sequence(s) of such codons. A translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions that may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a targeted region is the intragenic region encompassing the translation initiation or termination codon of the open reading frame (ORF) of a gene.

Another target region includes the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene). Still another target region includes the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. Another target region for this invention is the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. In one embodiment, targeting splice sites, i.e., intron-exon junctions or exon-intron junctions, is particularly useful in situations where aberrant splicing is implicated in disease, or where an overproduction of a particular splice product is implicated in disease. An aberrant fusion junction due to rearrangement or deletion is another embodiment of a target site. mRNA transcripts produced via the process of splicing of two (or more) mRNAs from different gene sources are known as "fusion transcripts". Introns can be effectively targeted using antisense compounds targeted to, for example, DNA or pre-mRNA.

In another preferred embodiment, the antisense oligonucleotides bind to coding and/or non-coding regions of a target polynucleotide and modulate the expression and/or function of the target molecule.

In another preferred embodiment, the antisense oligonucleotides bind to natural antisense polynucleotides and modulate the expression and/or function of the target molecule.

In another preferred embodiment, the antisense oligonucleotides bind to sense polynucleotides and modulate the expression and/or function of the target molecule.

Alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

Variants can be produced through the use of alternative signals to start or stop transcription. Pre-mRNAs and mRNAs can possess more than one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also embodiments of target nucleic acids.

The locations on the target nucleic acid to which the antisense compounds hybridize are defined as at least a 5-nucleotide long portion of a target region to which an active antisense compound is targeted.

While the specific sequences of certain exemplary target segments are set forth herein, one of skill in the art will recognize that these serve to illustrate and describe particular embodiments within the scope of the present invention. Additional target segments are readily identifiable by one having ordinary skill in the art in view of this disclosure.

Target segments 5-100 nucleotides in length comprising a stretch of at least five (5) consecutive nucleotides selected from within the illustrative preferred target segments are considered to be suitable for targeting as well.

Target segments can include DNA or RNA sequences that comprise at least the 5 consecutive nucleotides from the 5'-terminus of one of the illustrative preferred target segments (the remaining nucleotides being a consecutive stretch of the same DNA or RNA beginning immediately upstream of the 5'-terminus of the target segment and continuing until the DNA or RNA contains about 5 to about 100 nucleotides). Similarly preferred target segments are represented by DNA or RNA sequences that comprise at least the 5 consecutive nucleotides from the 3'-terminus of one of the illustrative preferred target segments (the remaining nucleotides being a consecutive stretch of the same DNA or RNA beginning immediately downstream of the 3'-terminus of the target segment and continuing until the DNA or RNA contains about 5 to about 100 nucleotides). One having skill in the art armed with the target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

In embodiments of the invention the oligonucleotides bind to an antisense strand of a particular target. The oligonucleotides are at least 5 nucleotides in length and can be synthesized so each oligonucleotide targets overlapping sequences such that oligonucleotides are synthesized to cover the entire length of the target polynucleotide. The targets also include coding as well as non coding regions.

In one embodiment, it is preferred to target specific nucleic acids by antisense oligonucleotides. Targeting an antisense compound to a particular nucleic acid, is a multistep process. The process usually begins with the identification of a nucleic acid sequence whose function is to be modulated. This may be, for example, a cellular gene (or mRNA transcribed from the gene) whose expression is associated with a particular disorder or disease state, or a non coding polynucleotide such as for example, non coding RNA (ncRNA).

RNAs can be classified into (1) messenger RNAs (mRNAs), which are translated into proteins, and (2) non-protein-coding RNAs (ncRNAs). ncRNAs comprise microRNAs, antisense transcripts and other Transcriptional Units (TU) containing a high density of stop codons and lacking any extensive "Open Reading Frame". Many ncRNAs appear to start from initiation sites in 3' untranslated regions (3'UTRs) of protein-coding loci. ncRNAs are often rare and at least half of the ncRNAs that have been sequenced by the FANTOM consortium seem not to be polyadenylated. Most researchers have for obvious reasons focused on polyadenylated mRNAs that are processed and exported to the cytoplasm. Recently, it was shown that the set of non-polyadenylated nuclear RNAs may be very large, and that many such transcripts arise from so-called intergenic regions (Cheng, J. et al. (2005) Science 308 (5725), 1149-1154; Kapranov, P. et al. (2005). Genome Res 15 (7), 987-997). The mechanism by which ncRNAs may regulate gene expression is by base pairing with target transcripts. The RNAs that function by base pairing can be grouped into (1) cis encoded RNAs that are encoded at the same genetic location, but on the opposite strand to the RNAs they act upon and therefore display perfect complementarity to their target, and (2) trans-encoded RNAs that are encoded at a chromosomal location distinct from the RNAs they act upon and generally do not exhibit perfect base-pairing potential with their targets.

Without wishing to be bound by theory, perturbation of an antisense polynucleotide by the antisense oligonucleotides described herein can alter the expression of the corresponding sense messenger RNAs. However, this regulation can either be discordant (antisense knockdown results in messenger RNA elevation) or concordant (antisense knockdown results in concomitant messenger RNA reduction). In these cases, antisense oligonucleotides can be targeted to overlapping or non-overlapping parts of the antisense transcript resulting in its knockdown or sequestration. Coding as well as non-coding antisense can be targeted in an identical manner and that either category is capable of regulating the corresponding sense transcripts-either in a concordant or disconcordant manner. The strategies that are employed in identifying new oligonucleotides for use against a target can be based on the knockdown of antisense RNA transcripts by antisense oligonucleotides or any other means of modulating the desired target.

Strategy 1: In the case of discordant regulation, knocking down the antisense transcript elevates the expression of the conventional (sense) gene. Should that latter gene encode for a known or putative drug target, then knockdown of its antisense counterpart could conceivably mimic the action of a receptor agonist or an enzyme stimulant.

Strategy 2: In the case of concordant regulation, one could concomitantly knock down both antisense and sense transcripts and thereby achieve synergistic reduction of the conventional (sense) gene expression. If, for example, an antisense oligonucleotide is used to achieve knockdown, then this strategy can be used to apply one antisense oligonucleotide targeted to the sense transcript and another antisense oligonucleotide to the corresponding antisense transcript, or a single energetically symmetric antisense oligonucleotide that simultaneously targets overlapping sense and antisense transcripts.

According to the present invention, antisense compounds include antisense oligonucleotides, ribozymes, external guide sequence (EGS) oligonucleotides, siRNA compounds, single- or double-stranded RNA interference (RNAi) compounds such as siRNA compounds, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, doublestranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines, however, in some embodiments, the gene expression or function is up regulated. When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

Once introduced to a system, the compounds of the invention may elicit the action of one or more enzymes or structural proteins to effect cleavage or other modification of the target nucleic acid or may work via occupancy-based mechanisms. In general, nucleic acids (including oligonucleotides) may be described as “DNA-like” (i.e., generally having one or more 2'-deoxy sugars and, generally, T rather than U bases) or “RNA-like” (i.e., generally having one or more 2'-hydroxyl or 2'-modified sugars and, generally U rather than T bases). Nucleic acid helices can adopt more than one type of structure, most commonly the A- and B-forms. It is believed that, in general, oligonucleotides which have B-form-like structure are “DNA-like” and those which have A-formlike structure are “RNA-like.” In some (chimeric) embodiments, an antisense compound may contain both A- and B-form regions.

In another preferred embodiment, the desired oligonucleotides or antisense compounds, comprise at least one of: antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof.

dsRNA can also activate gene expression, a mechanism that has been termed “small RNA-induced gene activation” or RNAa. dsRNAs targeting gene promoters induce potent transcriptional activation of associated genes. RNAa was demonstrated in human cells using synthetic dsRNAs, termed “small activating RNAs” (saRNAs). It is currently not known whether RNAa is conserved in other organisms.

Small double-stranded RNA (dsRNA), such as small interfering RNA (siRNA) and microRNA (miRNA), have been found to be the trigger of an evolutionary conserved mechanism known as RNA interference (RNAi). RNAi invariably leads to gene silencing via remodeling chromatin to thereby suppress transcription, degrading complementary mRNA, or blocking protein translation. However, in instances described in detail in the examples section which follows, oligonucleotides are shown to increase the expression and/or function of the Brain derived neurotrophic factor (BDNF) polynucleotides and encoded products thereof dsRNAs may also act as small activating RNAs (saRNA). Without wishing to be bound by theory, by targeting sequences in gene promoters, saRNAs would induce target gene expression in a phenomenon referred to as dsRNA-induced transcriptional activation (RNAa).

In a further embodiment, the “preferred target segments” identified herein may be employed in a screen for additional compounds that modulate the expression of Brain derived neurotrophic factor (BDNF) polynucleotides. “Modulators” are those compounds that decrease or increase the expression of a nucleic acid molecule encoding Brain derived neurotrophic factor (BDNF) and which comprise at least a 5-nucleotide portion that is complementary to a preferred target segment. The screening method comprises the steps of contacting a preferred target segment of a nucleic acid molecule encoding sense or natural antisense polynucleotides of Brain derived neurotrophic factor (BDNF) with one or more candidate modulators, and selecting for one or more candidate modulators which decrease or increase the expression of a nucleic acid molecule encoding Brain derived neurotrophic factor (BDNF) polynucleotides, e.g. SEQ ID NOS: 3 to 8. Once it is shown that the candidate modulator or modulators are capable of modulating (e.g. either decreasing or increasing) the expression of a nucleic acid molecule encoding Brain derived neurotrophic factor (BDNF) polynucleotides, the modulator may then be employed in further investigative studies of the function of Brain derived neurotrophic factor (BDNF) polynucleotides, or for use as a research, diagnostic, or therapeutic agent in accordance with the present invention.

Targeting the natural antisense sequence preferably modulates the function of the target gene. For example, the BDNF gene (e.g. accession number NM_170735, FIG. 2). In a preferred embodiment, the target is an antisense polynucleotide of the BDNF gene. In a preferred embodiment, an antisense oligonucleotide targets sense and/or natural antisense sequences of Brain derived neurotrophic factor (BDNF) polynucleotides (e.g. accession number NM_170735, FIG. 2), variants, alleles, isoforms, homologs, mutants, derivatives, fragments and complementary sequences thereto. Preferably the oligonucleotide is an antisense molecule and the targets include coding and noncoding regions of antisense and/or sense BDNF polynucleotides.

The preferred target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processing via an antisense mechanism. Moreover, the double-stranded moieties may be subject to chemical modifications (Fire et al., (1998) Nature, 391, 806-811; Timmons and Fire, (1998) Nature, 395, 854; Timmons et al., (2001) Gene, 263, 103-112; Tabara et al., (1998) Science, 282, 430-431; Montgomery et al., (1998) Proc. Natl. Acad. Sci. USA, 95, 15502-15507; Tuschl et al., (1999) Genes Dev., 13, 3191-3197; Elbashir et al., (2001) Nature, 411, 494-498; Elbashir et al., (2001) Genes Dev. 15, 188-200). For example, such double-stranded moieties have been shown to inhibit the target by the classical hybridization of antisense strand of the duplex to the target, thereby triggering enzymatic degradation of the target (Tijsterman et al., (2002) Science, 295, 694-697).

In a preferred embodiment, an antisense oligonucleotide targets Brain derived neurotrophic factor (BDNF) polynucleotides (e.g. accession number NM_170735), variants, alleles, isoforms, homologs, mutants, derivatives, fragments and complementary sequences thereto. Preferably the oligonucleotide is an antisense molecule.

In accordance with embodiments of the invention, the target nucleic acid molecule is not limited to Brain derived neurotrophic factor (BDNF) alone but extends to any of the isoforms, receptors, homologs and the like of Brain derived neurotrophic factor (BDNF) molecules.

In another preferred embodiment, an oligonucleotide targets a natural antisense sequence of BDNF polynucleotides, for example, polynucleotides set forth as SEQ ID NO: 2, and any variants, alleles, homologs, mutants, derivatives, fragments and complementary sequences thereto. Examples of antisense oligonucleotides are set forth as SEQ ID NOS: 3 to 8.

In one embodiment, the oligonucleotides are complementary to or bind to nucleic acid sequences of Brain derived neurotrophic factor (BDNF) antisense, including without limitation noncoding sense and/or antisense sequences associated with Brain derived neurotrophic factor (BDNF) polynucleotides and modulate expression and/or function of Brain derived neurotrophic factor (BDNF) molecules.

In another preferred embodiment, the oligonucleotides are complementary to or bind to nucleic acid sequences of BDNF natural antisense, set forth as SEQ ID NO: 2 and modulate expression and/or function of BDNF molecules.

In a preferred embodiment, oligonucleotides comprise sequences of at least 5 consecutive nucleotides of SEQ ID NOS: 3 to 8 and modulate expression and/or function of Brain derived neurotrophic factor (BDNF) molecules.

The polynucleotide targets comprise BDNF, including family members thereof, variants of BDNF; mutants of BDNF, including SNPs; noncoding sequences of BDNF; alleles of BDNF; species variants, fragments and the like. Preferably the oligonucleotide is an antisense molecule.

In another preferred embodiment, the oligonucleotide targeting Brain derived neurotrophic factor (BDNF) polynucleotides, comprise: antisense RNA, interference RNA (RNAi), short interfering RNA (siRNA); micro interfering RNA (miRNA); a small, temporal RNA (stRNA); or a short, hairpin RNA (shRNA); small RNA-induced gene activation (RNAa); or, small activating RNA (saRNA).

In another preferred embodiment, targeting of Brain derived neurotrophic factor (BDNF) polynucleotides, e.g. SEQ ID NO: 2, modulates the expression or function of these targets. In one embodiment, expression or function is up-regulated as compared to a control. In another preferred embodiment, expression or function is down-regulated as compared to a control.

In another preferred embodiment, antisense compounds comprise sequences set forth as SEQ ID NOS: 3 to 8. These oligonucleotides can comprise one or more modified nucleotides, shorter or longer fragments, modified bonds and the like.

In another preferred embodiment, SEQ ID NOS: 3 to 8 comprise one or more LNA nucleotides.

Table 1 shows exemplary antisense oligonucleotides useful in the methods of the invention.

| Sequence ID | Oligo name | Sequence |
|---|---|---|
| SEQ ID NO: 3 | CUR-0076 | C* + T* + T*G*A*A*T*T*G* T*T*T* + G* + T* + A |
| SEQ ID NO: 4 | CUR-0075 | A* + G* + T*T*G*C*A*A*G* A*G*T* + T * +G* + G |

-continued

| Sequence ID | Oligo name | Sequence |
|---|---|---|
| SEQ ID NO: 5 | CUR-0074 | A* + T* + C*T*G*T*T*C*T* G*C*T* + G* + T* + C |
| SEQ ID NO: 6 | CUR-0071 | C* + A* + T*A*T*T*C*T*T* G*G*A* + C* +G* + A |
| SEQ ID NO: 7 | CUR-0072 | T* + G* + T*G*C*T*G*T*T* G*T*A* + A* + G* + A |
| SEQ ID NO: 8 | CUR-0073 | T* + G* + A*C*A*G*A*G*G* A*G*T* + A* + T* + T |

The modulation of a desired target nucleic acid can be carried out in several ways known in the art. For example, antisense oligonucleotides, siRNA etc. Enzymatic nucleic acid molecules (e.g., ribozymes) are nucleic acid molecules capable of catalyzing one or more of a variety of reactions, including the ability to repeatedly cleave other separate nucleic acid molecules in a nucleotide base sequence-specific manner. Such enzymatic nucleic acid molecules can be used, for example, to target virtually any RNA transcript (Zaug et al., 324, Nature 429 1986; Cech, 260 JAMA 3030, 1988; and Jefferies et al., 17 Nucleic Acids Research 1371, 1989).

Because of their sequence-specificity, trans-cleaving enzymatic nucleic acid molecules show promise as therapeutic agents for human disease (Usman & McSwiggen, (1995) Ann. Rep. Med. Chem. 30, 285-294; Christoffersen and Marr, (1995) J. Med. Chem. 38, 2023-2037). Enzymatic nucleic acid molecules can be designed to cleave specific RNA targets within the background of cellular RNA. Such a cleavage event renders the mRNA non-functional and abrogates protein expression from that RNA. In this manner, synthesis of a protein associated with a disease state can be selectively inhibited.

In general, enzymatic nucleic acids with RNA cleaving activity act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel, (1979) Proc. R. Soc. London, B 205, 435) have been used to evolve new nucleic acid catalysts capable of catalyzing a variety of reactions, such as cleavage and ligation of phosphodiester linkages and amide linkages, (Joyce, (1989) Gene, 82, 83-87; Beaudry et al., (1992) Science 257, 635-641; Joyce, (1992) Scientific American 267, 90-97; Breaker et al., (1994) TIBTECH 12, 268; Bartel et al., (1993) Science 261:1411-1418; Szostak, (1993) TIBS 17, 89-93; Kumar et al., (1995) FASEB J., 9, 1183; Breaker, (1996) Curr. Op. Biotech., 7, 442).

The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 min-1 in the presence of saturating (10 mM) concentrations of Mg2+ cofactor. An artificial "RNA ligase" ribozyme has been shown to catalyze the corresponding self-modification reaction with a rate of about 100 min-1. In addition, it is known that certain modified hammerhead ribozymes that have substrate binding arms made of DNA catalyze RNA cleavage with multiple turn-over rates that approach 100 min-1. Finally, replacement of a specific residue within the catalytic core of the hammerhead with certain nucleotide analogues gives modified ribozymes that show as much as a 10-fold improvement in catalytic rate. These findings demonstrate that ribozymes can promote chemical transformations with catalytic rates that are significantly greater than those displayed in vitro by most natural self-cleaving ribozymes. It is then possible that the structures of certain selfcleaving ribozymes may be optimized to give maximal catalytic activity, or that entirely new RNA motifs can be made that display significantly faster rates for RNA phosphodiester cleavage.

Intermolecular cleavage of an RNA substrate by an RNA catalyst that fits the "hammerhead" model was first shown in 1987 (Uhlenbeck, O. C. (1987) Nature, 328: 596-600). The RNA catalyst was recovered and reacted with multiple RNA molecules, demonstrating that it was truly catalytic.

Catalytic RNAs designed based on the "hammerhead" motif have been used to cleave specific target sequences by making appropriate base changes in the catalytic RNA to maintain necessary base pairing with the target sequences (Haseloff and Gerlach, (1988) Nature, 334, 585; Walbot and Bruening, (1988) Nature, 334, 196; Uhlenbeck, O. C. (1987) Nature, 328: 596-600; Koizumi, M., et al. (1988) FEBS Lett., 228: 228-230). This has allowed use of the catalytic RNA to cleave specific target sequences and indicates that catalytic RNAs designed according to the "hammerhead" model may possibly cleave specific substrate RNAs in vivo. (see Haseloff and Gerlach, (1988) Nature, 334, 585; Walbot and Bruening, (1988) Nature, 334, 196; Uhlenbeck, O. C. (1987) Nature, 328: 596-600).

RNA interference (RNAi) has become a powerful tool for modulating gene expression in mammals and mammalian cells. This approach requires the delivery of small interfering RNA (siRNA) either as RNA itself or as DNA, using an expression plasmid or virus and the coding sequence for small hairpin RNAs that are processed to siRNAs. This system enables efficient transport of the pre-siRNAs to the cytoplasm where they are active and permit the use of regulated and tissue specific promoters for gene expression.

In a preferred embodiment, an oligonucleotide or antisense compound comprises an oligomer or polymer of ribonucleic acid (RNA) and/or deoxyribonucleic acid (DNA), or a mimetic, chimera, analog or homolog thereof. This term includes oligonucleotides composed of naturally occurring nucleotides, sugars and covalent internucleoside (backbone) linkages as well as oligonucleotides having non-naturally occurring portions which function similarly. Such modified or substituted oligonucleotides are often desired over native forms because of desirable properties such as, for example, enhanced cellular uptake, enhanced affinity for a target nucleic acid and increased stability in the presence of nucleases.

According to the present invention, the oligonucleotides or "antisense compounds" include antisense oligonucleotides (e.g. RNA, DNA, mimetic, chimera, analog or homolog thereof), ribozymes, external guide sequence (EGS) oligonucleotides, siRNA compounds, single- or double-stranded RNA interference (RNAi) compounds such as siRNA compounds, saRNA, aRNA, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, double-stranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines (Hammond et al., (1991) Nat. Rev. Genet., 2, 110-119; Matzke et al., (2001) Curr. Opin. Genet. Dev., 11, 221-227; Sharp, (2001) Genes Dev., 15, 485-490). When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

Once introduced to a system, the compounds of the invention may elicit the action of one or more enzymes or structural proteins to effect cleavage or other modification of the target nucleic acid or may work via occupancy-based mechanisms. In general, nucleic acids (including oligonucleotides) may be described as "DNA-like" (i.e., generally having one or more 2'-deoxy sugars and, generally, T rather than U bases) or "RNA-like" (i.e., generally having one or more 2'-hydroxyl or 2'-modified sugars and, generally U rather than T bases). Nucleic acid helices can adopt more than one type of structure, most commonly the A- and B-forms. It is believed that, in general, oligonucleotides which have B-form-like structure are "DNA-like" and those which have A-formlike structure are "RNA-like." In some (chimeric) embodiments, an antisense compound may contain both A- and B-form regions.

The antisense compounds in accordance with this invention can comprise an antisense portion from about 5 to about 80 nucleotides (i.e. from about 5 to about 80 linked nucleosides) in length. This refers to the length of the antisense strand or portion of the antisense compound. In other words, a single-stranded antisense compound of the invention comprises from 5 to about 80 nucleotides, and a double-stranded antisense compound of the invention (such as a dsRNA, for example) comprises a sense and an antisense strand or portion of 5 to about 80 nucleotides in length. One of ordinary skill in the art will appreciate that this comprehends antisense portions of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides in length, or any range therewithin.

In one embodiment, the antisense compounds of the invention have antisense portions of 10 to 50 nucleotides in length. One having ordinary skill in the art will appreciate that this embodies oligonucleotides having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the oligonucleotides are 15 nucleotides in length.

In one embodiment, the antisense or oligonucleotide compounds of the invention have antisense portions of 12 or 13 to 30 nucleotides in length. One having ordinary skill in the art will appreciate that this embodies antisense compounds having antisense portions of 12, 13, 14, 15, 16, 17, 18, 19, 20, 21, 22, 23, 24, 25, 26, 27, 28, 29 or 30 nucleotides in length, or any range therewithin.

In another preferred embodiment, the oligomeric compounds of the present invention also include variants in which a different base is present at one or more of the nucleotide positions in the compound. For example, if the first nucleotide is an adenosine, variants may be produced which contain thymidine, guanosine or cytidine at this position. This may be done at any of the positions of the antisense or dsRNA compounds. These compounds are then tested using the methods described herein to determine their ability to inhibit expression of a target nucleic acid.

In some embodiments, homology, sequence identity or complementarity, between the antisense compound and target is from about 40% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

In another preferred embodiment, the antisense oligonucleotides, such as for example, nucleic acid molecules set forth in SEQ ID NOS: 2 to 8 comprise one or more substitutions or modifications. In one embodiment, the nucleotides are substituted with locked nucleic acids (LNA).

In another preferred embodiment, the oligonucleotides target one or more regions of the nucleic acid molecules sense and/or antisense of coding and/or non-coding sequences associated with BDNF and the sequences set forth as SEQ ID NOS: 1, 2. The oligonucleotides are also targeted to overlapping regions of SEQ ID NOS: 1, 2.

Certain preferred oligonucleotides of this invention are chimeric oligonucleotides. "Chimeric oligonucleotides" or "chimeras," in the context of this invention, are oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense modulation of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art. In one preferred embodiment, a chimeric oligonucleotide comprises at least one region modified to increase target binding affinity, and, usually, a region that acts as a substrate for RNAse H. Affinity of an oligonucleotide for its target (in this case, a nucleic acid encoding ras) is routinely determined by measuring the Tm of an oligonucleotide/target pair, which is the temperature at which the oligonucleotide and target dissociate; dissociation is detected spectrophotometrically. The higher the Tm, the greater is the affinity of the oligonucleotide for the target.

Chimeric antisense compounds of the invention may be formed as composite structures of two or more oligonucleotides, modified oligonucleotides, oligonucleosides and/or oligonucleotides mimetics as described above. Such; compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In another preferred embodiment, the region of the oligonucleotide which is modified comprises at least one nucleotide modified at the 2' position of the sugar, most preferably a 2'-Oalkyl, 2'-O-alkyl-O-alkyl or 2'-fluoro-modified nucleotide. In other preferred embodiments, RNA modifications include 2'-fluoro, 2'-amino and 2' 0-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target. The effect of such increased affinity is to greatly enhance RNAi oligonucleotide inhibition of gene expression. RNAse H is a cellular endonuclease that cleaves the RNA strand of RNA:DNA duplexes; activation of this enzyme therefore results in cleavage of the RNA target, and thus can greatly enhance the efficiency of RNAi inhibition. Cleavage of the RNA target can be routinely demonstrated by gel electrophoresis. In another preferred embodiment, the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. Oligonucleotides which contain at least one phosphorothioate modification are presently more preferred. In some cases, oligonucleotide modifications which enhance target binding affinity are also, independently, able to enhance nuclease resistance. Some desirable modifications can be found in De Mesmaeker et al. (1995) Acc. Chem. Res., 28:366-374.

Specific examples of some preferred oligonucleotides envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly CH2—NH—O—CH2, CH, —N(CH3)—O—CH2 [known as a methylene (methylimino) or MMI backbone], CH2—O—N(CH3)—CH2, CH2—N(CH3)—N (CH3)—CH2 and O—N(CH3)—CH2—CH2 backbones, wherein the native phosphodiester backbone is represented as O—P—O—CH1). The amide backbones disclosed by De Mesmaeker et al. (1995) Acc. Chem. Res. 28:366-374 are also preferred. Also preferred are oligonucleotides having morpholino backbone structures (Summerton and Weller, U.S. Pat. No. 5,034,506). In other preferred embodiments, such as the peptide nucleic acid (PNA) backbone, the phosphodiester backbone of the oligonucleotide is replaced with a polyamide backbone, the nucleotides being bound directly or indirectly to the aza nitrogen atoms of the polyamide backbone (Nielsen et al. (1991) Science 254, 1497). Oligonucleotides may also comprise one or more substituted sugar moieties. Preferred oligonucleotides comprise one of the following at the 2' position: OH, SH, SCH3, F, OCN, OCH3OCH3, OCH3O (CH2)n CH3, O(CH2)nNH2 or O(CH2)nCH3 where n is from 1 to about 10; C1 to C10 lower alkyl, alkoxyalkoxy, substituted lower alkyl, alkaryl or aralkyl; Cl; Br; CN; CF3; OCF3; O—, S—, or N-alkyl; O—, S—, or N-alkenyl; SOCH3; SO2CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—CH2CH2OCH3, also known as 2'-O-(2-methoxyethyl)] (Martin et al., (1995) Hely. Chim. Acta, 78, 486). Other preferred modifications include 2'-methoxy (2'-O—CH3), 2'-propoxy (2'-OCH2CH2CH3) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides may also include, additionally or alternatively, nucleobase (often referred to in the art simply as "base") modifications or substitutions. As used herein, "unmodified" or "natural" nucleotides include adenine (A), guanine (G), thymine (T), cytosine (C) and uracil (U). Modified nucleotides include nucleotides found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl (HMC) and gentobiosyl HMC, as well as synthetic nucleotides, e.g., 2-aminoadenine, 2-(methylamino)adenine, 2-(imidazolylalkyl)adenine, 2-(aminoalklyamino)adenine or other hetero-substituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. (Kornberg, A., DNA Replication, W. H. Freeman & Co., San Francisco, 1980, pp 75-77; Gebeyehu, G., (1987) et al. Nucl. Acids Res. 15:4513). A "universal" base known in the art, e.g., inosine, may be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are presently preferred base substitutions.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger et al., (1989) Proc. Natl. Acad. Sci. USA 86, 6553), cholic acid (Manoharan et al. (1994) Bioorg. Med. Chem. Let. 4, 1053), a thioether, e.g., hexyl-5-tritylthiol (Manoharan et al. (1992) Ann. N.Y. Acad. Sci. 660, 306; Manoharan et al. (1993) Bioorg. Med. Chem. Let. 3, 2765), a thiocholesterol (Oberhauser et al., (1992) Nucl. Acids Res. 20, 533), an aliphatic chain, e.g., dodecandiol or undecyl residues (Saison-Behmoaras et al. EMBO J. 1991, 10, 111; Kabanov et al. (1990) FEBS Lett. 259, 327; Svinarchuk et al. (1993) Biochimie 75, 49), a phospholipid, e.g., di-hexadecyl-rac-glycerol or triethylammonium 1,2-di-O-hexadecyl-rac-glycero-3-H-phosphonate (Manoharan et al. (1995) Tetrahedron Lett. 36, 3651; Shea et al. (1990) Nucl. Acids Res. 18, 3777), a polyamine or a polyethylene glycol chain (Manoharan et al. (1995) Nucleosides & Nucleotides, 14, 969), or adamantane acetic acid (Manoharan et al. (1995) Tetrahedron Lett. 36, 3651). Oligonucleotides comprising lipophilic moieties, and methods for preparing such oligonucleotides are known in the art, for example, U.S. Pat. Nos. 5,138,045, 5,218,105 and 5,459, 255.

It is not necessary for all positions in a given oligonucleotide to be uniformly modified, and in fact more than one of the aforementioned modifications may be incorporated in a single oligonucleotide or even at within a single nucleoside within an oligonucleotide. The present invention also includes oligonucleotides which are chimeric oligonucleotides as hereinbefore defined.

In another embodiment, the nucleic acid molecule of the present invention is conjugated with another moiety including but not limited to abasic nucleotides, polyether, polyamine, polyamides, peptides, carbohydrates, lipid, or polyhydrocarbon compounds. Those skilled in the art will recognize that these molecules can be linked to one or more of any nucleotides comprising the nucleic acid molecule at several positions on the sugar, base or phosphate group.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of one of ordinary skill in the art. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other modified oligonucleotides such as cholesterol-modified oligonucleotides.

In accordance with the invention, use of modifications such as the use of LNA monomers to enhance the potency, specificity and duration of action and broaden the routes of administration of oligonucleotides comprised of current chemistries such as MOE, ANA, FANA, PS etc (Uhlman, et al. (2000) Current Opinions in Drug Discovery & Development Vol. 3 No 2). This can be achieved by substituting some of the monomers in the current oligonucleotides by LNA monomers. The LNA modified oligonucleotide may have a size similar to the parent compound or may be larger or preferably smaller. It is preferred that such LNA-modified oligonucleotides contain less than about 70%, more preferably less than about 60%, most preferably less than about 50% LNA monomers and that their sizes are between about 5 and 25 nucleotides, more preferably between about 12 and 20 nucleotides.

Preferred modified oligonucleotide backbones comprise, but not limited to, phosphorothioates, chiral phosphorothioates, phosphorodithioates, phosphotriesters, aminoalkylphosphotriesters, methyl and other alkyl phosphonates comprising 3' alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus containing linkages comprise, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

Representative United States patents that teach the preparation of the above oligonucleosides comprise, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen, et al. (1991) Science 254, 1497-1500.

In another preferred embodiment of the invention the oligonucleotides with phosphorothioate backbones and oligonucleosides with heteroatom backbones, and in particular —CH2—NH—O—CH2—, —CH2—N(CH3)—O—CH2- known as a methylene (methylimino) or MMI backbone, —CH2—O—N(CH3)—CH2—, —CH2N(CH3)—N(CH3) CH2— and —O—N(CH3)—CH2—CH2— wherein the native phosphodiester backbone is represented as —O—P—O—CH2— of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O alkyl-O-alkyl, wherein the alkyl, alkenyl and alkynyl may be substituted or unsubstituted C to CO alkyl or C2 to CO alkenyl and alkynyl. Particularly preferred are O(CH2)nOmCH3, O(CH2)n, OCH3, O(CH2)nNH2, O(CH2)nCH3, O(CH2)nONH2, and O(CH2nON(CH2) nCH3)2 where n and m can be from 1 to about 10. Other preferred oligonucleotides comprise one of the following at the 2' position: C to CO, (lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification comprises 2'-methoxyethoxy (2'-O—CH2CH2OCH3, also known as 2'-O-(2-methoxyethyl) or 2'-MOE) (Martin et al., (1995) Hely. Chim. Acta, 78, 486-504) i.e., an alkoxyalkoxy group. A further preferred modification comprises 2'-dimethylaminooxyethoxy, i.e., a O(CH2)2ON(CH3)2 group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH2—O—CH2—N (CH2)2.

Other preferred modifications comprise 2'-methoxy (2'-OCH3), 2'-aminopropoxy (2'-OCH2CH2CH2NH2) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures comprise, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference.

Oligonucleotides may also comprise nucleobase (often referred to in the art simply as "base") modifications or substitutions. As used herein, "unmodified" or "natural" nucleotides comprise the purine bases adenine (A) and guanine (G), and the pyrimidine bases thymine (T), cytosine (C) and uracil (U). Modified nucleotides comprise other synthetic and natural nucleotides such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleotides comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., 'Angewandle Chemie, International Edition', 1991, 30, page 613, and those disclosed by Sanghvi, Y. S., Chapter 15, 'Antisense Research and Applications', pages 289-302, Crooke, S. T. and Lebleu, B. ea., CRC Press, 1993. Certain of these nucleotides are particularly useful for increasing the binding affinity of the oligomeric compounds of the invention. These comprise 5-substituted pyrimidines, 6-azapyrimidines and N2, N-6 and O-6 substituted purines, comprising 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-Omethoxyethyl sugar modifications.

Representative United States patents that teach the preparation of the above noted modified nucleotides as well as other modified nucleotides comprise, but are not limited to, U.S. Pat. Nos. 3,687,808, 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

Another modification of the oligonucleotides of the invention involves chemically linking to the oligonucleotide one or more moieties or conjugates, which enhance the activity, cellular distribution, or cellular uptake of the oligonucleotide.

Such moieties comprise but are not limited to, lipid moieties such as a cholesterol moiety (Letsinger et al., (1989) Proc. Natl. Acad. Sci. USA, 86, 6553-6556), cholic acid (Manoharan et al., (1994) Bioorg. Med. Chem. Let., 4, 1053-1060), a thioether, e.g., hexyl-S-tritylthiol (Manoharan et al., (1992) Ann. N.Y. Acad. Sci., 660, 306-309; Manoharan et al., (1993) Bioorg. Med. Chem. Let., 3, 2765-2770), a thiocholesterol (Oberhauser et al., (1992) Nucl. Acids Res., 20, 533-538), an aliphatic chain, e.g., dodecandiol or undecyl residues (Kabanov et al., (1990) FEBS Lett., 259, 327-330; Svinarchuk et al., (1993) Biochimie 75, 49-54), a phospholipid, e.g., di-hexadecyl-rac-glycerol or triethylammonium 1,2-di-O-hexadecyl-rac-glycero-3-H-phosphonate (Manoharan et al., (1995) Tetrahedron Lett., 36, 3651-3654; Shea et al., (1990) Nucl. Acids Res., 18, 3777-3783), a polyamine or a polyethylene glycol chain (Mancharan et al., (1995) Nucleosides & Nucleotides, 14, 969-973), or adamantane acetic acid (Manoharan et al., (1995) Tetrahedron Lett., 36, 3651-3654), a palmityl moiety (Mishra et al., (1995) Biochim. Biophys. Acta, 1264, 229-237), or an octadecylamine or hexylamino-carbonyl-t oxycholesterol moiety (Crooke et al., (1996) J. Pharmacol. Exp. Ther., 277, 923-937).

Representative United States patents that teach the preparation of such oligonucleotides conjugates comprise, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

Drug discovery: The compounds of the present invention can also be applied in the areas of drug discovery and target validation. The present invention comprehends the use of the compounds and preferred target segments identified herein in drug discovery efforts to elucidate relationships that exist between Brain derived neurotrophic factor (BDNF) polynucleotides and a disease state, phenotype, or condition. These methods include detecting or modulating Brain derived neurotrophic factor (BDNF) polynucleotides comprising contacting a sample, tissue, cell, or organism with the compounds of the present invention, measuring the nucleic acid or protein level of Brain derived neurotrophic factor (BDNF) polynucleotides and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

Assessing Up-Regulation or Inhibition of Gene Expression:

Transfer of an exogenous nucleic acid into a host cell or organism can be assessed by directly detecting the presence of the nucleic acid in the cell or organism. Such detection can be achieved by several methods well known in the art. For example, the presence of the exogenous nucleic acid can be detected by Southern blot or by a polymerase chain reaction (PCR) technique using primers that specifically amplify nucleotide sequences associated with the nucleic acid. Expression of the exogenous nucleic acids can also be measured using conventional methods including gene expression analysis. For instance, mRNA produced from an exogenous nucleic acid can be detected and quantified using a Northern blot and reverse transcription PCR (RT-PCR).

Expression of RNA from the exogenous nucleic acid can also be detected by measuring an enzymatic activity or a reporter protein activity. For example, antisense modulatory activity can be measured indirectly as a decrease or increase in target nucleic acid expression as an indication that the exogenous nucleic acid is producing the effector RNA. Based on sequence conservation, primers can be designed and used to amplify coding regions of the target genes. Initially, the most highly expressed coding region from each gene can be used to build a model control gene, although any coding or non coding region can be used. Each control gene is assembled by inserting each coding region between a reporter coding region and its poly(A) signal. These plasmids would produce an mRNA with a reporter gene in the upstream portion of the gene and a potential RNAi target in the 3' non-coding region. The effectiveness of individual antisense oligonucleotides would be assayed by modulation of the reporter gene. Reporter genes useful in the methods of the present invention include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline. Methods to determine modulation of a reporter gene are well known in the art, and include, but are not limited to, fluorometric methods (e.g. fluorescence spectroscopy, Fluorescence Activated Cell Sorting (FACS), fluorescence microscopy), antibiotic resistance determination.

BDNF protein and mRNA expression can be assayed using methods known to those of skill in the art and described elsewhere herein. For example, immunoassays such as the ELISA can be used to measure protein levels. BDNF ELISA kits are available commercially, e.g., from R&D Systems (Minneapolis, Minn.).

In embodiments, BDNF expression (e.g., mRNA or protein) in a sample (e.g., cells or tissues in vivo or in vitro) treated using an antisense oligonucleotide of the invention is evaluated by comparison with BDNF expression in a control sample. For example, expression of the protein or nucleic acid can be compared using methods known to those of skill in the art with that in a mock-treated or untreated sample. Alternatively, comparison with a sample treated with a control antisense oligonucleotide (e.g., one having an altered or different sequence) can be made depending on the information desired. In another embodiment, a difference in the expression of the BDNF protein or nucleic acid in a treated vs an untreated sample can be compared with the difference in expression of a different nucleic acid (including any standard deemed appropriate by the researcher, e.g., a housekeeping gene) in a treated sample vs an untreated sample.

Observed differences can be expressed as desired, e.g., in the form of a ratio or fraction, for use in a comparison with control. In embodiments, the level of BDNF mRNA or protein, in a sample treated with an antisense oligonucleotide of the present invention, is increased or decreased by about 1.25-fold to about 10-fold or more relative to an untreated sample or a sample treated with a control nucleic acid. In embodiments, the level of BDNF mRNA or protein is increased or decreased by at least about 1.25-fold, at least about 1.3-fold, at least about 1.4-fold, at least about 1.5-fold, at least about 1.6-fold, at least about 1.7-fold, at least about 1.8-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, or at least about 10-fold or more.

Kits, Research Reagents, Diagnostics, and Therapeutics

The compounds of the present invention can be utilized for diagnostics, therapeutics, and prophylaxis, and as research reagents and components of kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics and in various biological systems, the compounds of the present invention, either alone or in combination with other compounds or therapeutics, are useful as tools in differential and/or combinatorial analyses to elucidate expression patterns of a portion or the entire complement of genes expressed within cells and tissues.

As used herein the term "biological system" or "system" is defined as any organism, cell, cell culture or tissue that expresses, or is made competent to express products of the Brain derived neurotrophic factor (BDNF) genes. These include, but are not limited to, humans, transgenic animals, cells, cell cultures, tissues, xenografts, transplants and combinations thereof As one non limiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds that affect expression patterns.

Examples of methods of gene expression analysis known in the art include DNA arrays or microarrays (Brazma and Vilo, (2000) FEBS Lett., 480, 17-24; Celis, et al., (2000) FEBS Lett., 480, 2-16), SAGE (serial analysis of gene expression) (Madden, et al., (2000) Drug Discov. Today, 5, 415-425), READS (restriction enzyme amplification of digested cDNAs) (Prashar and Weissman, (1999) Methods Enzymol., 303, 258-72), TOGA (total gene expression analysis) (Sutcliffe, et al., (2000) Proc. Natl. Acad. Sci. U.S.A., 97, 1976-81), protein arrays and proteomics (Celis, et al., (2000) FEBS Lett., 480, 2-16; Jungblut, et al., Electrophoresis, 1999, 20, 2100-10), expressed sequence tag (EST) sequencing (Celis, et al., FEBS Lett., 2000, 480, 2-16; Larsson, et al., J. Biotechnol., 2000, 80, 143-57), subtractive RNA fingerprinting (SuRF) (Fuchs, et al., (2000) Anal. Biochem. 286, 91-98; Larson, et al., (2000) Cytometry 41, 203-208), subtractive cloning, differential display (DD) (Jurecic and Belmont, (2000) Curr. Opin. Microbiol. 3, 316-21), comparative genomic hybridization (Carulli, et al., (1998) J. Cell Biochem. Suppl., 31, 286-96), FISH (fluorescent in situ hybridization) techniques (Going and Gusterson, (1999) Eur. J. Cancer, 35, 1895-904) and mass spectrometry methods (To, Comb. (2000) Chem. High Throughput Screen, 3, 235-41).

The compounds of the invention are useful for research and diagnostics, because these compounds hybridize to nucleic acids encoding Brain derived neurotrophic factor (BDNF). For example, oligonucleotides that hybridize with such efficiency and under such conditions as disclosed herein as to be effective Brain derived neurotrophic factor (BDNF) modulators are effective primers or probes under conditions favoring gene amplification or detection, respectively. These primers and probes are useful in methods requiring the specific detection of nucleic acid molecules encoding Brain derived neurotrophic factor (BDNF) and in the amplification of said nucleic acid molecules for detection or for use in further studies of Brain derived neurotrophic factor (BDNF). Hybridization of the antisense oligonucleotides, particularly the primers and probes, of the invention with a nucleic acid encoding Brain derived neurotrophic factor (BDNF) can be detected by means known in the art. Such means may include conjugation of an enzyme to the oligonucleotide, radiolabeling of the oligonucleotide, or any other suitable detection means. Kits using such detection means for detecting the level of Brain derived neurotrophic factor (BDNF) in a sample may also be prepared.

The specificity and sensitivity of antisense are also harnessed by those of skill in the art for therapeutic uses. Antisense compounds have been employed as therapeutic moieties in the treatment of disease states in animals, including humans. Antisense oligonucleotide drugs have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of Brain derived neurotrophic factor (BDNF) polynucleotides is treated by administering antisense compounds in accordance with this invention. For example, in one non-limiting embodiment, the methods comprise the step of administering to the animal in need of treatment, a therapeutically effective amount of Brain derived neurotrophic factor (BDNF) modulator. The Brain derived neurotrophic factor (BDNF) modulators of the present invention effectively modulate the activity of the Brain derived neurotrophic factor (BDNF) or modulate the expression of the Brain derived neurotrophic factor (BDNF) protein. In one embodiment, the activity or expression of Brain derived neurotrophic factor (BDNF) in an animal is inhibited by about 10% as compared to a control. Preferably, the activity or expression of Brain derived neurotrophic factor (BDNF) in an animal is inhibited by about 30%. More preferably, the activity or expression of Brain derived neurotrophic factor (BDNF) in an animal is inhibited by 50% or more. Thus, the oligomeric compounds modulate expression of Brain derived neurotrophic factor (BDNF) mRNA by at least 10%, by at least 50%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100% as compared to a control.

In one embodiment, the activity or expression of Brain derived neurotrophic factor (BDNF) and/or in an animal is increased by about 10% as compared to a control. Preferably, the activity or expression of Brain derived neurotrophic factor (BDNF) in an animal is increased by about 30%. More preferably, the activity or expression of Brain derived neurotrophic factor (BDNF) in an animal is increased by 50% or more. Thus, the oligomeric compounds modulate expression of Brain derived neurotrophic factor (BDNF) mRNA by at least 10%, by at least 50%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100% as compared to a control.

For example, the reduction of the expression of Brain derived neurotrophic factor (BDNF) may be measured in serum, blood, adipose tissue, liver or any other body fluid, tissue or organ of the animal. Preferably, the cells contained within said fluids, tissues or organs being analyzed contain a nucleic acid molecule encoding Brain derived neurotrophic factor (BDNF) peptides and/or the Brain derived neurotrophic factor (BDNF) protein itself The compounds of the invention can be utilized in pharmaceutical compositions by adding an effective amount of a compound to a suitable pharmaceutically acceptable diluent or carrier. Use of the compounds and methods of the invention may also be useful prophylactically.

Conjugates

Another modification of the oligonucleotides of the invention involves chemically linking to the oligonucleotide one or more moieties or conjugates that enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-Hphosphonate, a polyamine or a polyethylene glycol chain, or adamantane acetic acid, a palmityl moiety, or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

Representative United States patents that teach the preparation of such oligonucleotides conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,165; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Although, the antisense oligonucleotides do not need to be administered in the context of a vector in order to modulate a target expression and/or function, embodiments of the invention relates to expression vector constructs for the expression of antisense oligonucleotides, comprising promoters, hybrid promoter gene sequences and possess a strong constitutive promoter activity, or a promoter activity which can be induced in the desired case.

In an embodiment, invention practice involves administering at least one of the foregoing antisense oligonucleotides with a suitable nucleic acid delivery system. In one embodiment, that system includes a non-viral vector operably linked to the polynucleotide. Examples of such nonviral vectors include the oligonucleotide alone (e.g. any one or more of SEQ ID NOS: 3 to 8) or in combination with a suitable protein, polysaccharide or lipid formulation.

Additionally suitable nucleic acid delivery systems include viral vector, typically sequence from at least one of an adenovirus, adenovirus-associated virus (AAV), helper-dependent adenovirus, retrovirus, or hemagglutinatin virus of Japan-liposome (HVJ) complex. Preferably, the viral vector comprises a strong eukaryotic promoter operably linked to the polynucleotide e.g., a cytomegalovirus (CMV) promoter.

Additionally preferred vectors include viral vectors, fusion proteins and chemical conjugates. Retroviral vectors include Moloney murine leukemia viruses and HIV-based viruses. One preferred HIV-based viral vector comprises at least two vectors wherein the gag and pol genes are from an HIV genome and the env gene is from another virus. DNA viral vectors are preferred. These vectors include pox vectors such as orthopox or avipox vectors, herpesvirus vectors such as a herpes simplex I virus (HSV) vector [Geller, A. I. et al., (1995) J. Neurochem, 64: 487; Lim, F., et al., in DNA Cloning: Mammalian Systems, D. Glover, Ed. (Oxford Univ. Press, Oxford England) (1995); Geller, A. I. et al., (1993) Proc Natl. Acad. Sci.: U.S.A.:90 7603; Geller, A. I., et al., (1990) Proc Natl. Acad. Sci. USA: 87:1149], Adenovirus Vectors (LeGal LaSalle et al., Science, 259:988 (1993); Davidson, et al., (1993) Nat. Genet. 3: 219; Yang, et al., (1995) J. Virol. 69: 2004) and Adeno-associated Virus Vectors (Kaplitt, M. G., et al., (1994) Nat. Genet. 8:148).

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein by reference.

The present invention also includes pharmaceutical compositions and formulations that include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

For treating tissues in the central nervous system, administration can be made by, e.g., injection or infusion into the cerebrospinal fluid. Administration of antisense RNA into cerebrospinal fluid is described, e.g., in U.S. Pat. App. Pub. No. 2007/0117772, "Methods for slowing familial ALS disease progression," incorporated herein by reference in its entirety.

When it is intended that the antisense oligonucleotide of the present invention be administered to cells in the central nervous system, administration can be with one or more agents capable of promoting penetration of the subject antisense oligonucleotide across the blood-brain barrier. Injection can be made, e.g., in the entorhinal cortex or hippocampus. Delivery of neurotrophic factors by administration of an adenovirus vector to motor neurons in muscle tissue is described in, e.g., U.S. Pat. No. 6,632,427, "Adenoviral-vector-mediated gene transfer into medullary motor neurons," incorporated herein by reference. Delivery of vectors directly to the brain, e.g., the striatum, the thalamus, the hippocampus, or the substantia nigra, is known in the art and described, e.g., in U.S. Pat. No. 6,756,523, "Adenovirus vectors for the transfer of foreign genes into cells of the central nervous system particularly in brain," incorporated herein by reference. Administration can be rapid as by injection or made over a period of time as by slow infusion or administration of slow release formulations. The subject antisense oligonucleotides can also be linked or conjugated with agents that provide desirable pharmaceutical or pharmacodynamic properties. For example, the antisense oligonucleotide can be coupled to any substance, known in the art to promote penetration or transport across the blood-brain barrier, such as an antibody to the transferrin receptor, and administered by intravenous injection. The antisense compound can be linked with a viral vector, for example, that makes the antisense compound more effective and/or increases the transport of the antisense compound across the blood-brain barrier. Osmotic blood brain barrier disruption can also be accomplished by, e.g., infusion of sugars including, but not limited to, meso erythritol, xylitol, D(+) galactose, D(+) lactose, D(+) xylose, dulcitol, myo-inositol, L(−) fructose, D(−) mannitol, D(+) glucose, D(+) arabinose, D(−) arabinose, cellobiose, D(+) maltose, D(+) raffinose, L(+) rhamnose, D(+) melibiose, D(−) ribose, adonitol, D(+) arabitol, L(−) arabitol, D(+) fucose, L(−) fucose, D(−) lyxose, L(+) lyxose, and L(−) lyxose, or amino acids including, but not limited to, glutamine, lysine, arginine, asparagine, aspartic acid, cysteine, glutamic acid, glycine, histidine, leucine, methionine, phenylalanine, proline, serine, threonine, tyrosine, valine, and taurine. Methods and materials for enhancing blood brain barrier penetration are described, e.g., in U.S. Pat. No. 4,866,042, "Method for the delivery of genetic material across the blood brain barrier," U.S. Pat. No. 6,294,520, "Material for passage through the blood-brain barrier," and U.S. Pat. No. 6,936,589, "Parenteral delivery systems," all incorporated herein by reference in their entirety.

The subject antisense compounds may be admixed, encapsulated, conjugated or otherwise associated with other molecules, molecule structures or mixtures of compounds, for example, liposomes, receptor-targeted molecules, oral, rectal, topical or other formulations, for assisting in uptake, distribution and/or absorption. For example, cationic lipids may be included in the formulation to facilitate oligonucleotide uptake. One such composition shown to facilitate uptake is LIPOFECTIN (available from GIBCO-BRL, Bethesda, Md.).

Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogeneous systems of one liquid dispersed in another in the form of droplets usually exceeding 0.1 .mu.m in diameter. Emulsions may contain additional components in addition to the dispersed phases, and the active drug that may be present as a solution in either the aqueous phase, oily phase or itself as a separate phase. Microemulsions are included as an embodiment of the present invention. Emulsions and their uses are well known in the art and are further described in U.S. Pat. No. 6,287,860.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids. When incorporated into liposomes, these specialized lipids result in liposomes with enhanced circulation lifetimes relative to liposomeslacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein by reference.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating nonsurfactants. Penetration enhancers and their uses are further described in U.S. Pat. No. 6,287,860, which is incorporated herein by reference.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoyl-phosphatidyl DOPE ethanolamine, dimyristoylphosphatidyl choline DMPC, distearolyphosphatidyl choline) negative (e.g. dimyristoylphosphatidyl glycerol DMPG) and cationic (e.g.

dioleoyltetramethylaminopropyl DOTAP and dioleoyl-phosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof, and their uses are further described in U.S. Pat. No. 6,287,860.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein by reference. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein by reference.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligomeric compounds and one or more other chemotherapeutic agents that function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bischloroethyl-nitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclo-phosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. For example, the first target may be a particular antisense sequence of Brain derived neurotrophic factor (BDNF), and the second target may be a region from another nucleotide sequence. Alternatively, compositions of the invention may contain two or more antisense compounds targeted to different regions of the same Brain derived neurotrophic factor (BDNF) nucleic acid target. Numerous examples of antisense compounds are illustrated herein and others may be selected from among suitable compounds known in the art. Two or more combined compounds may be used together or sequentially.

Dosing:

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on EC50s found to be effective in in vitro and in vivo animal models. In general, dosage is from 0.01 .mu.g to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 .mu.g to 100 g per kg of body weight, once or more daily, to once every 20 years. In embodiments, a patient is treated with a dosage of drug that is at least about 1, at least about 2, at least about 3, at least about 4, at least about 5, at least about 6, at least about 7, at least about 8, at least about 9, at least about 10, at least about 15, at least about 20, at least about 25, at least about 30, at least about 35, at least about 40, at least about 45, at least about 50, at least about 60, at least about 70, at least about 80, at least about 90, or at least about 100 mg/kg body weight. Certain injected dosages of antisense oligonucleotides are described, e.g., in U.S. Pat. No. 7,563,884, "Antisense modulation of PTP1B expression," incorporated herein by reference in its entirety.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention. Embodiments of inventive compositions and methods are illustrated in the following examples.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

Example 1: Design of Antisense Oligonucleotides Specific for a Nucleic Acid Molecule Antisense to a Brain Derived Neurotrophic Factor (BDNF) Polynucleotide and/or a Sense Strand of Brain Derived Neurotrophic Factor (BDNF) Polynucleotide As indicated above the term "oligonucleotide specific for" or "oligonucleotide targets" refers to an oligonucleotide having a sequence (i) capable of forming a stable complex with a portion of the targeted gene, or (ii) capable of forming a stable duplex with a portion of an mRNA transcript of the targeted gene.

Selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of oligonucleotides that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

An antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays The hybridization properties of the oligonucleotides described herein can be determined by one or more in vitro assays as known in the art. For example, the properties of the oligonucleotides described herein can be obtained by determination of binding strength between the target natural antisense and a potential drug molecules using melting curve assay.

The binding strength between the target natural antisense and a potential drug molecule (Molecule) can be estimated using any of the established methods of measuring the strength of intermolecular interactions, for example, a melting curve assay.

Melting curve assay determines the temperature at which a rapid transition from double-stranded to single-stranded conformation occurs for the natural antisense/Molecule complex. This temperature is widely accepted as a reliable measure of the interaction strength between the two molecules.

A melting curve assay can be performed using a cDNA copy of the actual natural antisense RNA molecule or a synthetic DNA or RNA nucleotide corresponding to the binding site of the Molecule. Multiple kits containing all necessary reagents to perform this assay are available (e.g. Applied Biosystems Inc. MeltDoctor kit). These kits include a suitable buffer solution containing one of the double strand DNA (dsDNA) binding dyes (such as ABI HRM dyes, SYBR Green, SYTO, etc.). The properties of the dsDNA dyes are such that they emit almost no fluorescence in free form, but are highly fluorescent when bound to dsDNA.

To perform the assay the cDNA or a corresponding oligonucleotide are mixed with Molecule in concentrations defined by the particular manufacturer's protocols. The mixture is heated to 95° C. to dissociate all pre-formed dsDNA complexes, then slowly cooled to room temperature or other lower temperature defined by the kit manufacturer to allow the DNA molecules to anneal. The newly formed complexes are then slowly heated to 95° C. with simultaneous continuous collection of data on the amount of fluorescence that is produced by the reaction. The fluorescence intensity is inversely proportional to the amounts of dsDNA present in the reaction. The data can be collected using a real time PCR instrument compatible with the kit (e.g. ABI's StepOne Plus Real Time PCR System or LightTyper instrument, Roche Diagnostics, Lewes, UK).

Melting peaks are constructed by plotting the negative derivative of fluorescence with respect to temperature (-d (Fluorescence)/dT) on the y-axis) against temperature (x-axis) using appropriate software (for example LightTyper (Roche) or SDS Dissociation Curve, ABI). The data is analyzed to identify the temperature of the rapid transition from dsDNA complex to single strand molecules. This temperature is called Tm and is directly proportional to the strength of interaction between the two molecules. Typically, Tm will exceed 40° C.

Example 2

Modulation of BDNF Polynucleotides

Treatment of HepG2 Cells with Antisense Oligonucleotides:

HepG2 cells from ATCC (cat #HB-8065) were grown in growth media (MEM/EBSS (Hyclone cat #SH30024, or Mediatech cat #MT-10-010-CV)+10% FBS (Mediatech cat #MT35-011-CV)+penicillin/streptomycin (Mediatech cat #MT30-002-CI)) at 37° C. and 5% $CO_2$. One day before the experiment the cells were replated at the density of 1.5.times.10.sup.5/ml into 6 well plates and incubated at 37° C. and 5% $CO_2$. On the day of the experiment the media in the 6 well plates was changed to fresh growth media. All antisense oligonucleotides were diluted to the concentration of 20 .mu.M. Two .mu.l of this solution was incubated with 400 .mu.l of Opti-MEM media (Gibco cat #31985-070) and 4 .mu.l of Lipofectamine 2000 (Invitrogen cat #11668019) at room temperature for 20 min and applied to each well of the 6 well plates with HepG2 cells. A Similar mixture including 2 .mu.l of water instead of the oligonucleotide solution was used for the mock-transfected controls. After 3-18 h of incubation at 37° C. and 5% $CO_2$ the media was changed to fresh growth media. 48 h after addition of antisense oligonucleotides the media was removed and RNA was extracted from the cells using SV Total RNA Isolation System from Promega (cat #Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat #AB1453B) or High Capacity cDNA Reverse Transcription Kit (cat #4368813) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Taqman Gene Expression Assay by Applied Biosystems Inc., Foster City Calif.). The following PCR cycle was used: 50° C. for 2 min, 95° C. for 10 min, 40 cycles of (95° C. for 15 seconds, 60° C. for 1 min) using StepOne Plus Real Time PCR Machine (Applied Biosystems).

Fold change in gene expression after treatment with antisense oligonucleotides was calculated based on the difference in 18S-normalized dCt values between treated and mock-transfected samples.

Detection Oligos for BDNF Antisense:

```
ABI assay ID His00417345_m1
                                        (SEQ ID No.: 9)
Context sequence
GCACACCTGGAGATACTCTATTATA
```

Detection Oligos for BDNF:

```
ABI assay ID Hs00542425_s1
                                        (SEQ ID No.: 10)
CCTGCAGAATGGCCTGGAATTACAA
```

Figure 1B:
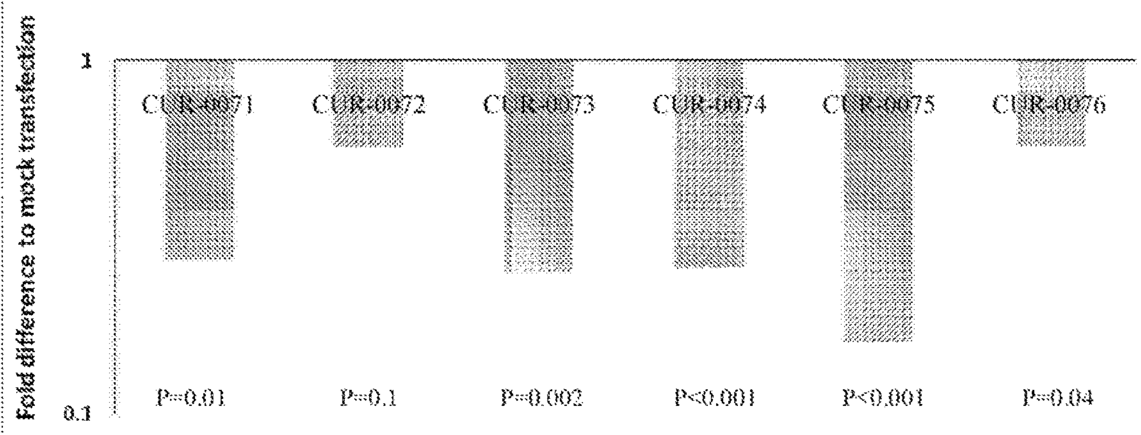
FIG. 1B: is a graph of real time PCR results showing the fold change+standard deviation in BDNF mRNA after treatment of HepG2 cells with phosphorothioate oligonucleotides introduced using Lipofectamine 2000, as compared to control. Real time PCR results show that the levels of BDNF antisense were significantly decreased after treatment with all oligos except CUR-0072, which is possibly due to different oligos affecting different splice variants of BDNF and/or BDNF antisense NM_170735. Bars denoted as CUR-0071, CUR-0072, CUR-0073, CUR-0074, CUR-0075 and CUR-0076 correspond to samples treated with SEQ ID NOS: 6, 7, 8, 5, 4 and 3, respectively.

Results:

Real time PCR results show that the levels of the BDNF mRNA in HepG2 cells are significantly increased 48 h after treatment with two of the LNA gapmers with fully phosphothioated backbone designed to BDNF antisense (CUR-71, P=0.04, CUR-73, P=0.07, CUR-76, P=0.03) (FIG. 1A). In the same samples the levels of BDNF antisense were significantly decreased after treatment with all oligos except CUR-72, which is possibly due to different oligos affecting different splice variants of BDNF and/or BDNF antisense (FIG. 1B).

Treatment of CHP212 Cells with Antisense Oligonucleotides:

CHP212 cells from ATCC (cat #CRL-2273) were grown in growth media (MEM/F12 (ATCC cat #30-2003 and Mediatech cat #10-080-CV)+10% FBS (Mediatech cat #MT35-011-CV)+penicillin/streptomycin (Mediatech cat #MT30-002-CI)) at 37° C. and 5% $CO_2$. One day before the experiment the cells were replated at the density of 1.5.times.10.sup.5/m1 into 6 well plates and incubated at 37° C. and 5% $CO_2$. On the day of the experiment the media in the 6 well plates was changed to fresh growth media. All antisense oligonucleotides were diluted to the concentration of 20 .mu.M. Two .mu.l of this solution was incubated with 400 .mu.l of Opti-MEM media (Gibco cat #31985-070) and 4 .mu.l of Lipofectamine 2000 (Invitrogen cat #11668019) at room temperature for 20 min and applied to each well of the 6 well plates with CHP212 cells. Similar mixture including 2 .mu.l of water instead of the oligonucleotide solution was used for the mock-transfected controls. After 3-18 h of incubation at 37° C. and 5% $CO_2$ the media was changed to fresh growth media. 48 h after addition of antisense oligonucleotides the media was removed and RNA was extracted from the cells using SV Total RNA Isolation System from Promega (cat #Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat #AB1453B) or High Capacity cDNA Reverse Transcription Kit (cat #4368813) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Taqman Gene Expression Assay: Hs00542425_s1 by Applied Biosystems Inc., Foster City Calif.). The following PCR cycle was used: 50° C. for 2 min, 95° C. for 10 min, 40 cycles of (95° C. for 15 seconds, 60° C. for 1 min) using StepOne Plus Real Time PCR Machine (Applied Biosystems).

Fold change in gene expression after treatment with antisense oligonucleotides was calculated based on the difference in 18S-normalized dCt values between treated and mock-transfected samples.

Figure 1C:
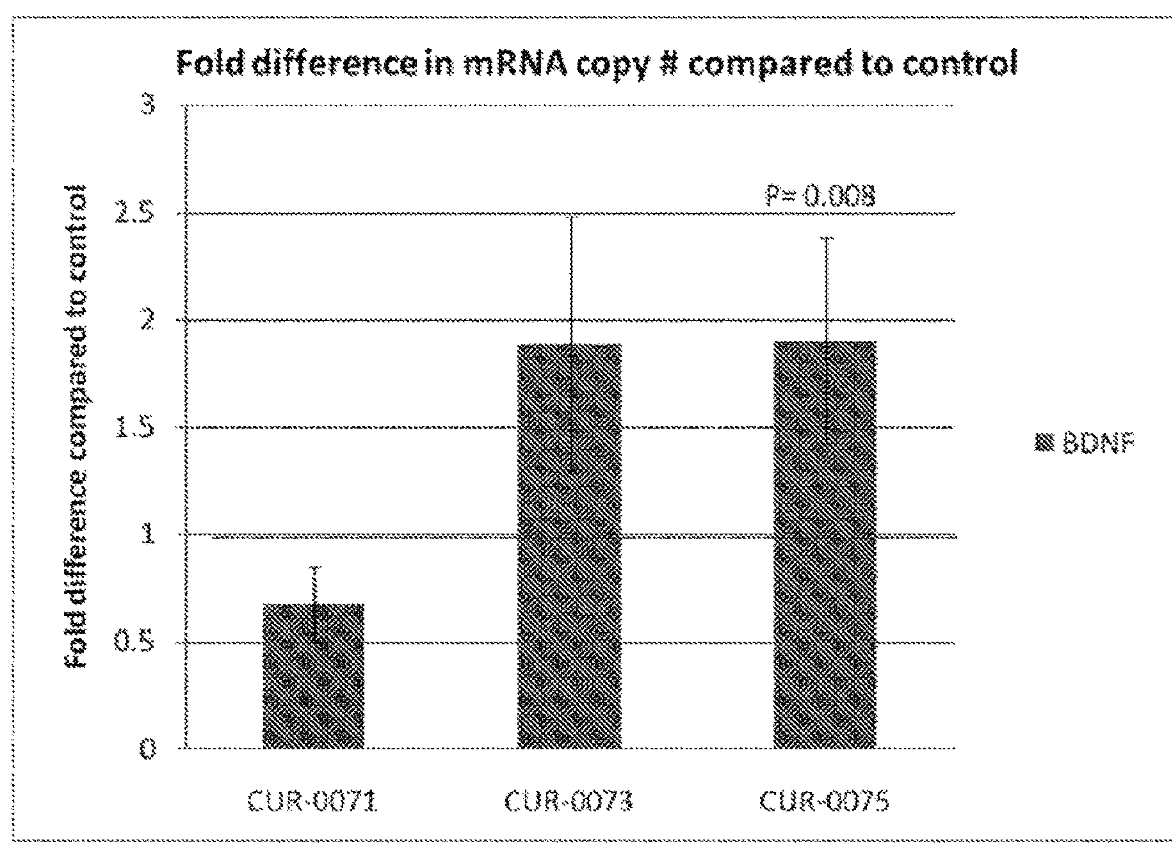
FIG. 1C: is a graph of real time PCR results showing the fold change+standard deviation in BDNF mRNA after treatment of CHP212 cells with LNA gapmer-phosphorothioate oligonucleotides introduced using Lipofectamine 2000, as compared to control. Real time PCR results show that the levels of the BDNF mRNA in CHP212 cells are significantly increased 48 h after treatment with two of the LNA gapmers with fully phosphothioated backbone designed to BDNF antisense NM_4170735. Bars denoted as CUR-0071, CUR-0073, and CUR-0075 correspond to samples treated with SEQ ID NOS: 6, 8, and 4, respectively.

Results:

Real time PCR results show that the levels of the BDNF mRNA in CHP212 cells are significantly increased 48 h after treatment with three of the oligos designed to BDNF antisense (FIG. 1*c*).

Example 3: Antisense Modulation of BDNF Polynucleotide and Protein Product and Effect on Memory and Learning in Amyloid-Transgenic Mice Antisense oligonucleotides specific for BDNF-AS (e.g., oligonucleotides identified by SEQ ID NOS 3-8) are administered to J20 mice, which express the human amyloid precursor protein (APP) transgene bearing both the Swedish and Indiana APP mutations. As described by, e.g., Nagahara, et al., 2009, "Neuroprotective effects of brain-derived neurotrophic factor in rodent and primate models of Alzheimer's disease," Nature Medicine 15(3): 331-337, incorporated herein by reference, these mice show cortical plaques and progressive cell loss in the entorhinal cortex beginning at age 2-3 months, and cognitive decline by 6-7 months. Pre-treatment blood samples are collected several days before dosing by collecting 4-7 drops from the tail vein. Each antisense oligonucleotide is dissolved in PBS and administered into a mouse by injection into the entorhinal cortex or the hippocampus at about 10 mg/kg. Control mice (age-matched WT littermates) are administered the same volume of PBS alone. One month later, spatial memory is tested in the Morris water maze in treated and control mice, and their performance compared. Restorative effects are also tested by measuring hippocampal-dependent and hippocampal-independent learning. After testing, the mice are sacrificed and brain tissues (entorhinal cortex and hippocampal dentate gyms) are collected for analysis of expression of BDNF protein and mRNA. Human BDNF protein concentration and secretion levels are determined using an enzyme linked immunosorbent assay (ELISA) kit (available commercially, e.g., Quantikine human BDNF, R&D Systems, Minneapolis, Minn.), according to the manufacturer's instructions. mRNA is assayed using RT-PCR, as described elsewhere herein.

Example 4: Antisense Modulation of BDNF Polynucleotide and Protein Product and Effect on Memory and Learning in SAM-P8 Mice The P8 strain of senescence accelerated mice (SAM), as described, e.g., in U.S. Pat. No. 6,310,048, "Antisense modulation of amyloid beta protein expression," incorporated herein by reference, show an age-related increase in impaired learning (acquisition) and memory (retention) as well as an age-related increase in the accumulation of amyloid precursor protein and A.beta.P. SAM-P8 mice have a median life span of 17.2 months, as opposed to a normal life span of 24 months for standard R1 mice.

SAM-P8 mice are divided into seven groups of 10 mice each. At 11 months of age (4 weeks prior to training) one group is given 0.2 microliters of calf serum by intracerebral ventricular injection (ICV), while the other six groups are given one or two 0.2 microliter injections (each of 2 microliters and having 60 ng of oligonucleotide) ICV of antisense oligonucleotides of the present invention. Administration is performed by drilling a hole through the skull over the third ventricle (−0.5 relative to bregma; 0.5 mm right of central suture). The scalp is closed and the mice are returned to their cages. Two weeks after this first injection, one of the groups of treated mice and the group that had received serum are injected with the saline vehicle that is used as the carrier for the antisense oligonucleotides. At this same time (two weeks before training), each one of the oligonucleotides is administered in saline ICV to all of the mice in one group. Each administration contains 0.2 microliter (60 ng of oligonucleotide per injection).

Two weeks after the last injection, when the mice are 12 months of age, they are trained on footshock avoidance in a T-maze. The training and testing procedures are the same as described by Flood et al., Physiology & Behavior, 58:819-822 (1995); and Flood et al., Neurobiology of Aging, 14:159-166 (1993), and U.S. Pat. No. 6,310,048, all incorporated by reference herein. All mice are trained until they make their first avoidance response. Retention test scores when tested 1 hr after training and one week later are compared. One week after original training, retention for both 4 and 12 month-old mice is tested by continuing the training until each mouse makes 5 avoidances in 6 consecutive training trials. Results are expressed as means and with a standard error of the means. The trials to first avoidance, or to a criterion of 5 avoidances in 6 consecutive trials are analyzed in separate one way ANOVAs. Statistical differences between the means of the 12 month-old mice that received antisense oligonucleotides are compared to the means of the 12 month-old mice that received the saline solution vehicle using Dunnett's T-test.

Samples are recovered from the amygdala, hippocampal, and septum regions of the brains of each of four mice, two treated with the saline vehicle and the other two treated with the antisense oligonucleotides. The samples are tested for BDNF protein expression by ELISA or immuno-blotting against an antibody that specifically hybridizes to BDNF.

Example 5: Antisense Modulation of BDNF Polynucleotide and Protein Product and Effect on Disease Progression in Patients with Amyotrophic Lateral Sclerosis A pharmaceutical composition comprising an antisense oligonucleotide of the present invention (e.g., an oligonucleotide identified by any of SEQ ID NOS: 3-8) is administered to the cerebrospinal fluid of an individual suffering from familial ALS. A Medtronic SyncroMed II pump is used to deliver the composition to the cerebrospinal fluid. The pump is surgically implanted according to the manufacturer instructions. The pump reservoir is loaded with the pharmaceutical composition in phosphate-buffered saline. The pharmaceutical composition is administered at an amount that yields an infusion of 8 mg to 12 mg/day of the antisense oligonucleotide into the cerebrospinal fluid. Antisense oligonucleotide is infused, for at least 28 days. The drug is pumped at a programmed dose into a catheter that is surgically intrathecally implanted.

Disease progression is measured by methods routine in the art and described herein, for example, using indicators including ALSFSR-R, and measurements of FEV1, FVC, and muscle strength. These methods are used by a physician to assess disease state at initiation of treatment, and to provide a baseline for disease state. Subsequent assessments are performed at intervals, as determined by the physician, during the delivery period. Expression of BDNF protein and mRNA in cerebrospinal fluid is assayed. Human BDNF protein concentration and secretion levels are determined using an enzyme linked immunosorbent assay (ELISA) kit (e.g., Quantikine human BDNF, R&D Systems, Minneapolis, Minn.), according to the manufacturer's instructions. mRNA is assayed using RT-PCR, as described elsewhere herein.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The Abstract of the disclosure will allow the reader to quickly ascertain the nature of the technical disclosure. It is submitted with the understanding that it will not be used to interpret or limit the scope or meaning of the following claims.

---

The invention claimed is:

1. A synthetic, modified single-stranded oligonucleotide of 15 to 18 nucleotides in length comprising at least one modification wherein the at least one modification is selected from: at least one modified sugar moiety; at least one modified internucleotide linkage; at least one modified nucleotide, and combinations thereof; wherein said oligonucleotide is (i) an antisense compound which is 100% complementary to and specifically hybridizes to a 15 to 18 nucleotide target region within nucleotides 1-2535 of a natural antisense polynucleotide of a Brain derived neurotrophic factor polynucleotide having SEQ ID NO: 2 and (ii) is specific for said natural antisense polynucleotide and upregulates the function and/or expression of a Brain derived neurotrophic factor (BDNF) gene in vivo or in vitro as compared to a mock-transfected control and wherein there is at least a 1.4 fold average increase in expression over said control.

2. The oligonucleotide of claim 1, wherein the at least one modification comprises an internucleotide linkage selected from the group consisting of: phosphorothioate, alkylphosphonate, phosphorodithioate, alkylphosphonothioate, phosphoramidate, carbamate, carbonate, phosphate triester, acetamidate, carboxymethyl ester, and combinations thereof.

3. The oligonucleotide of claim 1, wherein said oligonucleotide comprises at least one phosphorothioate internucleotide linkage.

4. The oligonucleotide of claim 1, wherein said oligonucleotide comprises a backbone of phosphorothioate internucleotide linkages.

5. The oligonucleotide of claim 1, wherein the oligonucleotide comprises at least one modified nucleotide, said modified nucleotide selected from: a peptide nucleic acid, a locked nucleic acid (LNA), and a combination thereof.

6. The oligonucleotide of claim 1, wherein the oligonucleotide comprises a plurality of modifications, wherein said modifications comprise modified nucleotides selected from: phosphorothioate, alkylphosphonate, phosphorodithioate, alkylphosphonothioate, phosphoramidate, carbamate, carbonate, phosphate triester, acetamidate, carboxymethyl ester, and a combination thereof.

7. The oligonucleotide of claim 1, wherein the oligonucleotide comprises a plurality of modifications, wherein said modifications comprise modified nucleotides selected from: peptide nucleic acids, locked nucleic acids (LNA), and a combination thereof.

8. The oligonucleotide of claim 1, wherein the oligonucleotide comprises at least one modified sugar moiety selected from: a 2'-O-methoxyethyl modified sugar moiety, a 2'-methoxy modified sugar moiety, a 2'-O-alkyl modified sugar moiety, a bicyclic sugar moiety, and a combination thereof.

9. The oligonucleotide of claim 1, wherein the oligonucleotide comprises a plurality of modifications, wherein said modifications comprise modified sugar moieties selected from: a 2'-O-methoxyethyl modified sugar moiety, a 2'-methoxy modified sugar moiety, a 2'-O-alkyl modified sugar moiety, a bicyclic sugar moiety, and a combination thereof.

10. The oligonucleotide of claim 1, wherein the oligonucleotide specifically hybridizes to a non-overlapping region of said natural antisense polynucleotide having SEQ ID NO: 2 wherein said non-overlapping region is non-overlapping with the mRNA of the BDNF polynucleotide.

11. The oligonucleotide of claim 1, wherein the oligonucleotide has at least about 100% sequence identity to a sequence of at least about 15 consecutive nucleotides of the mRNA sense coding and/or noncoding nucleic acid sequence of the Brain derived neurotrophic factor (BDNF) polynucleotide.

12. The oligonucleotide of claim 1, wherein the oligonucleotide comprises the sequences set forth as SEQ ID NOS: 4, 6 and 8.

13. A composition comprising one or more oligonucleotides according to claim 1 and a pharmaceutically acceptable excipient.

14. The composition of claim 13, wherein the at least one of the one or more oligonucleotides comprises one of the nucleotide sequences set forth as SEQ ID NOS: 4, 6 and 8.

15. The composition of claim 14, wherein the oligonucleotidesset forth as SEQ ID NOs: 4, 6 and 8 comprise two or more modifications or substitutions selected from a locked nucleic acid (LNA), phosphorothioate, methylphosphonate, peptide nucleicacid, and combinations thereof.

* * * * *